US012606864B2

(12) United States Patent
Nelson et al.

(10) Patent No.: US 12,606,864 B2
(45) Date of Patent: Apr. 21, 2026

(54) COMPOSITIONS, KITS AND METHODS FOR ISOLATING TARGET POLYNUCLEOTIDES

(71) Applicant: DNAe Diagnostics Limited, London (GB)

(72) Inventors: Norm Nelson, San Diego, CA (US); David Wooldridge, London (GB)

(73) Assignee: DNAe Diagnostics Limited, London (GB)

( * ) Notice: Subject to any disclaimer, the term of this patent is extended or adjusted under 35 U.S.C. 154(b) by 892 days.

(21) Appl. No.: 17/758,906

(22) PCT Filed: Jan. 15, 2021

(86) PCT No.: PCT/GB2021/050098
§ 371 (c)(1),
(2) Date: Jul. 15, 2022

(87) PCT Pub. No.: WO2021/144587
PCT Pub. Date: Jul. 22, 2021

(65) Prior Publication Data
US 2023/0227896 A1    Jul. 20, 2023

Related U.S. Application Data

(60) Provisional application No. 62/961,816, filed on Jan. 16, 2020.

(30) Foreign Application Priority Data

Jan. 16, 2020    (GB) ...................................... 2000672
Jan. 16, 2020    (GB) ...................................... 2000673

(51) Int. Cl.
*C12Q 1/68*        (2018.01)
*C12Q 1/6851*      (2018.01)
(Continued)

(52) U.S. Cl.
CPC ......... *C12Q 1/6851* (2013.01); *C12Q 1/6855* (2013.01); *C12Q 1/689* (2013.01)

(58) Field of Classification Search
None
See application file for complete search history.

(56) References Cited

U.S. PATENT DOCUMENTS 11,268,137 B2 *    3/2022    Marziali ................... C12Q 1/68
11,408,025 B2 *    8/2022    Fu ........................ C12Q 1/6806
(Continued)

FOREIGN PATENT DOCUMENTS

WO         2011008530 A2      1/2011
WO         2018087200 A1      5/2018
WO         WO-2021232023 A2 *  11/2021    ............. C12Q 1/686

OTHER PUBLICATIONS

Notification of Transmittal of the International Search Report and the Written Opinion of the International Searching Authority, International Search Report, and Written Opinion of the International Searching Authority for PCT/GB2021/050098, mailed on May 25, 2021, 18 pages.

*Primary Examiner* — Aaron A Priest
(74) *Attorney, Agent, or Firm* — McNeill PLLC

(57)    ABSTRACT

Provided herein are oligomers, compositions, kits, and methods for capturing target polynucleotides, e.g., for downstream applications such as amplification, library preparation, or sequencing. In some embodiments, a capture oligomer is provided or used that comprises a capture sequence that is annealed to a complement that prevents capture until the complement is displaced in a target-polynucleotide dependent manner. In some embodiments, an amount of target polynucleotide is captured that is less than or equal to a predetermined amount.

9 Claims, 19 Drawing Sheets
Specification includes a Sequence Listing.

(51) Int. Cl.
  *C12Q 1/6855*       (2018.01)
  *C12Q 1/689*       (2018.01)

(56)       References Cited

U.S. PATENT DOCUMENTS

2017/0002404 A1* 1/2017 Coll Mulet ............ C07H 21/04
2020/0115736 A1* 4/2020 Fu ........................ C12Q 1/6806
2022/0348906 A1* 11/2022 Harkins Kincaid . C12Q 1/6869

* cited by examiner

Streptavidin coated magnetic bead

S1'   C2'

3' ———————————————————————————— 5'

THS      S2    S1    C2    C1

S1'    C2'

5'

S

THS      C

S'

THS      S     C

C'

S1'     C2'

+

THS      S2    S1    C2    C1

C'

Capture of the tagged
amplicon using secondary capture reagent

```
                            SEQUENCE LISTING

<160> NUMBER OF SEQ ID NOS: 36

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
gtatcagcgc gaagtcttta tacc                                              24

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
ggcaataaca tacggagtga catc                                              24

<210> SEQ ID NO 3
<211> LENGTH: 169
<212> TYPE: DNA
<213> ORGANISM: Artificial Sequence
<220> FEATURE:
<223> OTHER INFORMATION: Synthetic

<400> SEQUENCE: 3
gtatcagcgc gaagtcttta taccgaaagg ttgggcgggc cagcgtattg tactgcgttt       60
cgatgcggtc actcattacg gcaaagtgtg ggtaaataat caggaagtga tggagcatca      120
gggcggctat acgccatttg aagccgatgt cactccgtat gttattgcc                  169

<210> SEQ ID NO 4
<211> LENGTH: 128
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (41)..(42)
<223> OTHER INFORMATION: site of iSp18 (Hexaethylene Glycol (HEG)
      internal spacer)

<400> SEQUENCE: 4
aaaaaaaaaa aaaaaaaaaa aaaaaaaaaa aaaaacctct attttttttt tttttttttt       60
tttttttttt ttttttagac gcaagctact ggtgatttgg caataacata cggagtgaca      120
tcggcttc                                                               128

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
agacgcaagc tactggtgat tt                                                22
```

<210> SEQ ID NO 6
<211> LENGTH: 30
<212> TYPE: DNA
<213> ORGANISM: Artificial Sequence
<220> FEATURE:
<223> OTHER INFORMATION: Synthetic

<400> SEQUENCE: 6
ggcaataaca tacggagtga catcggcttc                                          30

<210> SEQ ID NO 7
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' Biotin

<400> SEQUENCE: 7
tttttttttt tttttttttt                                                     20

<210> SEQ ID NO 8
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' FAM, 3' IowaBlack

<400> SEQUENCE: 8
tagccgccct gatgctccat cacttcctg                                           29

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
agacgcaagc tactggtgat                                                     20

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
ggctgcgata ttcaaagctc ag                                                  22

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
ctgaacgcgc cggcttaac                                                      19

-continued

<210> SEQ ID NO 12
<211> LENGTH: 166
<212> TYPE: DNA
<213> ORGANISM: Artificial Sequence
<220> FEATURE:
<223> OTHER INFORMATION: Synthetic

<400> SEQUENCE: 12
ggctgcgata ttcaaagctc agcaatttgt atggacaaat cgttgacata catcgttgcg      60
aaaaatgctg ggatagctac tcccgccttt tgggttatta ataaagatga taggccggtg     120
gcagctacgt ttacctatcc tgtttttgtt aagccggcgc gttcag                    166

<210> SEQ ID NO 13
<211> LENGTH: 77
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: site of iSp18 (Hexaethylene Glycol (HEG)
      internal spacer)

<400> SEQUENCE: 13
aaaaaaaaaa aaaaaaaaaa ctcctctggc accgtgctgc cttggcttca ttgtggtcct      60
gaacgcgccg gcttaac                                                     77

<210> SEQ ID NO 14
<211> LENGTH: 38
<212> TYPE: DNA
<213> ORGANISM: Artificial Sequence
<220> FEATURE:
<223> OTHER INFORMATION: Synthetic

<400> SEQUENCE: 14
ctcctctggc accgtgctgc cttggcttca ttgtggtc                              38

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15
ctgaacgcgc cggcttaac                                                   19

<210> SEQ ID NO 16
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' invdt

<400> SEQUENCE: 16
cggtgccaga ggagtttttt tttt                                             24

<210> SEQ ID NO 17
<211> LENGTH: 14
<212> TYPE: DNA
<213> ORGANISM: Artificial Sequence

```
<220> FEATURE:
<223> OTHER INFORMATION: Synthetic

<400> SEQUENCE: 17
cggtgccaga ggag                                                              14

<210> SEQ ID NO 18
<211> LENGTH: 10
<212> TYPE: DNA
<213> ORGANISM: Artificial Sequence
<220> FEATURE:
<223> OTHER INFORMATION: Synthetic

<400> SEQUENCE: 18
tttttttttt                                                                   10

<210> SEQ ID NO 19
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' Biotin

<400> SEQUENCE: 19
tttttttttt tttttttttt                                                        20

<210> SEQ ID NO 20
<211> LENGTH: 26
<212> TYPE: DNA
<213> ORGANISM: Artificial Sequence
<220> FEATURE:
<223> OTHER INFORMATION: Synthetic

<400> SEQUENCE: 20
ttgtatggac aaatcgttga cataca                                                 26

<210> SEQ ID NO 21
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' FAM, 3' IowaBlack

<400> SEQUENCE: 21
tgctgggata gctactcccg ccttttgg                                               28

<210> SEQ ID NO 22
<211> LENGTH: 19
<212> TYPE: DNA
<213> ORGANISM: Artificial Sequence
<220> FEATURE:
<223> OTHER INFORMATION: Synthetic

<400> SEQUENCE: 22
accgtgctgc cttggcttc                                                         19

<210> SEQ ID NO 23
<211> LENGTH: 22
<212> TYPE: DNA
<213> ORGANISM: Artificial Sequence
<220> FEATURE:
```

```
<223> OTHER INFORMATION: Synthetic

<400> SEQUENCE: 23
ggctgcgata ttcaaagctc ag                                            22

<210> SEQ ID NO 24
<211> LENGTH: 19
<212> TYPE: DNA
<213> ORGANISM: Artificial Sequence
<220> FEATURE:
<223> OTHER INFORMATION: Synthetic

<400> SEQUENCE: 24
ctgaacgcgc cggcttaac                                                19

<210> SEQ ID NO 25
<211> LENGTH: 166
<212> TYPE: DNA
<213> ORGANISM: Artificial Sequence
<220> FEATURE:
<223> OTHER INFORMATION: Synthetic

<400> SEQUENCE: 25
ggctgcgata ttcaaagctc agcaatttgt atggacaaat cgttgacata catcgttgcg    60
aaaaatgctg ggatagctac tcccgccttt tgggttatta ataaagatga taggccggtg   120
gcagctacgt ttacctatcc tgtttttgtt aagccggcgc gttcag                  166

<210> SEQ ID NO 26
<211> LENGTH: 77
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: site of iSp18 (Hexaethylene Glycol (HEG)
      internal spacer)

<400> SEQUENCE: 26
aaaaaaaaaa aaaaaaaaaa ctcctctggc accgtgctgc cttggcttca ttgtggtcgt    60
agctgccacc ggcctat                                                  77

<210> SEQ ID NO 27
<211> LENGTH: 38
<212> TYPE: DNA
<213> ORGANISM: Artificial Sequence
<220> FEATURE:
<223> OTHER INFORMATION: Synthetic

<400> SEQUENCE: 27
ctcctctggc accgtgctgc cttggcttca ttgtggtc                            38

<210> SEQ ID NO 28
<211> LENGTH: 19
<212> TYPE: DNA
<213> ORGANISM: Artificial Sequence
<220> FEATURE:
<223> OTHER INFORMATION: Synthetic

<400> SEQUENCE: 28
gtagctgcca ccggcctat                                                19

<210> SEQ ID NO 29
```

```
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' invdt

<400> SEQUENCE: 29
cggtgccaga ggagtttttt tttt                                          24

<210> SEQ ID NO 30
<211> LENGTH: 14
<212> TYPE: DNA
<213> ORGANISM: Artificial Sequence
<220> FEATURE:
<223> OTHER INFORMATION: Synthetic

<400> SEQUENCE: 30
cggtgccaga ggag                                                     14

<210> SEQ ID NO 31
<211> LENGTH: 10
<212> TYPE: DNA
<213> ORGANISM: Artificial Sequence
<220> FEATURE:
<223> OTHER INFORMATION: Synthetic

<400> SEQUENCE: 31
tttttttttt                                                          10

<210> SEQ ID NO 32
<211> LENGTH: 47
<212> TYPE: DNA
<213> ORGANISM: Artificial Sequence
<220> FEATURE:
<223> OTHER INFORMATION: Synthetic

<400> SEQUENCE: 32
aaaacgagac atgccgagca tccgcggctg cgatattcaa agctcag                 47

<210> SEQ ID NO 33
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' Biotin

<400> SEQUENCE: 33
tttttttttt tttttttttt                                               20

<210> SEQ ID NO 34
<211> LENGTH: 22
<212> TYPE: DNA
<213> ORGANISM: Artificial Sequence
<220> FEATURE:
<223> OTHER INFORMATION: Synthetic

<400> SEQUENCE: 34
aaaacgagac atgccgagca tc                                            22

<210> SEQ ID NO 35
<211> LENGTH: 28
```

-continued

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' FAM, 3' IowaBlack

<400> SEQUENCE: 35
tgctgggata gctactcccg ccttttgg                                    28

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
accgtgctgc cttggcttc                                              19
```

1

COMPOSITIONS, KITS AND METHODS FOR ISOLATING TARGET POLYNUCLEOTIDES

This application claims the benefit of priority of U.S. Provisional Patent Application No. 62/961,816, filed Jan. 16, 2020, GB Patent Application No. 2000673.0, filed Jan. 16, 2020, and GB Patent Application No. 2000672.2, filed Jan. 16, 2020, each of which is incorporated herein by reference in its entirety for all purposes.

I. INTRODUCTION AND SUMMARY

The embodiments herein are directed isolating target polynucleotides, such as polynucleotides from an organism of interest and amplicons, from compositions. The embodiments are useful, e.g., as part of workflows to prepare target polynucleotides for sequencing or other analyses.

Certain biochemical and molecular biological procedures benefit from or require a defined amount of input nucleic acid. For example, sequencing library preparation procedures may have a range of acceptable amounts of nucleic acid, wherein an amount below the minimum results in wasted bandwidth and low data output, and an amount above the maximum results in poor library quality. Further, a predetermined amount of library nucleic acid (frequently expressed as "number of molecules") is generally desired for use in the clonal amplification step of a sequencing workflow (when utilized) to avoid polyclonal molecule populations on one side and wasted bandwidth and low data output on the other side as well as use in single molecule sequencing workflows where a defined number of molecules input into the sequencing step is desirable for optimal results. For applications where time is critical, such as rapid detection of pathogens by sequencing a clinical sample, existing approaches for providing a sample with an acceptable amount of nucleic acid, e.g., involving a quantification procedure and subsequent concentration or dilution steps, may be undesirably slow. Additionally, various existing methods may suffer from other problems, such as saturation of solid supports by excess capture oligomer and complexities relating to addition of adaptors or other sequences.

Accordingly, there is a need for compositions and methods that can provide improved nucleic acid capture, including, e.g., rapid and accurate capture of nucleic acid in a controlled or limited way, e.g., an amount less than or equal to a predetermined amount; capture oligomers that are captureable in a target-dependent manner; and streamlined addition of adaptors or other sequences. This disclosure aims to provide compositions and methods that meet one or more of these needs, provide other benefits, or at least provide the public with a useful choice. Capture oligomers, combinations of capture oligomers and other oligomers, and related compositions, kits, and methods are provided herein for capturing and/or controlling the amount of a nucleic acid, e.g., in which a defined amount of a capture oligomer or another limiting reagent (e.g., a secondary capture reagent) or a combination thereof can control the output of a capture procedure and the capture oligomer becomes captureable in a target-dependent manner; and/or adding adaptors or other sequences in a streamlined manner.

More particularly, provided herein are the following embodiments. Embodiment 1 is a capture oligomer comprising, in the 5' to 3' direction:

a capture sequence,
an internal extension blocker,
a complement of the capture sequence, and
a target-hybridizing sequence,

2 wherein the complement of the capture sequence is configured to anneal to the capture sequence in the absence of an extended target sequence annealed to the target-hybridizing sequence and the complement of the capture sequence.

Embodiment 2 is the capture oligomer of embodiment 1, wherein the capture oligomer has the formula

5'-A1-C-L-B-A2-C'-A3-RB-A4-THS-X-3' wherein A1 is an optionally present first additional sequence;
C is the capture sequence,
L is an optionally present linker,
B is the internal extension blocker,
A2 is an optionally present second additional sequence,
C' is the complement of the capture sequence,
A3 is an optionally present third additional sequence,
RB is an optionally present reversible extension blocker,
A4 is an optionally present fourth additional sequence,
THS is the target-hybridizing sequence; and
X is an optionally present blocking moiety.

Embodiment 3 is the capture oligomer of any one of the preceding embodiments, wherein the capture sequence comprises a poly A or poly T sequence and the complement of the capture sequence comprises a poly T or poly A sequence.

Embodiment 4 is the capture oligomer of any one of the preceding embodiments, wherein the capture oligomer comprises a first additional sequence 5' of the capture sequence and a third additional sequence 3' of the complement of the capture sequence which comprise first and second stabilizing sequences, respectively, optionally wherein the stabilizing sequences are GC-clamp sequences.

Embodiment 5 is the capture oligomer of the immediately preceding embodiment, wherein the first stabilizing sequence is located 5' of the remainder of the capture sequence and/or the second stabilizing sequence is located 3' of the remainder of the complement of the capture sequence.

Embodiment 6 is the capture oligomer of embodiment 4 or 5, wherein the GC-clamp sequences each comprise a $(GC)_3$ sequence or a $(CG)_3$ sequence.

Embodiment 7 is the capture oligomer of any one of the preceding embodiments, comprising a linker, which is optionally a nucleotide sequence or a non-nucleotide linker or a combination thereof, between the capture sequence and the internal extension blocker.

Embodiment 8 is the capture oligomer of any one of the preceding embodiments, wherein the internal extension blocker comprises any one or more of a non-nucleotide linker, or one or more abasic sites, non-natural nucleotides, or chemically modified natural nucleotides.

Embodiment 9 is the capture oligomer of any one of the preceding embodiments, comprising a third additional sequence that comprises an adaptor sequence between the complement of the capture sequence and the THS.

Embodiment 10 is the capture oligomer of any one of the preceding embodiments, wherein the capture oligomer comprises a reversible extension blocker located 5' of the target-hybridizing sequence.

Embodiment 11 is the capture oligomer of the immediately preceding embodiment wherein the reversible extension blocker is located 3' of the complement of the capture sequence.

Embodiment 12 is the capture oligomer of embodiment 10 or 11, wherein the capture oligomer comprises a third additional sequence located 3' of the complement of the capture sequence and 5' of the target-hybridizing sequence, and the reversible extension blocker is located 3' of the adaptor sequence, optionally wherein the third additional sequence comprises an adaptor sequence.

Embodiment 13 is the capture oligomer of any one of the preceding embodiments, wherein the capture oligomer comprises a fourth additional sequence located 3' of the reversible blocker and 5' of the target-hybridizing sequence, optionally wherein the fourth additional sequence comprises an adaptor sequence.

Embodiment 14 is the capture oligomer of any one of the preceding embodiments, comprising a second additional sequence between the internal extension blocker and the complement of the capture sequence, optionally wherein the second additional sequence comprises a mixed-nucleotide segment.

Embodiment 15 is the capture oligomer of the immediately preceding embodiment, wherein the reversible extension blocker comprises Iso-dC or Iso-dG, xanthine or 5-(2,4 diaminopyrimidine), 2-amino-6-(N,N-dimethylamino)purine or pyridine-2-one, 4-Methylbenzimidizole or 2,4 Difluorotoluene, 7-Azaindole or Isocarbostyril, dMMO2 or d5SICS, dF or dQ; a chemically modified nucleotide or nucleotides wherein the modification is attached via a reversible linkage and the linkage can be reversed by providing any one or more of a chemical, an enzyme, a temperature change, a reagent composition change; a reversible nucleic acid structural feature; or a molecule reversibly bound to the capture oligomer, optionally wherein the reversibly bound molecule is a protein, an enzyme, a lipid, a carbohydrate, or a chemical moiety.

Embodiment 16 is the capture oligomer of any one of the preceding embodiments, wherein the target-hybridizing sequence comprises a blocking moiety at its 3' end.

Embodiment 17 is the capture oligomer of any one of the preceding embodiments, comprising one or more affinity-enhancing modifications (e.g., any one or more of 5-Me-C, 2-aminopurine, 2'-fluoro, C-5-propyne, LNA, PNA, ZNA, phosphorothioate, 2'-OMe, or constrained ethyl (cEt) substitutions), e.g., in the target-hybridizing sequence.

Embodiment 18 is a combination comprising the capture oligomer of any one of the preceding embodiments and a secondary capture reagent comprising a complement of the capture sequence and (a) a binding partner (e.g., biotin) or (b) a solid support (e.g., bead or surface).

Embodiment 19 is The combination of the immediately preceding embodiment, wherein the combination further comprises a second capture oligomer and a second secondary capture reagent, wherein the second capture oligomer comprises a second target hybridizing sequence different from the target hybridizing sequence of the capture oligomer and a second capture sequence different from the capture sequence of the capture oligomer, and the second secondary capture reagent comprises a complement of the second capture sequence and (a) a binding partner (e.g., biotin) or (b) a solid support (e.g., bead or surface).

Embodiment 20 is the combination of embodiment 18, wherein the secondary capture reagent comprises a complement of the capture sequence and a binding partner (e.g., biotin), and the combination further comprises a solid support (e.g., beads) comprising a second binding partner (e.g., a biotin-binding agent such as streptavidin) configured to bind the binding partner of the secondary capture reagent.

Embodiment 21 is a combination comprising the capture oligomer or combination of any one of the preceding embodiments, wherein the capture oligomer comprises an adaptor sequence 5' of the target-hybridizing sequence, and the combination further comprises a blocker oligomer comprising the adaptor sequence, which is non-extendable, optionally wherein the blocker oligomer is configured to bind the complement of the adaptor sequence with a greater affinity than the adaptor sequence of the capture oligomer or to form a complex with the complement of the adaptor sequence having a higher melting temperature than a complex of the adaptor sequence of the capture oligomer and the complement of the adaptor sequence.

Embodiment 22 is a combination comprising the capture oligomer or combination of any one of the preceding embodiments, wherein the capture oligomer comprises an adaptor sequence 5' of the target-hybridizing sequence and the combination further comprises a second oligomer comprising a second target-hybridizing sequence 5' of a complement of at least a portion of the adaptor sequence, wherein in the presence of a target polynucleotide with accessible complements of the first and second target-hybridizing sequences, the capture oligomer and the second oligomer are configured to form a three-strand junction with the target polynucleotide.

Embodiment 23 is a reaction mixture comprising the capture oligomer or combination of any one of the preceding embodiments and a target polynucleotide.

Embodiment 24 is the reaction mixture of the immediately preceding embodiment, wherein the target is an amplicon, optionally further comprising at least one amplification primer, further optionally wherein the target-hybridizing sequence of the capture oligomer has a greater affinity for the amplicon than the primer (e.g., longer THS or affinity-enhancing modifications).

Embodiment 25 is the reaction mixture of any one of embodiments 23 or 24, further comprising a second capture oligomer, a second secondary capture reagent, and a second target polynucleotide, wherein the second capture oligomer comprises a second target hybridizing sequence configured to anneal to the second target polynucleotide and a second capture sequence different from the capture sequence of the capture oligomer, and the second secondary capture reagent comprises a complement of the second capture sequence and (a) a binding partner (e.g., biotin) or (b) a solid support (e.g., bead or surface).

Embodiment 26 is the reaction mixture of the immediately preceding embodiment, wherein the second target polynucleotide is present at a lower concentration than the target polynucleotide.

Embodiment 27 is the reaction mixture of any one of embodiments 25 or 26, wherein the target polynucleotide and the second target polynucleotide were isolated or generated from a sample from an organism or type of environment and the second target polynucleotide is less commonly observed in samples from the organism or the type of environment.

Embodiment 28 is a combination comprising a capture oligomer and a complementary oligomer, wherein:

(a) the capture oligomer comprises, in the 5' to 3' direction:

a capture sequence comprising first and second portions, an internal extension blocker, a spacer sequence comprising first and second portions, and a target-hybridizing sequence; and (b) the complementary oligomer comprises, in the 3' to 5' direction:

a complement of the second portion of the capture sequence, and a complement of at least the first portion of the spacer sequence, wherein the complement of the second portion of the capture sequence and the complement of the at least first portion of the spacer sequence are config-
ured to anneal simultaneously to the capture oligomer
in the absence of a complement of the spacer sequence.

Embodiment 29 is the combination of the immediately
preceding embodiment, wherein the capture oligomer has
the formula:

5'-A1-C1-C2-B-A2-S1-S2-A3-RB-A4-THS-X-3' wherein A1 is an optionally present first additional
sequence,

C1 is the first portion of the capture sequence,

C2 is the second portion of the capture sequence,

B is the internal extension blocker,

A2 is an optionally present second additional sequence,

S1 is the first portion of the spacer sequence,

S2 is the second portion of the spacer sequence,

A3 is an optionally present third additional sequence,

RB is an optionally present reversible extension blocker,

A4 is an optionally present fourth additional sequence,

THS is the target-hybridizing sequence, and

X is an optionally present blocking moiety.

Embodiment 30 is the combination of any one of embodi-
ments 28 or 29, wherein the complementary oligomer has
the formula:

5'-S1'-A2'-L-C2'-X-3' wherein S1' is the complement of at least the first portion
of the spacer sequence, A2' is an optionally present complement of a second
additional sequence which is optionally present in the
capture oligomer;

L is an optionally present linker,

C2' is the complement of the second portion of the capture
sequence, and

X is an optionally present blocking moiety.

Embodiment 31 is a combination comprising a capture
oligomer and a complementary oligomer, wherein:

(a) the capture oligomer comprises, in the 5' to 3' direc-
tion:

a capture sequence comprising first and second portions,
and a target-hybridizing sequence comprising second and first
portions; and (b) the complementary oligomer comprises, in the 3' to 5'
direction:

a complement of the second portion of the capture
sequence, and a complement of the second portion of the target-hybrid-
izing sequence, wherein the complement of the second
portion of the capture sequence and the complement of
the second portion of the target-hybridizing sequence
are configured to anneal simultaneously to the capture
oligomer in the absence of a complement of the target-
hybridizing sequence.

Embodiment 32 is the combination of the immediately
preceding embodiment, wherein the capture oligomer has
the formula:

5'-A1-C1-C2-A2-S-A3-THS2-THS1-X-3' wherein A1 is an optionally present first additional
sequence,

C1 is the first portion of the capture sequence,

C2 is the second portion of the capture sequence,

A2 is an optionally present second additional sequence,

S is an optionally present spacer sequence,

A3 is an optionally present third additional sequence,

THS2 is the second portion of the target-hybridizing
sequence,

THS1 is the first portion of the target-hybridizing
sequence, and

X is an optionally present blocking moiety.

Embodiment 33 is the combination of any one of embodi-
ments 31 or 32, wherein the complementary oligomer has
the formula:

5'-THS2'-A3'-S'-A2'-C2'-X-3' wherein THS2' is the complement of the second portion of
the target-hybridizing sequence, A3' is an optionally present complement of a third addi-
tional sequence which is optionally present in the
capture oligomer;

S' is an optionally present complement of a spacer which
is optionally present in the capture oligomer, A2' is an optionally present complement of a second
additional sequence which is optionally present in the
capture oligomer;

C2' is the complement of the second portion of the capture
sequence, and

X is an optionally present blocking moiety.

Embodiment 34 is the combination of any one of embodi-
ments 28-33, wherein the capture oligomer and/or comple-
mentary oligomer comprises a blocking moiety at its 3' end.

Embodiment 35 is the combination of any one of embodi-
ments 28-34, wherein the complement of the second portion
of the capture sequence is insufficient to stably anneal to the
capture sequence of the capture oligomer at or above a
temperature of 65° C. if the spacer sequence of the capture
oligomer is occupied by a separate complement.

Embodiment 36 is the capture oligomer, reaction mixture,
or combination of any one of the preceding embodiments,
wherein the capture sequence comprises poly A or poly T
and the complement of the capture sequence, or the comple-
ment of the second portion of the capture sequence, com-
prises poly T or poly A.

Embodiment 37 is the capture oligomer, reaction mixture,
or combination of any one of the preceding embodiments,
wherein the capture oligomer comprises an adaptor
sequence as part or all of the spacer sequence or as part or
all of a third additional sequence 3' of the spacer sequence
or a fourth additional sequence 5' of the target-hybridizing
sequence.

Embodiment 38 is the capture oligomer, reaction mixture,
or combination of any one of the preceding embodiments,
wherein the capture oligomer comprises affinity-enhancing
modifications (e.g., any one or more of 5-Me-C, 2-aminopu-
rine, 2'-fluoro, C-5-propyne, LNA, PNA, ZNA, phosphoro-
thioate, 2'-OMe, or constrained ethyl (cEt) substitutions),
e.g., in the target-hybridizing sequence.

Embodiment 39 is the capture oligomer, reaction mixture,
or combination of any one of the preceding embodiments,
wherein the capture oligomer comprises a reversible exten-
sion blocker located 5' of the target-hybridizing sequence.

Embodiment 40 is the capture oligomer, reaction mixture,
or combination of the immediately preceding embodiment,
wherein the reversible extension blocker is located 3' of the
second portion of the spacer sequence.

Embodiment 41 is the capture oligomer, reaction mixture,
or combination of any one of embodiments 39 or 40,
wherein the reversible extension blocker comprises Iso-dC
or Iso-dG, xanthine or 5-(2,4 diaminopyrimidine), 2-amino-
6-(N,N-dimethylamino)purine or pyridine one, 4-Methyl-
benzimidizole or 2,4 Difluorotoluene, 7-Azaindole or Iso-
carbostyril, dMMO2 or d5SICS, dF or dQ, a chemically modified nucleotide or nucleotides wherein the modification is attached via a reversible linkage, optionally wherein the linkage is reversible via any one or any combination of two or more of a chemical, an enzyme, a temperature change, or a reagent composition change, a reversible nucleic acid structural feature, reversible binding to the nucleic acid template of a protein, an enzyme, a lipid, a carbohydrate, or a chemical moiety.

Embodiment 42 is the capture oligomer, reaction mixture, or combination of any one of embodiments 28-41, comprising a second additional sequence between the internal extension blocker and the first portion of the spacer sequence, wherein the second additional sequence comprises a mixed-nucleotide segment.

Embodiment 43 is the capture oligomer, reaction mixture, or combination of the immediately preceding embodiment wherein the mixed-nucleotide segment comprises 5 nucleotides in which each nucleotide differs from its nearest neighbors.

Embodiment 44 is the capture oligomer, reaction mixture, or combination of any one of embodiments 42 or 43, wherein the mixed-nucleotide segment is free of repeating dinucleotides, repeating trinucleotides, and/or adjacent repeats.

Embodiment 45 is the capture oligomer, reaction mixture, or combination of any one of embodiments 42-44, further comprising a splint oligomer comprising, in the 5' to 3' direction:

a complement of a sequence not present in the capture oligomer;

the mixed-nucleotide segment; and a complement of the capture sequence.

Embodiment 46 is the capture oligomer, reaction mixture, or combination of the immediately preceding embodiment, wherein the capture oligomer comprises a third or fourth additional sequence comprising an adaptor sequence between the target-hybridizing sequence and the second portion of the spacer sequence, or the target-hybridizing sequence of the capture oligomer is an adaptor sequence; and the splint oligomer further comprises a complement of the adaptor sequence 3' of its complement of the capture sequence.

Embodiment 47 is the capture oligomer, reaction mixture, or combination of any one of embodiments 28-46, further comprising a secondary capture reagent comprising a complement of the capture sequence and (a) a binding partner (e.g., biotin) or (b) a solid support (e.g., bead or surface).

Embodiment 48 is the capture oligomer, reaction mixture, or combination of the immediately preceding embodiment, wherein the secondary capture reagent comprises the binding partner and the combination further comprises a solid support (e.g., one or more beads) comprising a second binding partner configured to bind the binding partner of the secondary capture reagent, optionally wherein the binding partner of the secondary capture reagent is biotin and the second binding partner is a biotin-binding agent (e.g., streptavidin).

Embodiment 49 is the capture oligomer, reaction mixture, or combination of any one of embodiments 28-48, further comprising a displacer oligomer comprising a displacer target-hybridizing sequence configured to bind the target polynucleotide in an orientation wherein the 3' end of the displacer target-hybridizing sequence is oriented toward the site bound by the target-hybridizing sequence of the capture oligomer.

Embodiment 50 is the capture oligomer, reaction mixture, or combination of the immediately preceding embodiment, wherein the capture oligomer comprises an adaptor sequence located 5' of the target-hybridizing sequence and 3' of the complement of the capture sequence.

Embodiment 51 is the capture oligomer, reaction mixture, or combination of any one of embodiments 49 or 50, further comprising an amplification oligomer that comprises a reverse target-hybridizing sequence configured to bind the target polynucleotide in an opposite orientation relative to the capture oligomer and optionally further comprises a second adaptor sequence located 5' of the reverse target-hybridizing sequence.

Embodiment 52 is a reaction mixture comprising the capture oligomer or combination of any one of the preceding embodiments and further comprising a target polynucleotide.

Embodiment 53 is the reaction mixture of the immediately preceding embodiment, wherein the target is an amplicon, further comprising amplification primers including an amplification primer that binds the same strand as the capture oligomer, optionally wherein the THS of the capture oligomer has a greater affinity for the amplicon than the primer that binds the same strand as the capture oligomer (e.g., wherein the capture oligomer has a longer THS than the primer that binds the same strand as the capture oligomer, or the capture oligomer comprises affinity-enhancing modifications).

Embodiment 54 is a combination comprising the capture oligomer or combination of any one of embodiments 1-51 and an amplification oligomer, wherein:

the capture oligomer comprises a first adaptor sequence between the target hybridizing sequence and the internal extension blocker, and the amplification oligomer comprises (i) a reverse target-hybridizing sequence that binds the target polynucleotide in a reverse orientation relative to the capture oligomer and (ii) a second adaptor sequence located 5' of the reverse target hybridizing sequence.

Embodiment 55 is the combination of the immediately preceding embodiment wherein the capture oligomer comprises a blocking moiety at its 3' end.

Embodiment 56 is the combination of embodiment 54, wherein the capture oligomer is extendable.

Embodiment 57 is the combination of any one of embodiments 54-56, wherein the amplification oligomer comprises a reversible extension blocker located between the second adaptor sequence and the reverse target-hybridizing sequence, optionally wherein the capture oligomer further comprises a reversible extension blocker located between the target-hybridizing sequence and the first adaptor sequence.

Embodiment 58 is a method of capturing a target polynucleotide from a composition, the method comprising:

contacting the target polynucleotide with the capture oligomer of any one of embodiments 1-22 or 36-51, wherein the target-hybridizing sequence of the capture oligomer anneals to the target polynucleotide at a site comprising the 3' end of the target polynucleotide;

extending the 3' end of the target polynucleotide with a DNA polymerase with strand-displacement activity, thereby forming a complement of the complement of the capture sequence, which is annealed to the capture oligomer, such that the capture sequence of the capture oligomer is available for binding;

contacting the capture sequence of the capture oligomer with a secondary capture reagent comprising a complement of the capture sequence and (i) a binding partner or (ii) a solid support, thereby forming a complex comprising the target polynucleotide, the capture oligomer, and the secondary capture reagent; and isolating the complex from the composition, thereby capturing the target polynucleotide.

Embodiment 59 is a method of capturing a target polynucleotide from a composition, the method comprising:

contacting the composition with the combination of any one of embodiments 28-30 or 34-51, wherein the target-hybridizing sequence of the capture oligomer anneals to the target polynucleotide at a site comprising the 3' end of the target polynucleotide;

extending the 3' end of the target polynucleotide with a DNA polymerase with strand-displacement activity, thereby forming a complement of the spacer sequence, which is annealed to the capture oligomer, such that the complementary oligomer is displaced to an extent sufficient for the capture sequence of the capture oligomer to be available for binding; contacting the capture sequence of the capture oligomer with a secondary capture reagent comprising a complement of the capture sequence and (i) a binding partner or (ii) a solid support, thereby forming a complex comprising the target polynucleotide, the capture oligomer, and the secondary capture reagent; and isolating the complex from the composition, thereby capturing the target polynucleotide.

Embodiment 60 is a method of capturing a target polynucleotide from a composition, the method comprising:

contacting the composition with the combination of any one of embodiments 28-30 or 34-51, wherein the target-hybridizing sequence of the capture oligomer anneals to the target polynucleotide at a site comprising the 3' end of the target polynucleotide;

extending the 3' end of the target polynucleotide with a DNA polymerase, which optionally has strand-displacement activity, thereby forming a complement of the spacer sequence, which is annealed to the capture oligomer;

contacting free capture oligomer with the complementary oligomer, wherein the complementary oligomer anneals to the free capture oligomer and partially occupies its capture sequence, wherein the complementary oligomer does not anneal to a complex comprising the capture oligomer annealed to the complement of the spacer sequence;

contacting the capture sequence of capture oligomer complexed with the target polynucleotide with a secondary capture reagent comprising a complement of the capture sequence and (i) a binding partner or (ii) a solid support, thereby forming a complex comprising the target polynucleotide, the capture oligomer, and the secondary capture reagent, wherein the complementary oligomer is introduced into the composition before, during, or after extension of the 3' end of the target polynucleotide; and isolating the complex from the composition, thereby capturing the target polynucleotide.

Embodiment 61 is the method of the immediately preceding embodiment, wherein the target-hybridizing sequence of the capture oligomer undergoes extension, thereby forming an extended capture oligomer.

Embodiment 62 is a method of capturing a target polynucleotide from a composition, the method comprising:

contacting the composition with the combination of any one of embodiments 28-30 or 34-51 which further comprises an amplification oligomer that comprises a reverse target-hybridizing sequence configured to bind the target polynucleotide in an opposite orientation relative to the capture oligomer and optionally further comprises a second adaptor sequence located 5' of the reverse target-hybridizing sequence, wherein the target-hybridizing sequence of the capture oligomer anneals to the target polynucleotide and undergoes extension, thereby forming an extended capture oligomer;

annealing the amplification oligomer to the extended capture oligomer;

extending the 3' end of the amplification oligomer with a DNA polymerase, which optionally has strand-displacement activity, thereby forming a complement of at least the target-hybridizing sequence of the capture oligomer, which is annealed to the capture oligomer;

contacting free capture oligomer with the complementary oligomer, wherein the complementary oligomer anneals to the free capture oligomer and partially occupies its capture sequence, wherein the complementary oligomer does not anneal to a complex comprising the capture oligomer annealed to the complement of the target-hybridizing sequence of the capture oligomer;

contacting the capture sequence of capture oligomer complexed with the target polynucleotide with a secondary capture reagent comprising a complement of the capture sequence and (i) a binding partner or (ii) a solid support, thereby forming a complex comprising the target polynucleotide, the capture oligomer, and the secondary capture reagent, wherein the complementary oligomer is introduced into the composition before, during, or after extension of the 3' end of the target polynucleotide; and isolating the complex from the composition, thereby capturing the target polynucleotide.

Embodiment 63 is a method of capturing a target polynucleotide from a composition, the method comprising:

contacting the target polynucleotide with the capture oligomer or combination of any one of embodiments 1-22, 28-30, or 34-51, wherein the capture oligomer comprises a third or fourth additional sequence 5' of the target hybridizing sequence and 3' of the complement of the capture sequence or the second portion of the spacer sequence;

contacting the target polynucleotide with a second oligomer comprising a second target-hybridizing sequence 5' of a complement of at least a portion of the third or fourth additional sequence, wherein the capture oligomer and the second oligomer form a three-strand junction with the target polynucleotide;

extending the 3' end of the second oligomer with a DNA polymerase with strand-displacement activity, thereby forming a complement of the complement of the capture sequence or a complement of the spacer sequence, which is annealed to the capture oligomer, such that the capture sequence of the capture oligomer is available for binding;

contacting the capture sequence of the capture oligomer with a secondary capture reagent comprising a complement of the capture sequence and (i) a binding partner or (ii) a solid support, thereby forming a complex comprising the target polynucleotide, the capture oligomer, and the secondary capture reagent; and isolating the complex from the composition, thereby capturing the target polynucleotide.

Embodiment 64 is the method of the immediately preceding embodiment wherein the capture oligomer comprises a blocking moiety at its 3' end; and/or wherein the second oligomer comprises a moiety on its 5'-end that blocks displacement by a polymerase with strand displacement activity.

Embodiment 65 is a method of capturing a target polynucleotide from a composition, the method comprising:

contacting the composition with the combination of any one of embodiments 31-51, wherein the target-hybridizing sequence of the capture oligomer anneals to the target polynucleotide; contacting the capture oligomer with the complementary oligomer before or after the capture oligomer anneals to the target polynucleotide, wherein the complementary oligomer anneals to free capture oligomer and partially occupies its capture sequence, wherein the complementary oligomer does not anneal to a complex comprising the capture oligomer annealed to the complement of the target-hybridizing sequence of the capture oligomer and wherein if contacting the capture oligomer with the complementary oligomer occurs before the capture oligomer anneals to the target polynucleotide, then the annealing of the target-hybridizing sequence to the target polynucleotide results in dissociation of the complementary oligomer from the capture oligomer;

contacting the capture sequence of capture oligomer complexed with the target polynucleotide with a secondary capture reagent comprising a complement of the capture sequence and (i) a binding partner or (ii) a solid support, thereby forming a complex comprising the target polynucleotide, the capture oligomer, and the secondary capture reagent; and isolating the complex from the composition, thereby capturing the target polynucleotide.

Embodiment 66 is the method of any one of embodiments 58-65, wherein the secondary capture reagent comprises a binding partner (e.g., biotin) and isolating comprises contacting the complex with a solid support (e.g., beads) comprising a second binding partner (e.g., streptavidin) configured to bind the binding partner of the secondary capture reagent.

Embodiment 67 is the method of any one of embodiments 58-66, wherein the capture oligomer is provided in excess relative to the secondary capture reagent.

Embodiment 68 is the method of any one of embodiments 58-67, wherein the target polynucleotide is obtained from a clinical specimen.

Embodiment 69 is the method of any one of embodiments 58-68, wherein the target polynucleotide is from a pathogen (bacterium, virus, etc.).

Embodiment 70 is the method of any one of embodiments 58-69, wherein the target polynucleotide is an amplification product Embodiment 71 is the method of any one of embodiments 58-70, wherein the target polynucleotide is a member of a sequencing library.

Embodiment 72 is the method of any one of embodiments 58-71, wherein the capture oligomer comprises a third or fourth additional sequence between the target hybridizing sequence and the internal extension blocker.

Embodiment 73 is the method of any one of embodiments 63-72, wherein an extension product is formed by extending the capture oligomer along the target polynucleotide and the method further comprises contacting the extension product with a blocker oligomer comprising the third or fourth additional sequence, which is non-extendable, optionally wherein the blocker oligomer is configured to bind the complement of the third or fourth additional sequence with a greater affinity than the third or fourth additional sequence of the capture oligomer or to form a complex with the complement of the third or fourth additional sequence having a higher melting temperature than a complex of the third or fourth additional sequence of the capture oligomer and the complement of the third or fourth additional sequence.

Embodiment 74 is the method of any one of embodiments 58-73, wherein the method further comprises:

contacting the target polynucleotide with an amplification oligomer, the amplification oligomer comprising (i) a reverse target hybridizing sequence that binds the target polynucleotide in a reverse orientation relative to the capture oligomer and (ii) an additional sequence located 5' of the second target hybridizing sequence, and extending the amplification oligomer along the target polynucleotide to form a reverse extension product, wherein a portion of the capture oligomer anneals to the reverse extension product.

Embodiment 75 is the method of the immediately preceding embodiment, wherein the capture oligomer comprises a blocking moiety at its 3' end.

Embodiment 76 is the method of the immediately preceding embodiment, wherein the method further comprises isolating a complex comprising the reverse extension product annealed to the capture oligomer in which the extension product is substantially single-stranded 5' of the target-hybridizing sequence of the capture oligomer.

Embodiment 77 is the method of any one of embodiments 74-76, wherein the capture oligomer is extendable and the method further comprises extending a portion of the capture oligomer along the extension product, thereby forming a second extension product which comprises the third or fourth additional sequence and a complement of the additional sequence of the amplification oligomer.

Embodiment 78 is the method of any one of embodiments 58-77, wherein the target polynucleotide comprises a sequence from a DNA or RNA of a target organism and an additional sequence not present in the DNA or RNA of the target organism, and the target hybridizing sequence of the capture oligomer is configured to anneal to the additional sequence of the target polynucleotide.

Embodiment 79 is the method of embodiment 78, wherein the composition comprises a plurality of target polynucleotides comprising (i) the additional sequence and (ii) different sequences from the DNA or RNA of the target organism and/or different samples, and the method comprises capturing the plurality of target polynucleotides.

Embodiment 80 is the method of any one of embodiments 58-79, wherein the capture oligomer comprises a reversible extension blocker located 5' of the target-hybridizing sequence and the method comprises:

copying or amplifying the target polynucleotide before unblocking the reversible extension blocker;

unblocking the reversible extension blocker; and performing a further round of copying or amplifying the target polynucleotide, optionally wherein only a single cycle of amplification is performed after unblocking the reversible extension blocker before capturing the target polynucleotide.

Embodiment 81 is the method of any one of embodiments 58-64 or 66-80, wherein the capture oligomer comprises a mixed-nucleotide segment between the internal extension blocker and the first portion of the spacer sequence or the complement of the capture sequence, and the method comprises extending the 3' end of the target polynucleotide along the capture oligomer up to the internal extension blocker, thereby forming an extension product comprising a complement of the mixed-nucleotide segment at its 3' end;

contacting the extension product with a splint oligonucleotide comprising, in the 5' to 3' direction:

a complement of a 5' terminal segment of the extension product;

the mixed-nucleotide segment;

a complement of the capture sequence; and optionally, a segment complementary to a segment in the extension product immediately 5' of the capture sequence; and ligating the 5' end of the extension product to the 3' end of the extension product.

Embodiment 82 is the method of the immediately preceding embodiment wherein the 5' terminal segment of the extension product is an adaptor sequence.

Embodiment 83 is the method of embodiment 81 or 82, wherein the segment in the extension product immediately 5' of the capture sequence is a complement of an adaptor sequence.

Embodiment 84 is the method of any one of embodiments 81-83, wherein the mixed-nucleotide segment comprises 5 nucleotides in which each nucleotide differs from its nearest neighbors.

Embodiment 85 is the method of any one of embodiments 81-84, wherein the mixed-nucleotide segment is free of repeating dinucleotides, repeating trinucleotides, and/or adjacent repeats.

Embodiment 86 is the method of any one of embodiments 58-85, further comprising sequencing the target polynucleotide.

Embodiment 87 is the method of any one of embodiments 58-86, further comprising performing clonal amplification of the captured target polynucleotide Embodiment 88 is the method of the immediately preceding embodiment, further comprising sequencing the clonally amplified target polynucleotide Embodiment 89 is the method of any one of embodiments 86 or 88, wherein the sequencing is Sanger sequencing or next-generation sequencing, optionally wherein the next-generation sequencing comprises sequencing by synthesis, sequencing by ligation, sequencing by hybridization or single-molecule sequencing.

Embodiment 90 is a method of capturing a target polynucleotide from a composition, the method comprising:

contacting the target polynucleotide with the capture oligomer or combination of any one of embodiments 1-22, 28-30, or 34-51, wherein the target-hybridizing sequence of the capture oligomer anneals to the target polynucleotide at a site upstream of the 3' end of the target polynucleotide;

extending the 3' end of the capture oligomer along the target polynucleotide, thereby forming a first extended strand;

contacting the target polynucleotide with a displacer oligomer comprising a displacer target-hybridizing sequence that anneals to the target polynucleotide downstream of the target-hybridizing sequence of the capture oligomer;

extending the displacer oligomer along the target polynucleotide, thereby displacing the first extended strand of the target polynucleotide, optionally wherein the capture oligomer and the displacer are added to the composition simultaneously or sequentially.

Embodiment 91 is the method of the immediately preceding embodiment, further comprising contacting the first extended strand with a reverse amplification oligomer comprising a reverse target-hybridizing sequence configured to bind the first extended strand and extending the reverse amplification oligomer, thereby forming a second extended strand.

Embodiment 92 is the method of the immediately preceding embodiment, wherein the reverse amplification oligomer comprises an additional sequence 5' of its target-hybridizing sequence, optionally wherein the 3' end of the first extended strand is further extended, thereby forming a complement of the additional sequence of the reverse amplification oligomer.

Embodiment 93 is the method of any one of embodiments 90-92, wherein the capture oligomer further comprises an additional sequence located 5' of the target-hybridizing sequence, optionally wherein extension of the second extended strand, if present, forms a complement of the additional sequence of the capture oligomer.

Embodiment 94 is the method of the immediately preceding embodiment, wherein the second strand of the target polynucleotide comprises a complement of the additional sequence of the capture oligomer.

Embodiment 95 is the method of embodiment 90 or 91, wherein the target polynucleotide comprises a sequence from a DNA or RNA of a target organism and an additional sequence not present in the DNA or RNA of the target organism, and the target hybridizing sequence of the capture oligomer is configured to anneal to a first part of the additional sequence of the target polynucleotide and the displacer oligonucleotide is configured to anneal to a second part of the additional sequence of the target polynucleotide, optionally wherein the additional sequence of the target polynucleotide further comprises one or more nucleotides between the first part and the second part.

Embodiment 96 is the method of embodiment 90 or 95, wherein the first extended strand comprises a second additional sequence located proximal to a sequence from a DNA or RNA of a target organism and distal to the target-hybridizing sequence of the capture oligomer, and the method further comprises contacting the first extended strand with a reverse amplification oligomer comprising a reverse target-hybridizing sequence configured to bind the second additional sequence and extending the reverse amplification oligomer, thereby forming a second extended strand, optionally wherein the reverse amplification oligomer comprises an additional sequence 5' of its target hybridizing sequence and the method further comprises further extending the first extended strand along the reverse amplification oligomer.

Embodiment 97 is a combination of oligomers comprising a capture oligomer and a secondary capture reagent, wherein the capture oligomer comprises, in the 5' to 3' direction:

a first self-complementary sequence, a target-hybridizing sequence, and a second self-complementary sequence, wherein the first and second self-complementary sequences are configured to anneal to each other when the target-hybridizing sequence is single stranded and not when the target-hybridizing sequence is annealed to its target;

the secondary capture reagent comprises a complement of the first or second self-complementary sequence and a binding partner; and the capture oligomer is present in the combination in a greater amount than the secondary capture reagent.

Embodiment 98 is the combination of the immediately preceding embodiment, wherein the capture oligomer has the formula:

5'-SC1-THS2-THS1-L-THS2'-SC2-X-3' or

5'-SC2-THS2'-L-THS1-THS2-SC1-X-3' wherein SC1 is the first self-complementary sequence,

THS2 and THS1 are second and first portions of the target-hybridizing sequence, respectively, L is an optionally present linker, THS2' is an optionally present complement of the second portion of the target-hybridizing sequence, SC2 is the second self-complementary sequence, and X is an optionally present blocking moiety.

Embodiment 99 is the combination of any one of embodiments 97 or 98, wherein the capture oligomer comprises a linker located 3' of the first portion of the target-hybridizing sequence and 5' of the second self-complementary sequence.

Embodiment 100 is the combination of any one of embodiments 97-99, wherein the capture oligomer comprises a complement of the second portion of the target-hybridizing sequence located 3' of the first portion of the target-hybridizing sequence and 5' of the second self-complementary sequence.

Embodiment 101 is the combination of any one of embodiments 97-100, wherein the capture oligomer comprises a linker located 3' of the first portion of the target-hybridizing sequence and a complement of the second portion of the target-hybridizing sequence located 3' of the linker and 5' of the second self-complementary sequence.

Embodiment 102 is the combination of any one of embodiments 97-101, wherein the capture oligomer comprises a linker located 5' of the first portion of the target-hybridizing sequence and 3' of the second self-complementary sequence.

Embodiment 103 is the combination of any one of embodiments 97-102, wherein the capture oligomer comprises a complement of the second portion of the target-hybridizing sequence located 5' of the first portion of the target-hybridizing sequence and 3' of the second self-complementary sequence.

Embodiment 104 is the combination of any one of embodiments 97-103, wherein the capture oligomer comprises a linker located 5' of the first portion of the target-hybridizing sequence and a complement of the second portion of the target-hybridizing sequence located 5' of the linker and 3' of the second self-complementary sequence.

Embodiment 105 is the combination of any one of embodiments 97-104, wherein the capture oligomer and/or secondary capture reagent is nonextendable Embodiment 106 is the combination of any one of embodiments 97-105, wherein the first or second self-complementary sequence comprises poly A or poly T and the complement of the self-complementary sequence comprises poly T or poly A.

Embodiment 107 is the combination of any one of embodiments 97-106, wherein the capture oligomer comprises one or more affinity-enhancing modifications (e.g., any one or more of 5-Me-C, 2-aminopurine, 2'-fluoro, C-5-propyne, LNA, PNA, ZNA, phosphorothioate, 2'-OMe, or constrained ethyl (cEt) substitutions), e.g., in the target-hybridizing sequence.

Embodiment 108 is a kit comprising the combination or capture oligomer of any one of embodiments 1-22, 28-51, 54-57, or 97-107.

Embodiment 109 is a composition comprising the combination or capture oligomer of any one of embodiments 1-22, 28-51, 54-57, or 97-107.

Embodiment 110 is the combination of any one of embodiments 18-22, 28-51, 54-57, or 97-107, comprising (i) a secondary capture reagent that comprises a binding partner and (ii) a solid support (e.g., one or more beads) comprising a second binding partner configured to bind the binding partner of the secondary capture reagent, optionally wherein the binding partner of the secondary capture reagent is biotin and the second binding partner is a biotin-binding agent (e.g., streptavidin).

Embodiment 111 is a reaction mixture comprising the combination of any one of embodiments 18-22, 28-51, 54-57, 97-107, or 110, and further comprising a target polynucleotide.

Embodiment 112 is the reaction mixture of the immediately preceding embodiment, wherein the target is in or is obtained from an extract from a cell, specimen, virus, or biological sample.

Embodiment 113 is a method of capturing a target polynucleotide from a composition, the method comprising:

contacting the target polynucleotide with the combination of any one of embodiments 97-107 or 110, wherein the capture oligomer and the secondary capture reagent are added simultaneously or sequentially, and wherein the target-hybridizing sequence of the capture oligomer anneals to the target polynucleotide and the secondary capture reagent anneals to a self-complementary sequence of the capture oligomer, thereby forming a complex;

contacting the complex with a second binding partner configured to bind the binding partner of the secondary capture reagent, wherein the second binding partner is associated with a solid support, wherein the second binding partner binds the binding partner of the secondary capture reagent; and isolating the complex from the composition, thereby capturing the target polynucleotide.

Embodiment 114 is the method of the immediately preceding embodiment wherein the capture oligomer is in excess relative to the target polynucleotide Embodiment 115 is the method of any one of embodiments 113 or 114, wherein the target polynucleotide is in excess relative to the secondary capture reagent Embodiment 116 is the method of any one of embodiments 113-115, wherein only a fraction of the target polynucleotide is captured.

Embodiment 117 is the method of any one of embodiments 113-116, wherein the target polynucleotide is obtained from a clinical specimen.

Embodiment 118 is the method of any one of embodiments 113-117, the target polynucleotide is from a pathogen (bacterium, virus, etc.).

Embodiment 119 is the method of any one of embodiments 113-118, wherein the target polynucleotide is an amplification product.

Embodiment 120 is the method of any one of embodiments 113-119, further comprising amplifying the target polynucleotide and/or attaching one or more additional sequences to the target polynucleotide.

Embodiment 121 is the method of any one of embodiments 113-120, further comprising preparing a sequencing library comprising the target polynucleotide.

Embodiment 122 is the method of any one of embodiments 113-121, further comprising one or both of clonally amplifying members of the sequencing library and sequencing members of the sequencing library, optionally wherein the sequencing is Sanger sequencing or next-generation sequencing, optionally wherein the next-generation sequencing comprises sequencing by synthesis, sequencing by ligation, sequencing by hybridization or single-molecule sequencing.

Embodiment 123 is a method of capturing a target polynucleotide from a composition, the method comprising:

contacting the target polynucleotide with a capture oligomer comprising, in the 5' to 3' direction:

a capture sequence, an optional internal extension blocker, an optional spacer sequence, and a target hybridizing sequence that is configured to anneal to the target polynucleotide; contacting the capture oligomer with a first capture reagent comprising a complement of the capture sequence (before, while, or after contacting the target polynucleotide with the capture oligomer);

providing a second capture reagent comprising a complement of a sequence in the capture oligomer other than the capture sequence, wherein if some or all of the capture oligomer is not annealed to the target polynucleotide, the second capture reagent contacts the capture oligomer that is not annealed to the target polynucleotide;

isolating first and second complexes from the composition, wherein the first complex comprises the target polynucleotide and the second complex comprises capture oligomer not annealed to the target polynucleotide; and selectively eluting the target polynucleotide or a subcomplex comprising the target polynucleotide from the first complex;

optionally wherein (a) the first capture reagent comprises (i) a binding partner and (e.g., biotin) or (ii) a solid support (e.g., bead or surface) and/or (b) the second capture reagent comprises (i) a binding partner and (e.g., biotin) or (ii) a solid support (e.g., bead or surface).

Embodiment 124 is the method of embodiment 123, wherein the target polynucleotide is contacted with an excess amount of the capture oligomer.

Embodiment 125 is the method of embodiment 123 or 124, wherein the first capture reagent is provided in a limiting amount relative to the capture oligomer.

Embodiment 126 is the method of any one of embodiments 123-125, wherein the capture oligomer is provided in a limiting amount relative to the target polynucleotide.

Embodiment 127 is the method of any one of embodiments 123-126, wherein the fraction of the capture oligomer contacted with the second capture reagent comprises capture oligomer not annealed to the target polynucleotide.

Embodiment 128 is the method of any one of embodiments 123-127, wherein the first capture reagent comprises a first solid support that comprises a complement of the capture sequence.

Embodiment 129 is the method of any one of embodiments 123-128, wherein the second capture reagent comprises a second solid support that comprises the complement of the sequence in the capture oligomer other than the capture sequence.

Embodiment 130 is the method of any one of embodiments 123-129, wherein the capture oligomer comprises a spacer sequence between the target hybridizing sequence and the internal extension blocker, optionally wherein the second capture reagent comprises a complement of the spacer sequence.

Embodiment 131 is the method of any one of embodiments 123-130, wherein the target hybridizing sequence anneals to the target polynucleotide at the 3' end of the target polynucleotide.

Embodiment 132 is the method of the immediately preceding embodiment wherein the method comprises extending the 3' end of the target polynucleotide.

Embodiment 133 is the method of any one of embodiments 123-132, wherein the second capture reagent has a greater affinity for the capture oligomer than the affinity of the first capture reagent for the capture oligomer and/or the second capture reagent is configured to form a complex with the capture oligomer having a greater melting temperature than a complex of the first capture reagent and the capture oligomer.

Embodiment 134 is the method of any one of embodiments 128-133, comprising:

contacting the target polynucleotide with a capture oligomer comprising, in the 5' to 3' direction:

a first capture sequence, an internal extension blocker, a second capture sequence, and a target hybridizing sequence that is configured to anneal to the 3' end of the target polynucleotide, thereby annealing the capture oligomer to the target polynucleotide;

extending the 3' end of the target polynucleotide through the second capture sequence; contacting the first complex with a first solid support, which comprises a complement of the first capture sequence, thereby forming a first complex;

contacting unbound capture oligomer with a second solid support, which comprises a complement of the second capture sequence, thereby forming a second complex, wherein the complement of the first capture sequence has a lower melting temperature than a second complex formed by annealing of the second capture sequence and the complement of the second capture sequence, and/or the complement of the second capture sequence has an affinity for the second capture sequence which is greater than the affinity of the complement of the first capture sequence for the first capture sequence;

isolating the first and second complexes from material not bound to the first or second solid supports; and selectively eluting the target polynucleotide from the first complex.

Embodiment 135 is the method of embodiment 123, wherein the first capture reagent further comprises a second capture sequence which is not complementary to the capture oligomer or the target polynucleotide, and the method comprises, after contacting the annealed capture oligomer with the first capture reagent, annealing the second capture sequence to a solid support comprising a complement of the second capture sequence.

Embodiment 136 is the method of embodiment 123 or 135, wherein the second capture reagent further comprises a third capture sequence which is not complementary to the capture oligomer or the target polynucleotide, and the method comprises, after contacting unbound capture oligomer with the second capture reagent, annealing the third capture sequence to a solid support comprising a complement of the third capture sequence.

Embodiment 137 is the method of embodiment 123, wherein the first capture reagent further comprises a second capture sequence which is not complementary to the capture oligomer or the target polynucleotide, and the method comprises, after contacting the annealed capture oligomer with the first capture reagent, annealing the second capture sequence to a solid support comprising a complement of the second capture sequence; and the affinity of the complement of the third capture sequence for the third capture sequence is greater than the affinity of the complement of the second capture sequence for the second capture sequence, and/or the complement of the third capture sequence is configured to form a complex with the third capture sequence having a greater melting temperature than a complex of the complement of the second capture sequence and the second capture sequence.

Embodiment 138 is a combination comprising a capture oligomer, a first solid support, and a second solid support, wherein:

the capture oligomer comprises, in the 5' to 3' direction:
a first capture sequence,
an optional internal extension blocker,
an optional second capture sequence, and
a target hybridizing sequence;
the first solid support comprises a complement of the first capture sequence;
the second solid support comprises a complement of the second capture sequence; and
a first complex formed by annealing of the first capture sequence and the complement of the first capture sequence has a lower melting temperature than a second complex formed by annealing of the second capture sequence and the complement of the second capture sequence, and/or the complement of the second capture sequence has an affinity for the second capture sequence which is greater than the affinity of the complement of the first capture sequence for the first capture sequence.

Embodiment 139 is a combination comprising a capture oligomer, a first capture reagent, a second capture reagent, a first solid support, and a second solid support, wherein:

the capture oligomer comprises, in the 5' to 3' direction:
a first capture sequence,
an optional internal extension blocker, and
a target hybridizing sequence;
the first capture reagent comprises a second capture sequence and a complement of the first capture sequence, wherein the second capture sequence is not complementary to the capture oligomer;
the second capture reagent comprises a third capture sequence and a complement of a sequence of the capture oligomer other than the first capture sequence, wherein the third capture sequence is not complementary to the capture oligomer;
the first solid support comprises a complement of the second capture sequence;
the second solid support comprises a complement of the third capture sequence; and
a first complex formed by annealing of the second capture sequence and the complement of the second capture sequence has a lower melting temperature than a second complex formed by annealing of the third capture sequence and the complement of the third capture sequence, and/or the complement of the third capture sequence has an affinity for the third capture sequence which is greater than the affinity of the complement of the second capture sequence for the second capture sequence.

Embodiment 140 is a combination comprising a capture oligomer and a secondary capture reagent, wherein the capture oligomer comprises:

a target-hybridizing sequence comprising one or more affinity-enhancing nucleotides; and a capture sequence; and
the secondary capture reagent comprises a complement of the capture sequence and a binding partner.

Embodiment 141 is the combination of any one of embodiments 138-140, wherein the capture sequence is located 5' to the target-hybridizing sequence.

Embodiment 142 is the combination of any one of embodiments 138-141, wherein the target-hybridizing sequence is configured to anneal to an additional sequence.

Embodiment 143 is the combination of any one of embodiments 138-142, wherein the secondary capture reagent is present in the combination in a lower amount than the capture oligomer.

Embodiment 144 is the combination of any one of embodiments 138-144, wherein the capture oligomer comprises one or more affinity-enhancing modifications (e.g., any one or more of 5-Me-C, 2-aminopurine, 2'-fluoro, C-5-propyne, LNA, PNA, ZNA, phosphorothioate, 2'-OMe, or constrained ethyl (cEt) substitutions), e.g., in the target-hybridizing sequence.

Embodiment 145 is the combination of any one of embodiments 138-145, wherein the capture sequence comprises a poly A or poly T sequence.

Embodiment 146 is a method of capturing a target polynucleotide from a composition, the method comprising:

contacting the target polynucleotide with the combination of any one of embodiments 138-145, wherein the capture oligomer and the secondary capture reagent are added simultaneously or sequentially, and wherein the target-hybridizing sequence of the capture oligomer anneals to the target polynucleotide and the secondary capture reagent anneals to the capture sequence of the capture oligomer, thereby forming a complex;
contacting the complex with a second binding partner configured to bind the binding partner of the secondary capture reagent, wherein the second binding partner is associated with a solid support, and the second binding partner binds the binding partner of the secondary capture reagent; and
isolating the complex from the composition, thereby capturing the target polynucleotide.

Embodiment 147 is the method of the immediately preceding embodiment wherein the secondary capture reagent is provided in a lower amount than the capture oligomer and/or the target polynucleotide.

Embodiment 148 is the method of embodiment 146 or 147, wherein the capture oligomer is provided in a lower amount than the target polynucleotide, optionally wherein the secondary capture reagent is provided in a lower amount than the capture oligomer.

Embodiment 149 is the method of any one of embodiments 146-148, wherein the target polynucleotide comprises an additional sequence and the target-hybridizing sequence anneals to the additional sequence.

Embodiment 150 is the method of any one of embodiments 146-149, wherein the target-hybridizing sequence of the capture oligomer comprises affinity-enhancing modifications (e.g., any one or more of 5-Me-C, 2-aminopurine, 2'-fluoro, C-5-propyne, LNA, PNA, ZNA, phosphorothioate, 2'-OMe, or constrained ethyl (cEt) substitutions).

Embodiment 151 is the method of any one of embodiments 146-150, wherein the target polynucleotide comprises a sequence from a DNA or RNA of a target organism, and the additional sequence is not present in the DNA or RNA of the target organism.

Embodiment 152 is the method of any one of embodiments 58-96, 113-137, or 146-151, wherein an amount of target polynucleotide is captured that is less than or equal to a predetermined amount, optionally wherein the predetermined amount corresponds to the molar quantity of capture oligomer provided or the molar quantity of secondary capture reagent provided.

Embodiment 153 is the method of any one of embodiments 58-96, 113-137, or 146-152, wherein the capture oligomer is present in an amount in the range of $10^7$ to $10^{13}$ molecules/reaction, $10^9$ to $10^{12}$ molecules/reaction, or $10^{10}$ to $10^{12}$ molecules/reaction.

Embodiment 154 is the method of any one of embodiments 58-96, 113-137, or 146-153, wherein the secondary capture reagent, if present, is present in the range of $10^3$ to $10^{14}$ molecules/reaction, or $10^3$ to $10^9$ molecules/reaction, or $10^5$ to $10^{13}$ molecules/reaction, or $10^5$ to $10^8$ molecules/reaction, or $10^6$ to $10^{13}$ molecules/reaction, or $10^6$ to $10^8$ molecules/reaction.

Embodiment 155 is the method of any one of embodiments 58-96, 113-137, or 146-154, wherein the blocker oligomer, if present, is present in the range of $10^8$ to $10^{14}$ molecules/reaction, $10^{10}$ to $10^{13}$ molecules/reaction, or $10^{11}$ to $10^{13}$ molecules/reaction; and wherein the second oligomer, if present, is present in the range of $10^7$ to $10^{14}$ molecules/reaction or $10^8$ to $10^{13}$ molecules/reaction.

Embodiment 156 is the method of any one of embodiments 58-96, 113-137, or 146-155, wherein the complementary oligomer, if present, is present in the range of about $1.5 \times 10^7$ to $10^{14}$ molecules/reaction or about $1.5 \times 10^9$ to $10^{13}$ molecules/reaction; and wherein the splint oligomer, if present, is present in the range of $10^3$ to $10^{14}$ molecules/reaction, or $10^4$ to $10^{10}$ molecules/reaction, or $2 \times 10^5$ to $10^{14}$ molecules/reaction, or $10^6$ to $10^9$ molecules/reaction, or $2 \times 10^6$ to $10^{14}$ molecules/reaction, or $2 \times 10^6$ to $10^9$ molecules/reaction.

Embodiment 157 is the method of any one of embodiments 58-96, 113-137, or 146-156, wherein the amplification oligomer, if present, is present in the range of about $10^7$ to $10^{14}$ molecules/reaction or about $10^8$ to $10^{13}$ molecules/reaction; and wherein the blocker oligomer, if present, is present in the range of $10^8$ to $10^{14}$ molecules/reaction, $10^{10}$ to $10^{13}$ molecules/reaction, or $10^{11}$ to $10^{13}$ molecules/reaction.

Embodiment 158 is the method of any one of embodiments 58-96, 113-137, or 146-157, wherein the displacer oligomer, if present, is present in the range of about $10^7$ to $10^{14}$ molecules/reaction or about $10^8$ to $10^{13}$ molecules/reaction.

Embodiment 159 is the capture oligomer, combination, reaction mixture, kit, composition, or method of any one of the preceding embodiments, wherein, if present in the capture oligomer, the length of the first additional sequence (optionally a stabilizing sequence) is about 2-15 nucleotides or about 3-10 nucleotides.

Embodiment 160 is the capture oligomer, combination, reaction mixture, kit, composition, or method of any one of the preceding embodiments, wherein the length of the capture sequence is about 10-35 nucleotides or about 10-25 nucleotides.

Embodiment 161 is the capture oligomer, combination, reaction mixture, kit, composition, or method of any one of the preceding embodiments, wherein the length of the linker, if present, is about 10-20 nucleotides or about 3-20 or more atoms or about 2-15 or more repeating units if non-nucleotide-based.

Embodiment 162 is the capture oligomer, combination, reaction mixture, kit, composition, or method of any one of the preceding embodiments, wherein the length of the internal extension blocker, if present, is about 1-20 nucleotides, or about 1-8 nucleotides or about 3-20 or more atoms or about 1-8 or more repeating units if non-nucleotide-based.

Embodiment 163 is the capture oligomer, combination, reaction mixture, kit, composition, or method of any one of the preceding embodiments, wherein the length of the second additional sequence (optionally a mixed nucleotide sequence), if present, is about 2-10 nucleotides or about 4-8 nucleotides.

Embodiment 164 is the capture oligomer, combination, reaction mixture, kit, composition, or method of any one of the preceding embodiments, wherein the length of the complement of the capture sequence is about 10-35 nucleotides or about 10-25 nucleotides.

Embodiment 165 is the capture oligomer, combination, reaction mixture, kit, composition, or method of any one of the preceding embodiments, wherein the length of the third additional sequence (optionally a stabilizing sequence and/or an adaptor sequence), if present, is about 2-50 nucleotides or about 4-35 nucleotides. the length of the reversible extension blocker is about 1-20 or about 1-8 nucleotides (natural or non-natural).

Embodiment 166 is the capture oligomer, combination, reaction mixture, kit, composition, or method of any one of the preceding embodiments, wherein the length of the fourth additional sequence (optionally an adaptor sequence), if present, is about 4-40 nucleotides or about 6-25 nucleotides.

Embodiment 167 is the capture oligomer, combination, reaction mixture, kit, composition, or method of any one of the preceding embodiments, wherein the length of the target hybridizing sequence is about 10-60 nucleotides or about 12-25 nucleotides.

Embodiment 168 is the capture oligomer, combination, reaction mixture, kit, composition, or method of any one of the preceding embodiments, wherein the length of the blocking moiety, if present, is about 1-10 or about 1-5 nucleotides, or about 3-20 atoms or about 1-5 repeating units if non-nucleotide-based.

Embodiment 169 is the capture oligomer, combination, reaction mixture, kit, composition, or method of any one of the preceding embodiments, wherein the overall length of the capture oligomer is about 40-200 nucleotides, or about 40-150 nucleotides, or about 60-140 nucleotides, or about 60-130 nucleotides, optionally wherein the capture oligomer further comprises a non-nucleotide element having a length of about 3-60 atoms or 5-28 repeating units.

Embodiment 170 is the combination, reaction mixture, kit, composition, or method of any one of embodiments 18-169, wherein the secondary capture reagent, if present, comprises a complement of the capture sequence having a length of about 10-35 nucleotides or about 10-20 nucleotides.

Embodiment 171 is the combination, reaction mixture, kit, composition, or method of any one of embodiments 18-170, wherein the length of the blocker oligomer, if present, is about 10-35 nucleotides or about 10-20 nucleotides, optionally wherein the blocker oligomer further comprises a non-nucleotide element having a length of about 3-20 atoms or 1-5 repeating units.

Embodiment 172 is the combination, reaction mixture, kit, composition, or method of any one of embodiments 18-171, wherein the length of the second oligomer is about 15-50 nucleotides or about 20-40 nucleotides.

Embodiment 173 is the combination, reaction mixture, kit, composition, or method of any one of embodiments 18-172, wherein the length of the complementary oligomer, if present, is about 10 to 50 nucleotides or about 15 to 35 nucleotides.

Embodiment 174 is the combination, reaction mixture, kit, composition, or method of any one of embodiments 18-173, wherein the length of the splint oligomer, if present, is about 15 to 60 nucleotides or about 20 to 50 nucleotides.

Embodiment 175 is the combination, reaction mixture, kit, composition, or method of any one of embodiments 18-174, wherein the length of the displacer oligomer, if present, is about 10 to 50 nucleotides or about 20 to 40 nucleotides.

Embodiment 176 is the combination, reaction mixture, kit, composition, or method of any one of embodiments 18-175, wherein the length of the amplification oligomer, if present, is about 10 to 80 nucleotides or about 20 to 60 nucleotides.

II. BRIEF DESCRIPTION OF THE DRAWINGS

FIGS. 1A-1C illustrate an exemplary capture oligomer according to the disclosure, comprising a capture sequence, blocking moiety, complement of the capture sequence (C'), additional sequence (e.g., third or fourth additional sequence), and target-hybridizing sequence, together with other molecules. In FIG. 1A, the capture oligomer is annealed to a target polynucleotide (target), and the 3' end of the target polynucleotide is annealed at the 5' end of the target-hybridizing sequence. The capture sequence is annealed to C'. In FIG. 1B, The 3' end of the target has been extended up to the blocking moiety and the resulting target extension is annealed to the additional sequence and C', while the capture sequence has been displaced and has become single stranded. The 3' end of the capture oligomer has also been extended along the target polynucleotide. In FIG. 1C, the complex of FIG. 1B has annealed to a secondary capture reagent comprising a complement of the capture sequence and a binding partner or solid substrate. Meanwhile, excess capture oligomer remains with the capture sequence annealed to the complement of the capture sequence and does not interact with the secondary capture reagent.

FIG. 2A illustrates an embodiment of the disclosure in which a complex as in FIG. 1B is annealed to a secondary capture reagent comprising a complement of the capture sequence and associated with solid substrate (in this case, a streptavidin-coated magnetic bead). The solid substrate may be part of the secondary capture reagent or may be associated with the secondary capture reagent through interaction with a binding partner (e.g., biotin) of the secondary capture reagent.

Figure 4A:
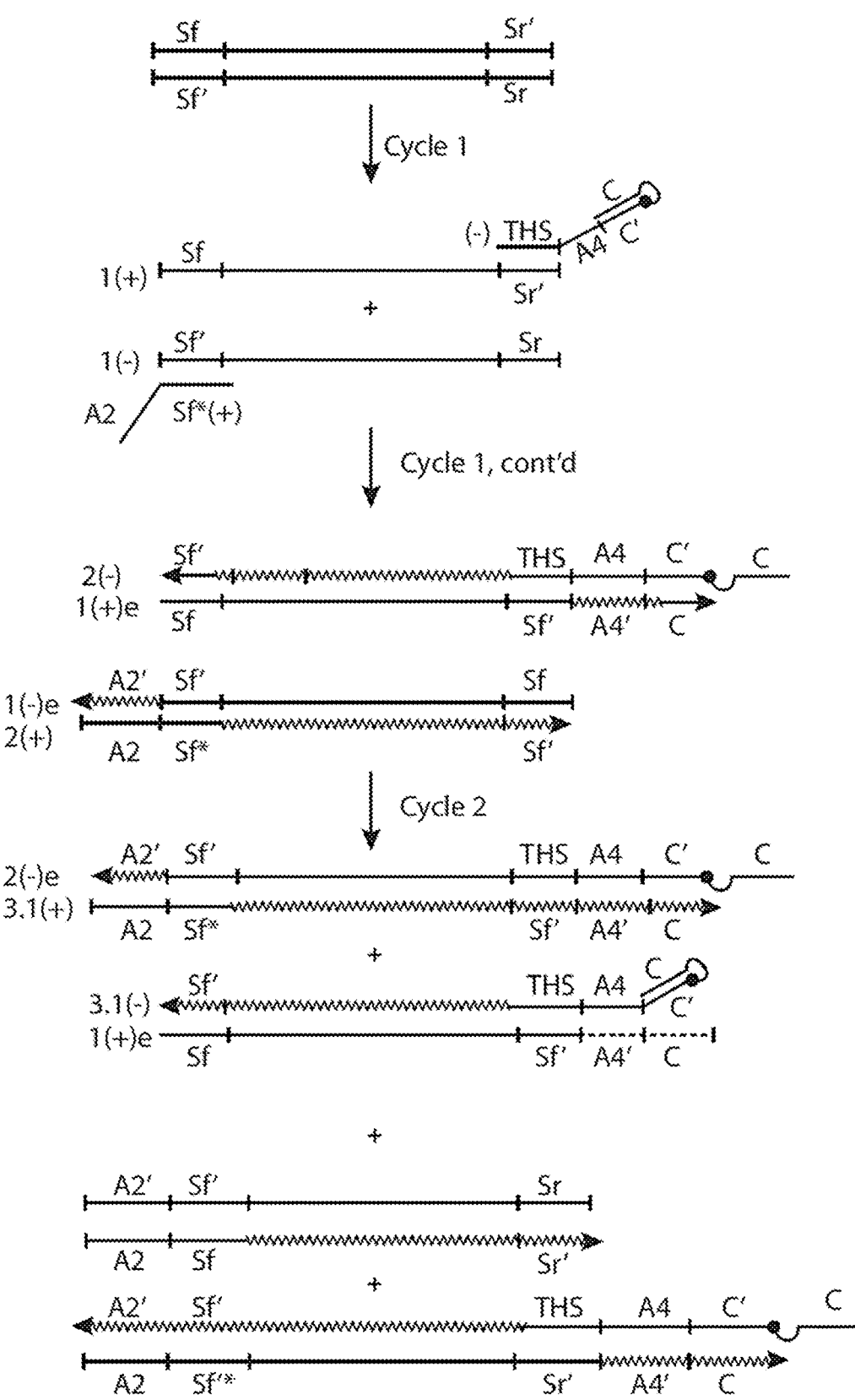

FIG. 4A illustrates exemplary molecules and an exemplary reaction scheme according to the disclosure. A target molecule is provided in which a first strand comprises the sequences Sf at its 5' end and Sr' at its 3' end and a second strand comprises the sequences Sf' at its 3' end and Sr at its 5' end. Here and throughout, a sequence designation with a ' indicates complementarity to the sequence having the designation without the '. The target molecule can be, e.g., an amplicon from a previously performed reaction using primers with the sequences Sf and Sr. A first extension cycle (Cycle 1) is performed, in which a capture oligomer according to the disclosure comprising a capture sequence C, an internal extension blocker (filled circle), a complement of the capture sequence C', a fourth additional sequence A4, and a target-hybridizing sequence THS complementary to Sr' anneals to the first target strand 1(+). A reverse amplification oligomer comprising an additional sequence A2 and a target-hybridizing sequence Sf* complementary to at least Sf anneals to the second target strand 1(−). Sf* may comprise affinity-enhancing modifications and/or additional complementary nucleotides to the second target strand to enhance its affinity to the target and facilitate competition for binding with a primer having the sequence Sf from a previous reaction if present. Extension of the capture oligomer and the reverse amplification oligomer generates products 2(−) and 2(+), respectively, while the first strand is extended along the capture oligomer to generate product 1(+)e and the second strand is extended along the reverse amplification oligomer to generate product 1(−)e. The capture sequence in the extended capture oligomer 2(−) is displaced essentially as described for FIG. 1B. A second reaction cycle (Cycle 2) is performed in which 2(−) anneals to a reverse amplification oligomer, resulting in extension to generate products 2(−)e and 3.1(+). Meanwhile, 1(+)e anneals to a capture oligomer and extension of the latter generates product 3.1(−). Additional instances of 1(−)e and 2(+), and of 2(−)e and 3.1(+), are also generated from the appropriate hybridization and extension events. This reaction scheme illustrates inclusion of additional sequences at each end of a target together with rendering the target captureable by incorporation of C in a form available for binding, for example with a second capture reagent.

Figure 4B:
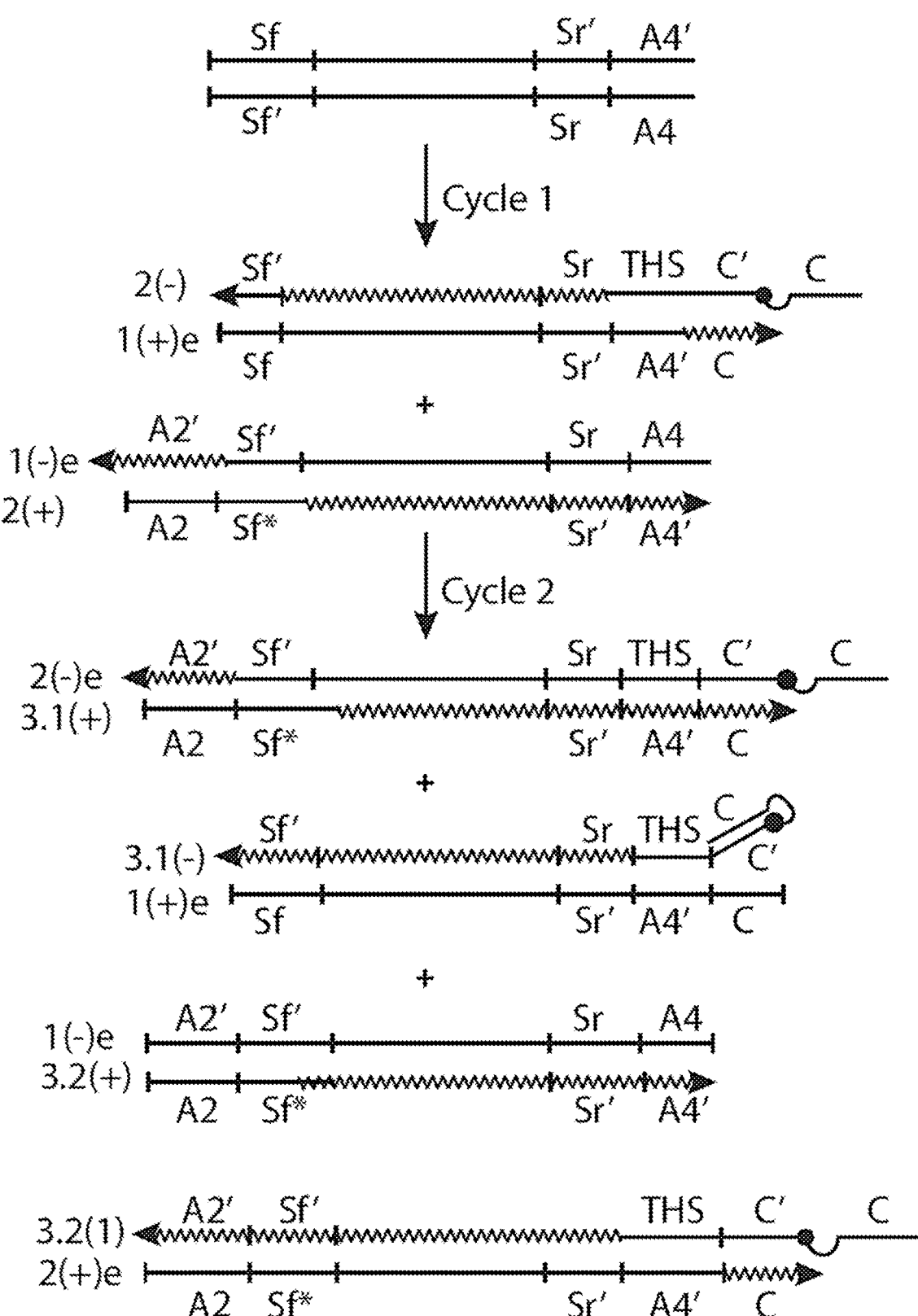

FIG. 4B illustrates exemplary molecules and an exemplary reaction scheme according to the disclosure. A target molecule is provided in which a first strand comprises the sequences Sf at its 5' end and Sr' and A4' at its 3' end and a second strand comprises the sequences Sf' at its 3' end and Sr and A4 at its 5' end. The target molecule can be, e.g., an amplicon from a previously performed reaction using primers with the sequences Sf and A4-Sr, e.g., wherein A4 is an additional sequence not originally present in the template. A first extension cycle (cycle 1) is performed, in which a capture oligomer according to the disclosure comprising a capture sequence C, an internal extension blocker (filled circle), a complement of the capture sequence C', a fourth additional sequence A4, and a target-hybridizing sequence THS complementary to A4' anneals to the first target strand (not shown). A reverse amplification oligomer comprising an additional sequence A2 and a target-hybridizing sequence Sf* complementary to at least Sf anneals to the second target strand (not shown). Sf* may comprise affinity-enhancing modifications and/or additional complementary nucleotides to the second target strand to enhance its affinity to the target and facilitate competition for binding with a primer having the sequence Sf from a previous reaction is present. Extension of these complexes generates an extended capture oligomer 2(–) and an extended first target strand 1(+)e, and an extended second target strand 1(–)e and an extended reverse amplification oligomer 2(+). The capture sequence in the extended capture oligomer 2(–) is displaced essentially as described for FIG. 1B. A second reaction cycle (cycle 2) is performed in which 2(–) anneals to a reverse amplification oligomer, resulting in extension to generate products 2(–)e and 3.1(+). Meanwhile, 1(+)e anneals to a capture oligomer and extension of the latter generates product 3.1(–). Additional instances of 1(–) e and 2(+), and of 2(–)e and 3.1(+), are also generated from the appropriate hybridization and extension events. This reaction scheme illustrates inclusion of an additional sequence at the end of a target distal from the capture oligomer binding site together with rendering the target captureable by incorporation of C (in a form available for binding) using a capture oligomer that can have a universal THS (i.e., that binds the additional sequence A4' that can be attached to the target in a previous step (e.g., via amplification or ligation).

Figure 5:
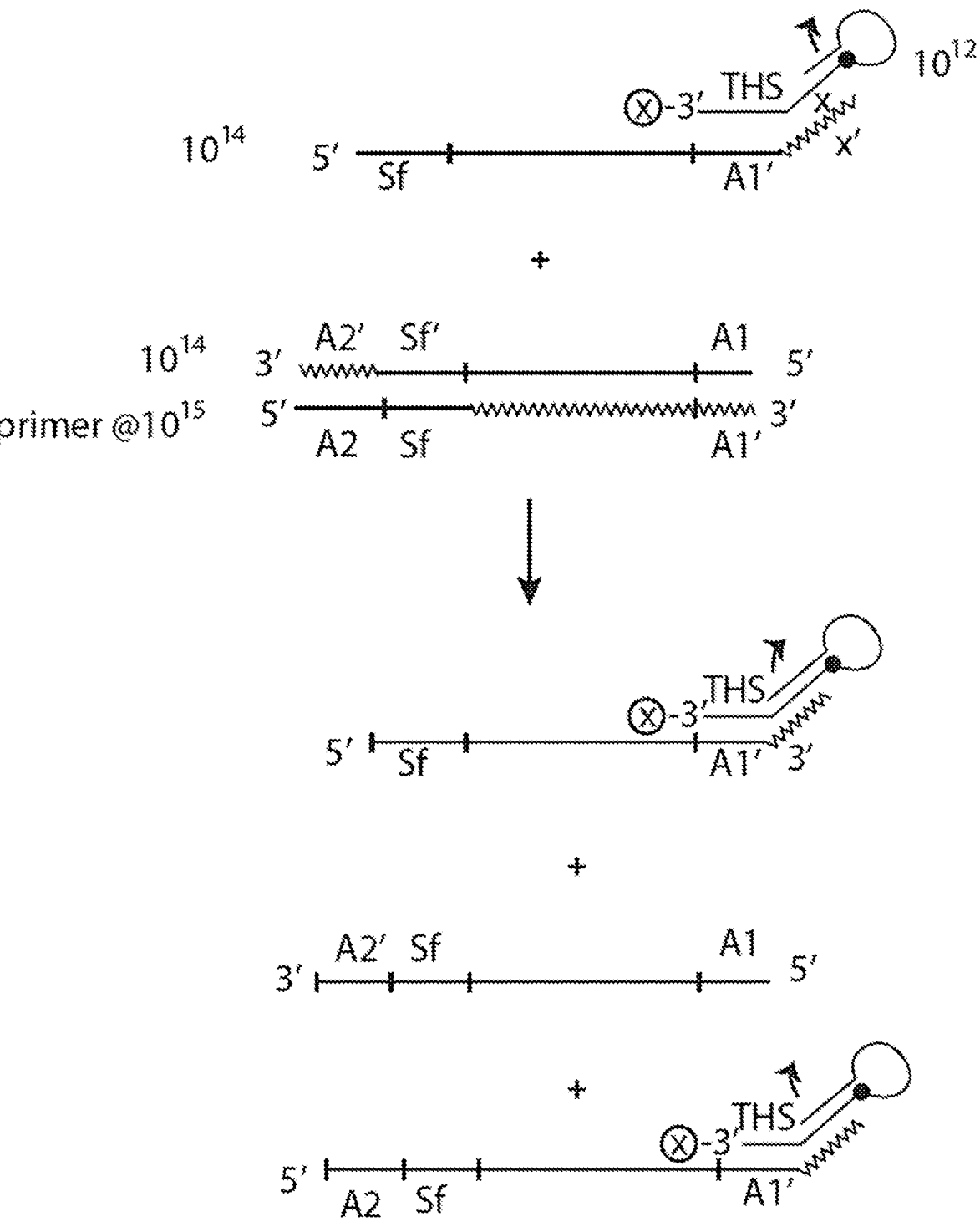

FIG. 5 illustrates exemplary molecules and an exemplary reaction scheme according to the disclosure. A capture oligomer is provided that comprises, among other things, a 3' blocking moiety and a target-hybridizing sequence (THS) that binds sequence A1' in a target strand. A1' may be an additional sequence attached to the target in a previous step (e.g., via amplification or ligation). The capture oligomer further comprises a sequence x that comprises a complement of the capture sequence of the capture oligomer and may also comprise a third or fourth additional sequence between the complement of the capture sequence and THS. The target strand can be extended along the capture oligomer to displace the capture sequence from the complement of the capture sequence, as discussed elsewhere. The capture oligomer may be provided in a limiting amount (e.g., $10^{12}$ copies) relative to the target (e.g., $10^{14}$ copies). A primer is also provided in excess over the target (e.g., $10^{15}$ copies) which comprises the sequences A2 and Sf. Extension of this primer results in a strand comprising A2 at its 5' end and A1' at its 3' end. The target strand is also extended along the primer to include sequence A2'. If a second extension cycle is performed (downward arrow), a mixture of products is formed including those discussed above and a complex of a target strand with a capture oligomer in which the target strand comprises A2 at its 5' end as well as A1' near its 3' end. This reaction scheme illustrates generation of single stranded captureable products, including (when the second extension cycle is performed) one in which additional sequences have been included in the target strand.

Figure 6:
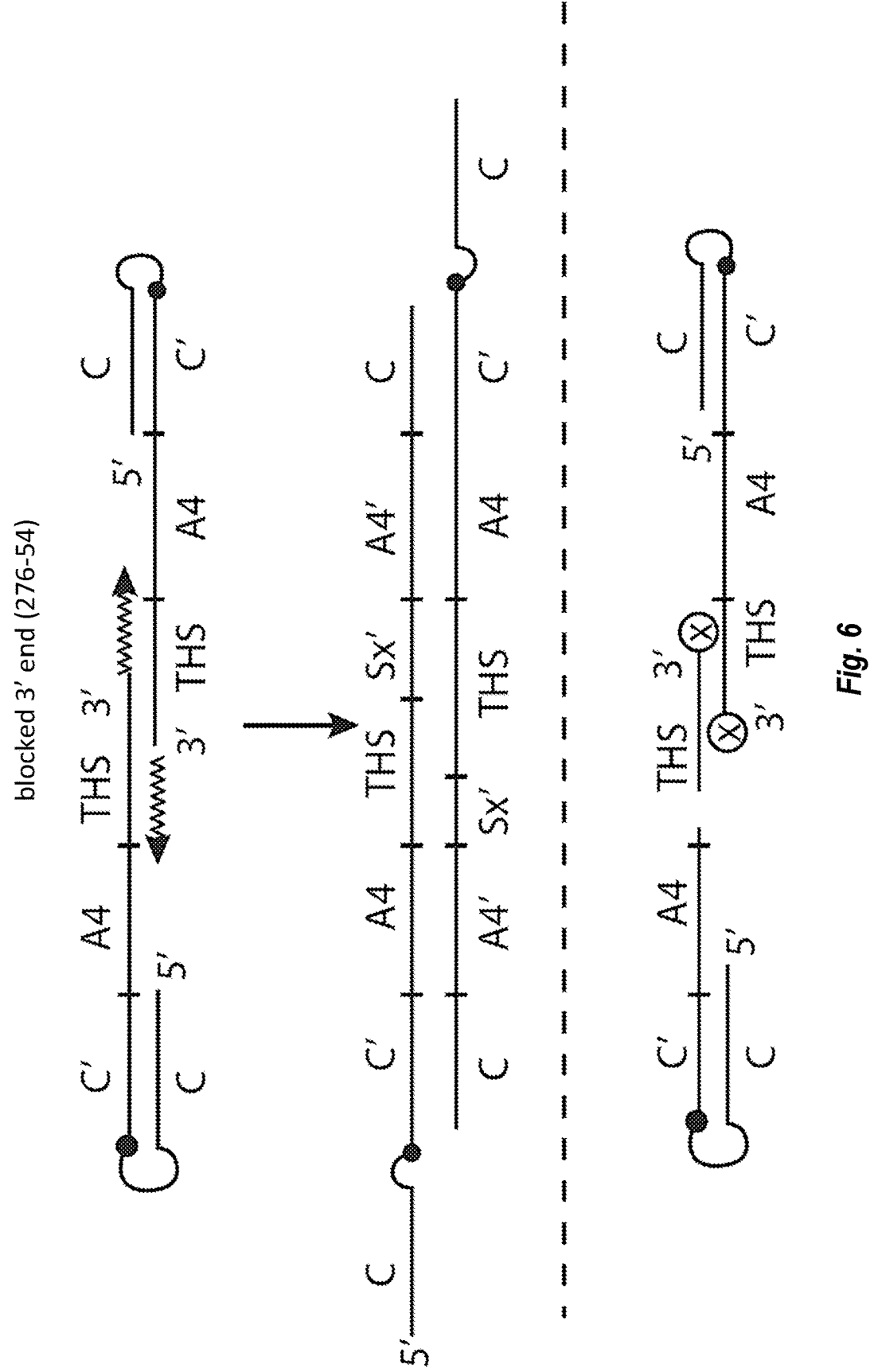

FIG. 6 illustrates (above the dashed line) how hybridization of a capture oligomer with an extendable 3' end to another capture oligomer can, upon extension, produce a dimer in which the capture sequences are displaced from C'. This dimer is now capturable and may interfere with downstream processes, such as competition with capture of the desired target by occupying a secondary capture reagent (not shown), interference is subsequent analysis (e.g., dimers will become part of a sequencing library and thereby diminishing the output and quality of the subsequent sequencing run) and the like. Sx' is a complement of part of the target-hybridizing sequence and other elements are as in previous figures. Below the dashed line, a capture oligomer with a blocking moiety at its 3' end is illustrated (circled x), which prevents formation of the dimer extension product, such that any dimer would not undergo displacement of C.

Figure 7A:
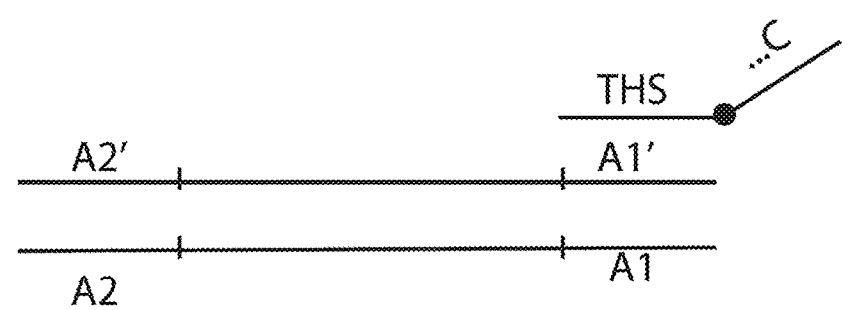

FIG. 7A illustrates an embodiment in which a capture oligomer comprising a capture sequence, various intermediate elements (indicated by " . . . "), a reversible extension blocker (filled circle), and a target-hybridizing sequence (THS) is used. Before unblocking the reversible extension blocker, the capture sequence and the various intermediate elements (if present) are not a template for extension (e.g., of target strands or amplification oligomers). This can facilitate more efficient and more specific extension or amplification by avoiding incorporation of additional sequences complementary to the capture sequence and the various intermediate elements (if present) in the products (e.g., in any mispriming product that may be formed) throughout the extension or amplification process until the reversible extension blocker is unblocked; following unblocking, the capture sequence and the various intermediate elements (if present) can be incorporated.

Figure 7B:
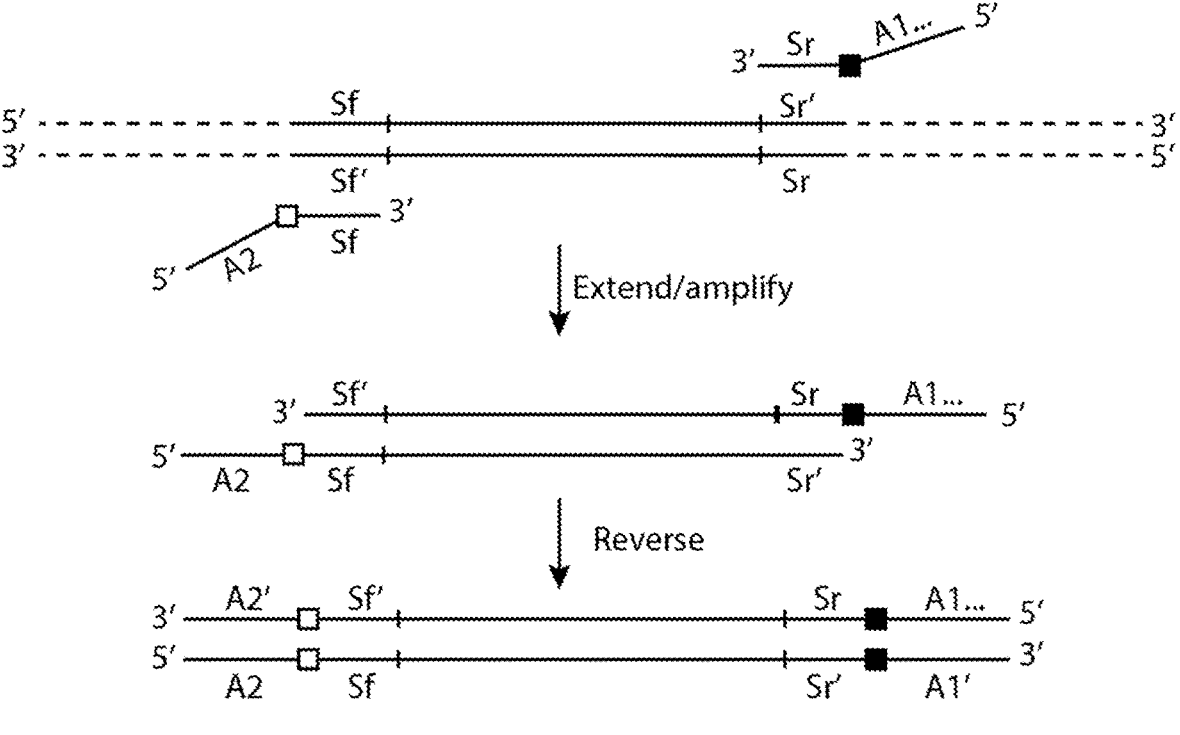

FIG. 7B illustrates an embodiment in which a first amplification oligomer comprising, from 3' to 5', a target hybridizing sequence Sr, a reversible extension blocker (filled square), an additional sequence A1 and optional additional elements (indicated by " . . . "), such as an optional capture sequence, is used. A second amplification oligomer comprising, from 3' to 5', a target hybridizing sequence Sf, a reversible extension blocker (open square; this can be the same or different than the reversible extension blocker in the first amplification oligomer), an additional sequence A2 and optional additional elements (indicated by " . . . "; these can be the same or different than those in the first amplification oligomer), is optionally used (as shown in the figure). Before unblocking the reversible extension blocker or blockers, the additional sequence and optional additional elements (if present) are not a template for extension (e.g., of target strands or amplification oligomers). This can facilitate more efficient and more specific extension or amplification by avoiding incorporation of sequences complementary to the additional sequences and other various elements (if present) in the products (e.g., in any mis-priming product that may be formed) throughout the initial extension or amplification process. The reversible extension blocker or blockers is/are unblocked (if two are present, unblocking can occur concurrently or separately) and the additional sequence and any other elements present can be incorporated in a later phase of the process, such as a later round of extension.

Figure 8A:
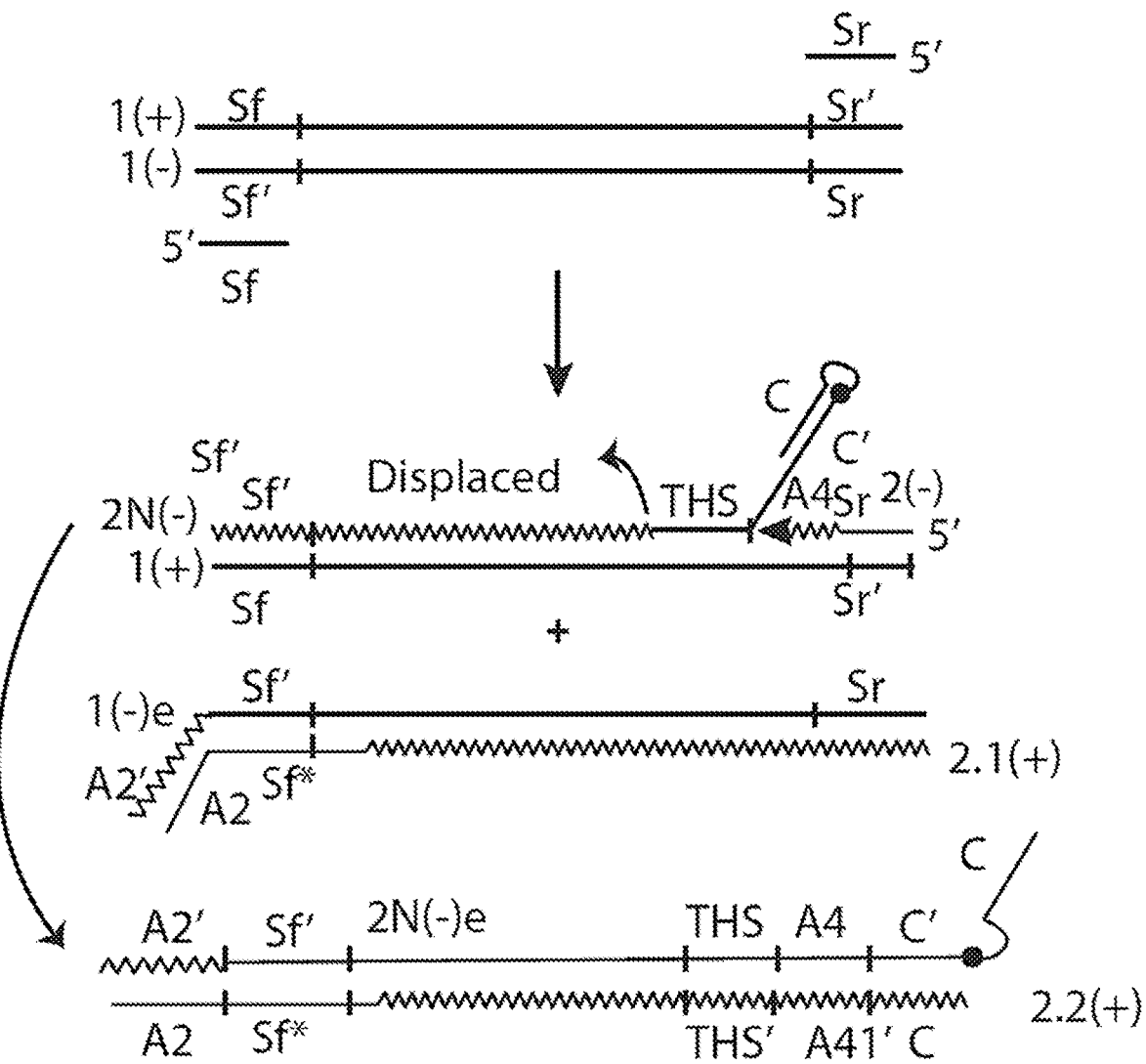

FIG. 8A illustrates exemplary molecules and an exemplary reaction scheme according to the disclosure. The initial target strands 1(+) and 1(–) are as in FIG. 4A. Below the straight vertical arrow, a capture oligomer is provided comprising a target-hybridizing sequence THS and, as described for the oligomer of FIG. 4A additional elements A4, C', an internal extension blocker, and C. THS binds at an internal site in a target strand and undergoes extension to generate product 2N(–). A displacer oligomer comprising Sr is provided, and extension thereof displaces 2N(–) from 1(+) and generates 2(–). A reverse amplification oligomer as in FIG. 4A is provided, extension of which along 1(–) generates 2.1(+), and extension of 1(–) along the reverse amplification oligomer generates 1(–)e. Once 2N(–) is displaced (curved arrow at left), the reverse amplification oligomer anneals to 2N(–) and each is extended, resulting in products 2N(–)e and 2.2(+), which now comprises A2' and in which C is displaced from C'. This reaction scheme illustrates use of a displacer oligomer to facilitate generation in only 1 cycle of a captureable product that contains additional sequence (e.g., adaptors) at both ends of the target sequence. Further, this reaction scheme illustrates an embodiment where the capture oligomer does not bind to a site including the 3' end of a target strand.

Figure 8B:
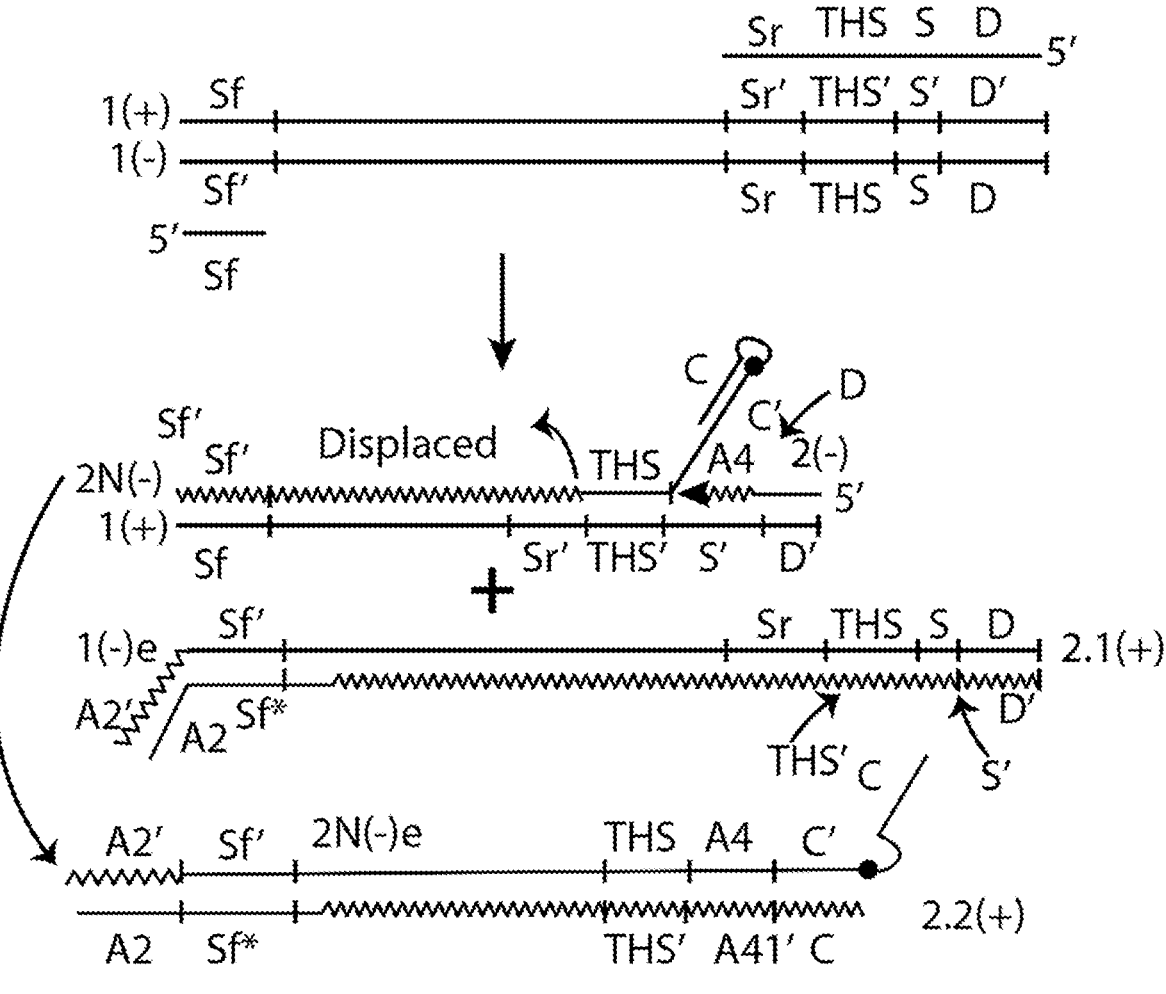

FIG. 8B illustrates additional exemplary molecules and an additional exemplary reaction scheme according to the disclosure. The reaction scheme is substantially similar to that depicted in FIG. 4A with the following exceptions 1) and 2). 1) The initial target strands 1(+) and 1(−) comprise additional sequence comprising target hybridizing sequence THS, optional spacer sequence S and displacer oligomer binding site D. These additional sequences are user-defined, arbitrary sequences and can be incorporated into the target, for example, via an amplification reaction using an amplification oligomer comprising Sr and a sequence tag comprising THS, S and D and an amplification oligomer comprising Sf. 2) The THS of the capture oligomer binds to the user-defined THS site. The reaction otherwise proceeds as illustrated in FIG. 8A, and the resulting products are shown in FIG. 8B. The optional spacer can be useful for improving the extension of the displacer oligomer and subsequent displacement of the capture oligomer. As with the scheme shown in FIG. 4A, this reaction scheme illustrates use of a displacer oligomer to facilitate generation (e.g., in only one cycle) of a capturable product that contains additional sequence (e.g., adaptors) at both ends of the target sequence. Further, this scheme shows the use of additional, user-defined sequence that can function as binding sites for both the capture and displacer oligomers. This design can universalize the approach and allow for a simpler and much more cost-effective means of designing capture and displacer oligomers for use with different targets, including in a multiplex format.

Figure 9:
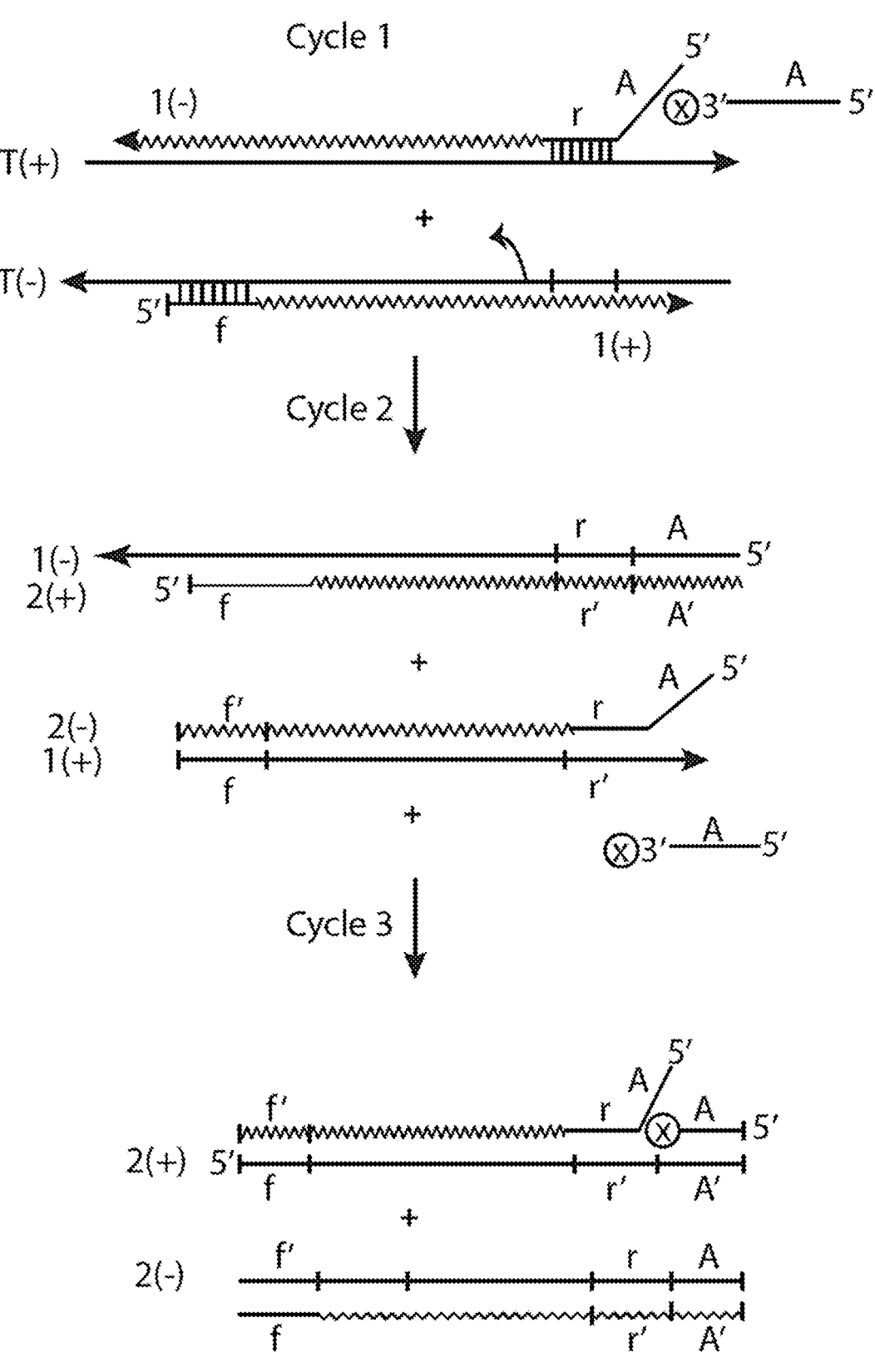

FIG. 9 illustrates the general principle of how a blocker oligomer can prevent hybridization between an additional sequence in an oligomer and the complement thereof in an extension product. An amplification reaction is performed with a forward primer comprising sequence f, which hybridizes to the target strand T(−), and a reverse primer comprising sequence A (an additional sequence not present in the target) and sequence r, which hybridizes to the target strand T(+). Extension generates products 1(−) and 1(+). A blocker oligomer is provided comprising sequence A and a 3' blocking moiety. In cycle 2, the forward primer is extended along 1(−), generating 2(+), and the reverse primer is extended along 1(+), generating 2(−). In cycles 3 and onward, the blocker oligomer anneals to 2(+), meaning that hybridization of r to r' is necessary for the reverse primer to prime extension along 2(+). This can be beneficial in case any mispriming events occur that produce a small amount of side product having an imperfect complement of r but which are extended to include A'. Without the blocker oligomer, binding of the reverse amplification oligomer to the misprimed side product would be more favorable by virtue of the interaction between A of the reverse amplification oligomer and A', leading to more amplification of the side product than would occur when the blocker oligomer is provided. (Meanwhile, the forward primer anneals to 2(−) and undergoes extension.)

Figure 10A:
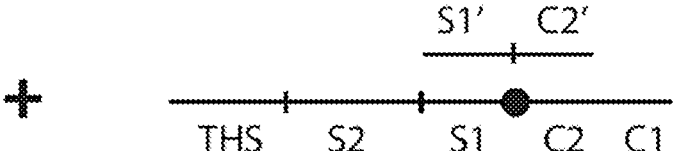

FIG. 10A illustrates exemplary molecules and an exemplary reaction scheme according to the disclosure. A combination of (i) a capture oligomer comprising first and second portions of a capture sequence (C1 and C2), an internal extension blocker (filled circle), first and second portions of a spacer sequence (S1 and S2) and a target-hybridizing sequence (THS) that binds a site in a target strand comprising its 3' end and (ii) a complementary oligomer comprising S1' and C2' is provided. Upon hybridization of the capture oligomer to a target and extension of the target along the capture oligomer up to the internal extension blocker, incorporating S' into the target strand, the complementary oligomer is displaced. The capture oligomer is also extended along the target (note that in other embodiments described herein, the capture oligomer may be blocked and such extension would not occur). A secondary capture reagent is provided comprising a binding partner or solid support (circled B) connected by a linker (zigzag line) to a complement of the capture sequence C'. The secondary capture reagent anneals to capture oligomer bound to the extended target but not to capture oligomer bound to the complementary oligomer, because the latter occupies C2, which is a sufficient amount of the capture sequence to substantially prevent annealing of the secondary capture reagent to the capture oligomer.

Figure 10A:
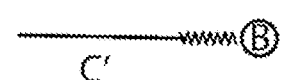
Figure 10B:
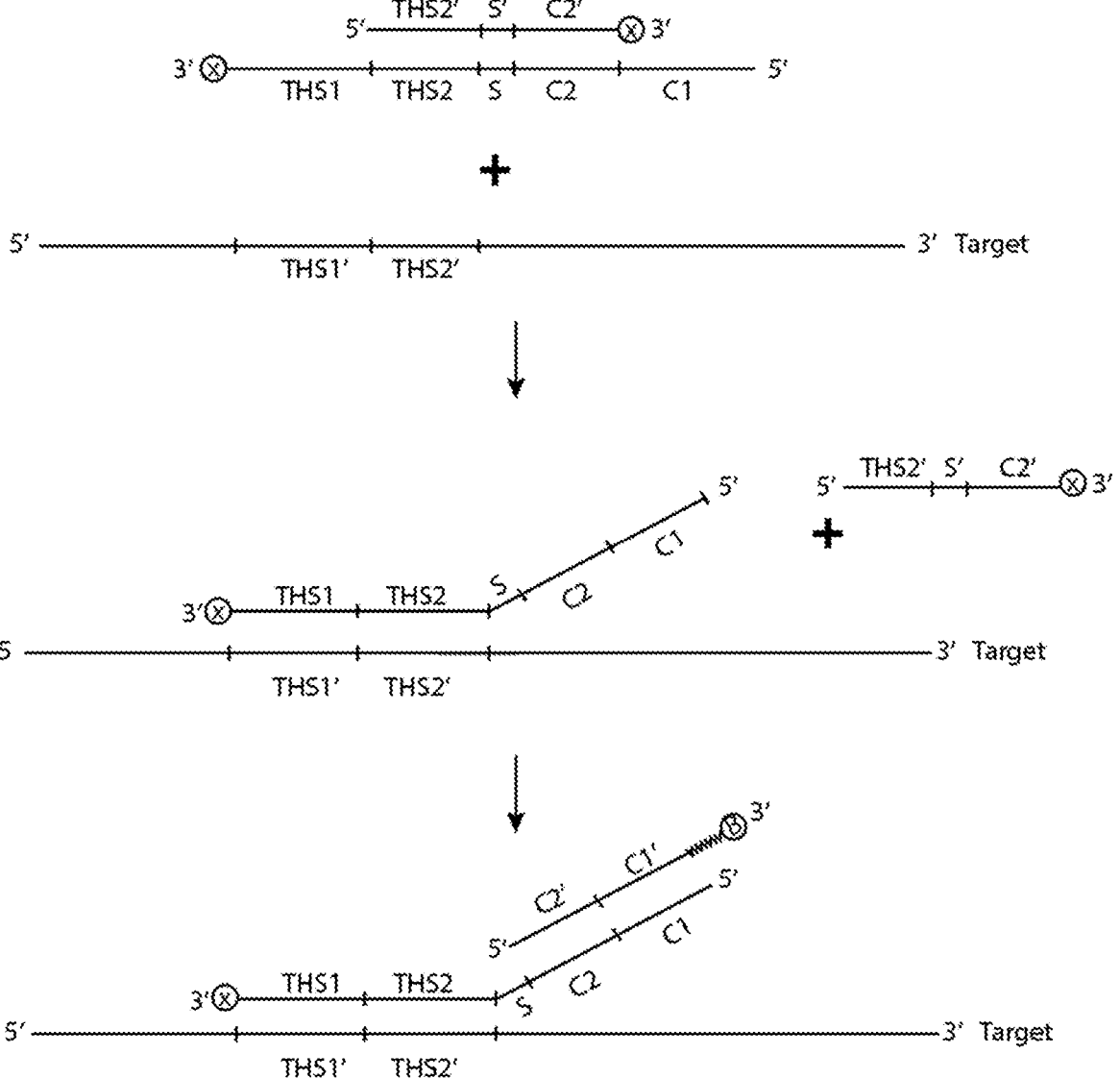

FIG. 10B illustrates an embodiment in which a combination of oligomers is useful for capturing a target polynucleotide from a composition, including a certain amount (e.g., a limited amount or an amount less than or equal to a predetermined amount) thereof if desired. The combination comprises a capture oligomer comprising, from 5' to 3', a first portion of a capture sequence C1, a second portion of a capture sequence C2, an optional spacer sequence S, a second portion of a target hybridizing sequence THS2 a first portion target hybridizing sequence THS1, and an optional blocking moiety (circled X); a separate complementary oligo comprising, from 5' to 3', THS2', S' (optional; may or may not be used when S is present in the capture oligomer) and C2' (wherein the complement of an element is indicated by "'") and an optional blocking moiety at the 3' end (circled X); and a secondary capture reagent comprising the complement of the capture sequence which comprises, from 5' to 3', C2', C1' (C1' or C2' may or may not be complementary to the entire length of C1 and C2), and a binding partner (exemplified in this illustration with a biotin molecule, represented as a circled B). In the absence of target polynucleotide, the complementary oligomer binds to the capture oligomer and blocks accessibility to the full capture sequence to a sufficient extent to block binding of the complement of the capture sequence in the secondary capture reagent (see the complex of complementary oligomer to capture oligomer at the top of the figure). In the presence of target, the THS1 region of the capture oligomer binds to the target followed by binding of the THS2 region—which is energetically favored—thus displacing the THS2' region of the separate complementary oligo from the capture oligomer. When this occurs, the C2' region of the separate complementary is no longer stable enough to bind to the capture oligomer and therefore becomes unbound, thus leaving the full capture sequence available for binding as shown below the first arrow. The complement of the capture sequence in the secondary capture reagent then binds to the capture sequence of the capture oligomer, as shown below the second arrow. This complex can then be isolated from the mixture—e.g., by means of streptavidin coating magnetic microspheres (as described elsewhere in this disclosure)—thus capturing and purifying the target polynucleotide. Optionally, the capture oligomer may be present in the combination in a greater amount than the secondary capture reagent. Such oligomers and combinations are useful for capturing a certain amount (e.g., a limited amount or an amount less than or equal to a predetermined amount) of a target polynucleotide from a composition.

Figure 11A:
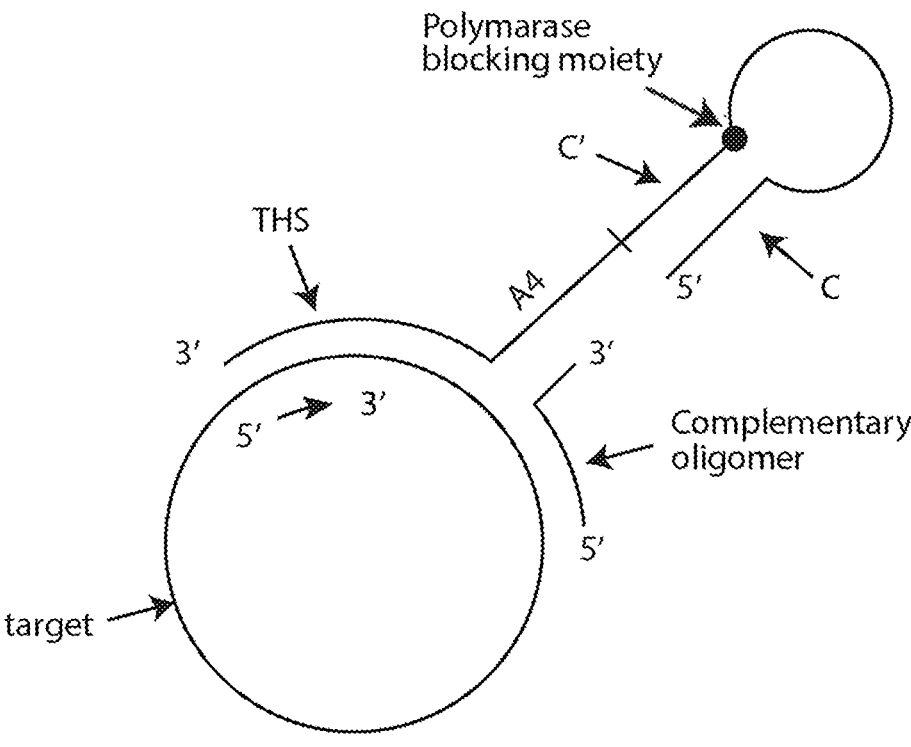
Figure 11B:
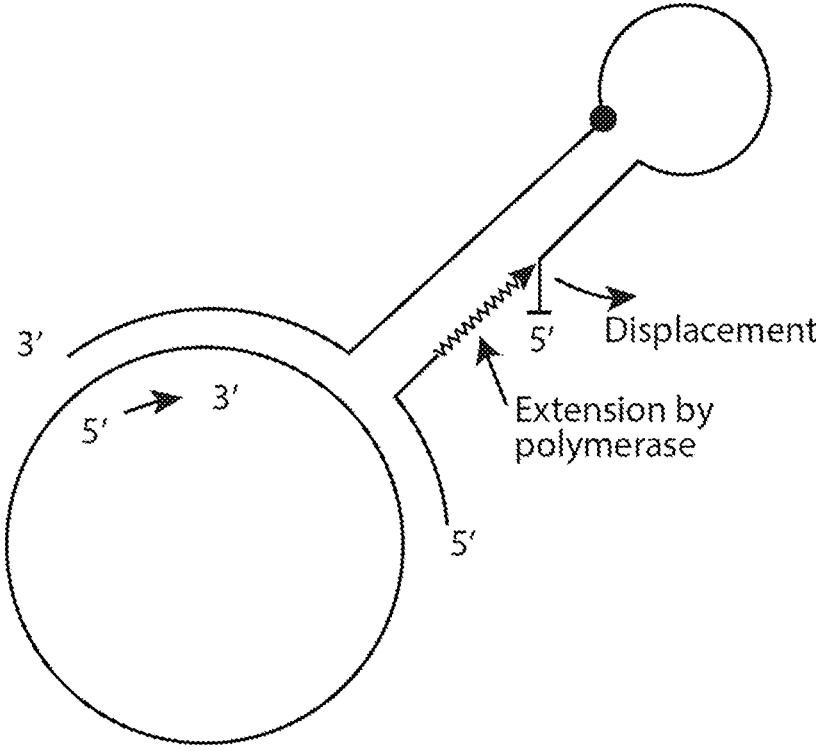

FIGS. 11A-B illustrate exemplary molecules and an exemplary reaction scheme according to the disclosure. In FIG. 11A, a capture oligomer is provided comprising elements essentially as described for the capture oligomer of FIG. 4A, except that THS binds to a site in a target strand (which may be circular, as shown, or linear) that does not comprise a 3' end. A complementary oligomer is provided which comprises (i) a target-hybridizing sequence that anneals adjacent to the THS of the capture oligomer and (ii) a complement of at least part of A4. The complement of at least part of A4 is insufficient to anneal to the capture oligomer in the absence of the target strand. In FIG. 11B, the complementary oligomer is undergoing extension, which will displace C and render it captureable using a secondary capture reagent (not shown). This scheme is useful for capturing circular molecules and/or represents another approach for using capture oligomers that do not bind at the 3' end of a target strand.

Figure 12:
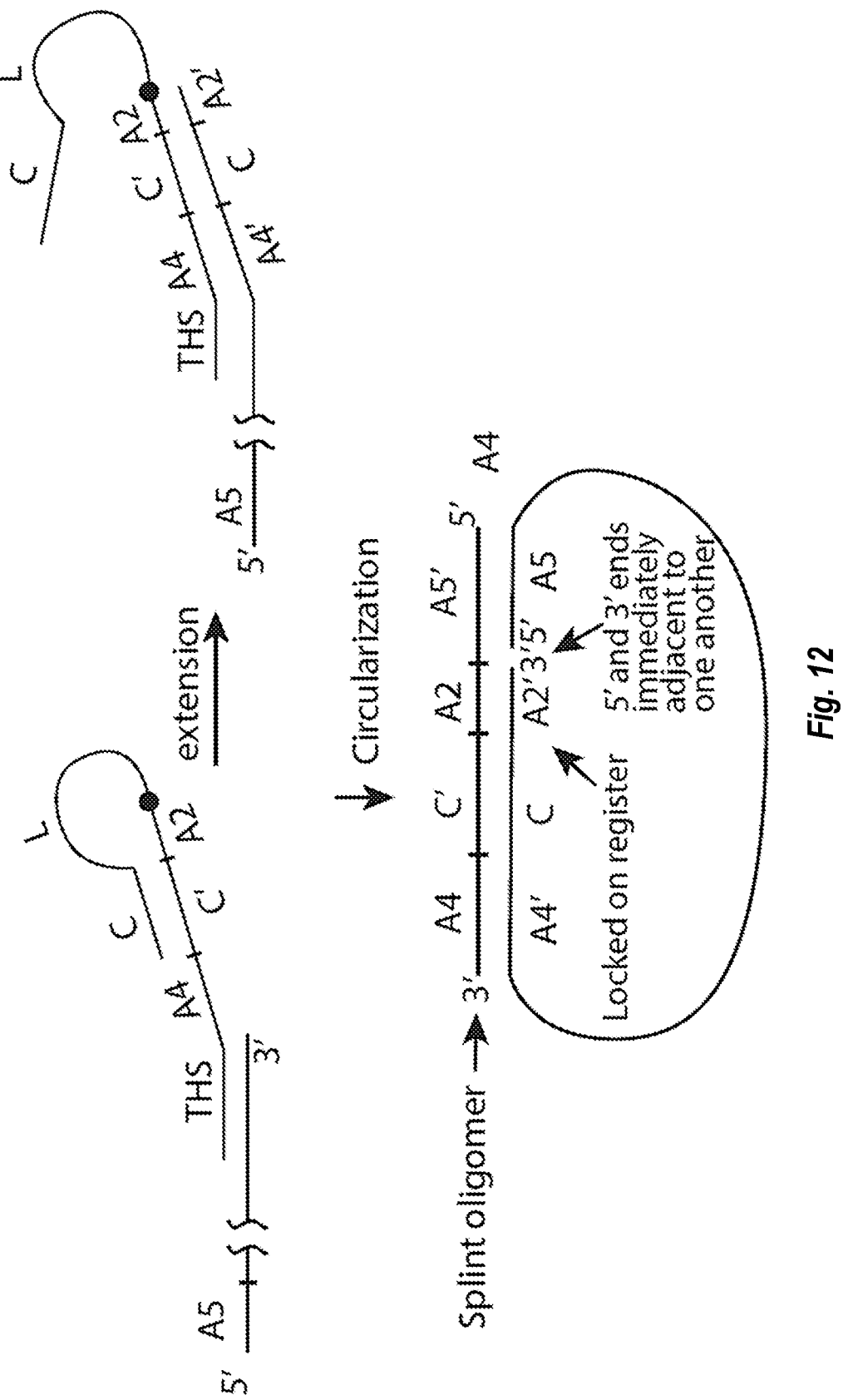

FIG. 12 illustrates exemplary molecules and an exemplary reaction scheme according to the disclosure. A capture oligomer comprising elements as in the capture oligomer of FIG. 4A with a second additional sequence A2, which may comprise a mixed-nucleotide segment, between C' and the internal extension blocker, anneals to a target strand at a site comprising its 3' end. The target strand also comprises sequence A5 at its 5' end, which may be an arbitrary sequence, a primer binding site used in a previous amplification reaction, or a sequence added during a previous step (e.g., amplification or ligation). Extension of the target strand along the capture oligomer adds sequences A4', C, and A2' to the 3' end of the target strand. The presence of A4 in the capture oligomer and A4' in the extended target strand is optional. The extended target strand can then be annealed to a splint oligomer comprising sequences A5', A2, C', and A4, wherein when the extended target strand is annealed to the splint oligomer, the target strand 5' and 3' ends are immediately adjacent. The extended target strand can then be circularized by ligation. The A2 and A2' sequences serve to ensure proper juxtaposition of the extended target strand 5' and 3' ends. This can be helpful when C and C' are repetitive sequences (e.g., poly-A and poly-T or vice versa) that may otherwise be prone to slippage that would inhibit formation of a substrate for ligation. This scheme is useful for capturing and then circularizing a target molecule, e.g., for use in a rolling circle amplification procedure.

Figure 13:
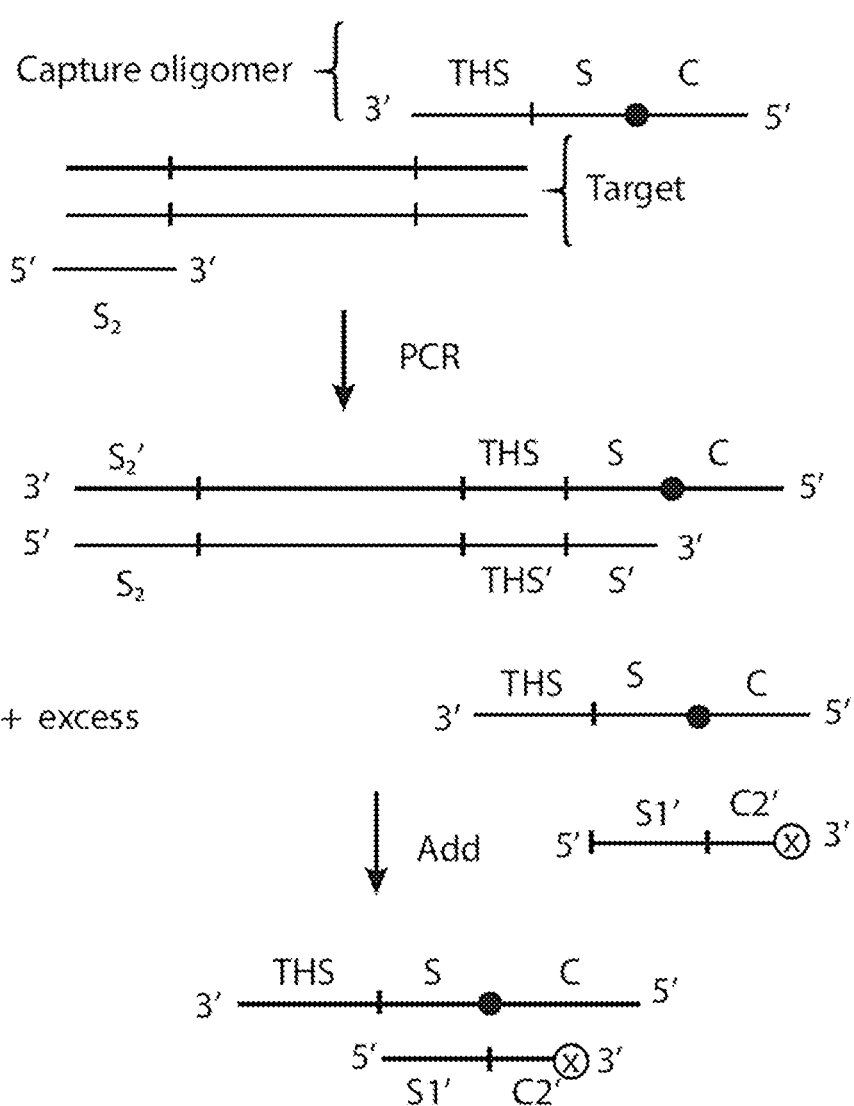
Figure 13:
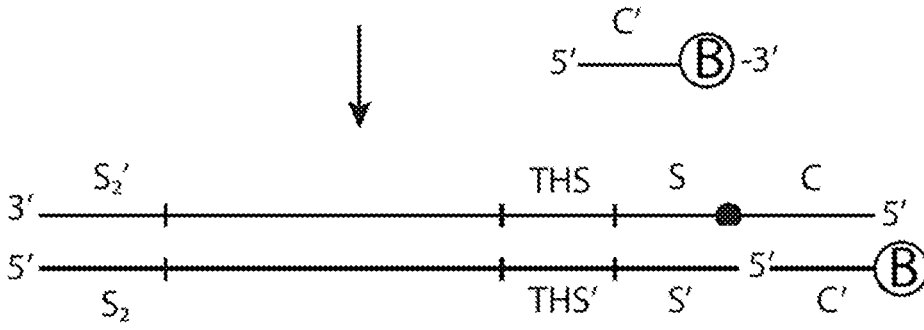

FIG. 13 illustrates exemplary molecules and an exemplary reaction scheme according to the disclosure. A capture oligomer comprising a capture sequence C (comprising first and second portions C1 and C2; not shown), an internal extension blocker (filled circle), a spacer sequence S (comprising first and second portions S1 and S2; not shown), and a target-hybridizing sequence THS is provided along with a reverse amplification oligomer comprising sequence S2. THS and S2 serve to produce an amplified target (e.g., via PCR). A complementary oligomer is added that comprises a complement of the first portion of the spacer sequence S1' and a complement of the second portion of the capture sequence C2'. C2' is insufficient to anneal to C of an amplified target when S' is annealed to S of the other strand of the amplified target. The complementary oligomer does anneal to capture oligomer that is not annealed to an amplified strand. To capture the amplified target, a secondary capture reagent comprising C' and a binding partner or solid support (circled B) is added. The secondary capture reagent binds the amplified target but does not bind capture oligomer that is not annealed to an amplified strand, in which C is blocked to a sufficient degree by C2' of the complementary oligomer.

Figure 14:
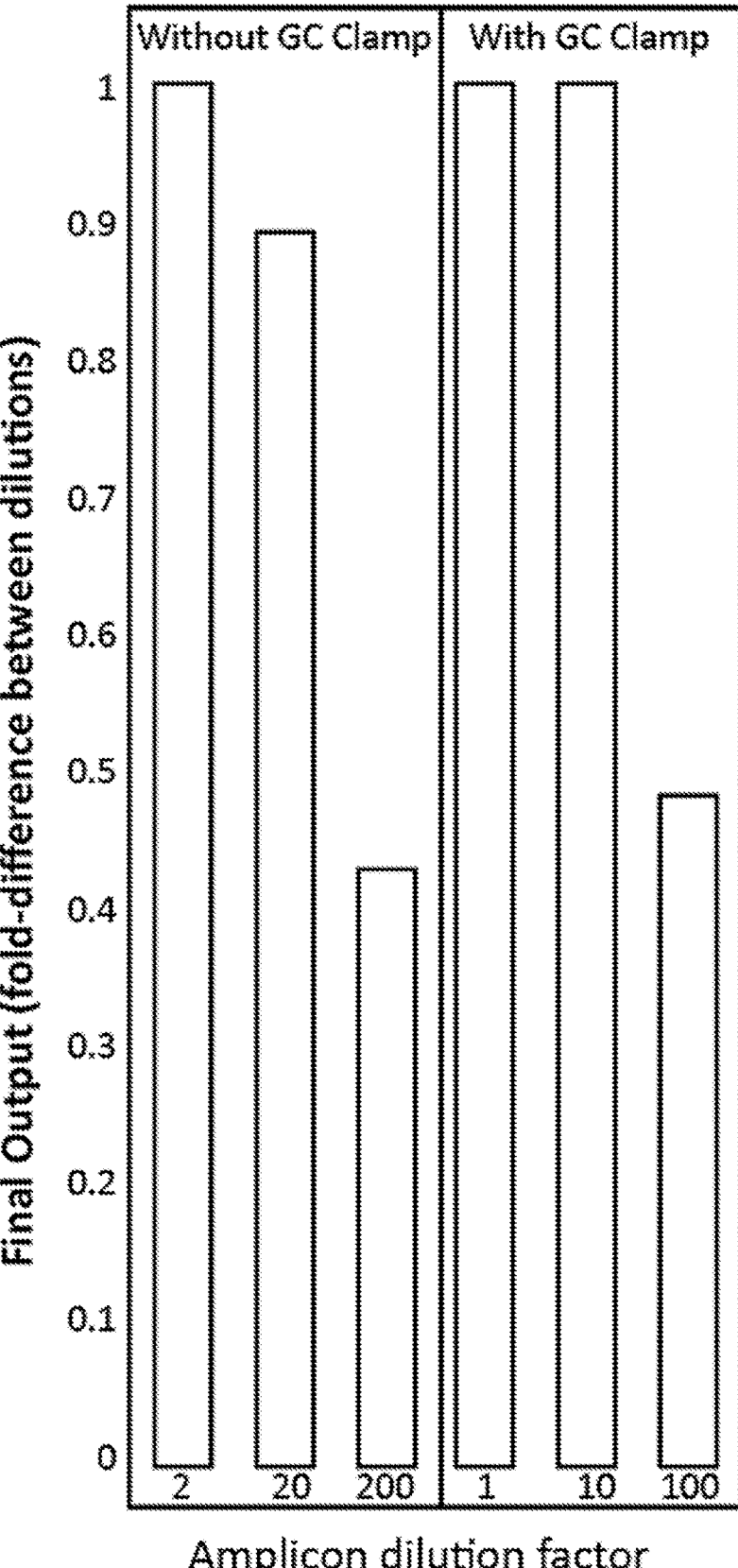

FIG. 14 shows the fold-difference in output of methods using a capture oligomer with or without a clamp sequence.

III. DETAILED DESCRIPTION OF CERTAIN EMBODIMENTS

A. Definitions

Before describing the present teachings in detail, it is to be understood that the disclosure is not limited to specific compositions or process steps, as such may vary. It should be noted that, as used in this specification and the appended claims, the singular form "a," "an," and "the" include plural references, and expressions such as "one or more items" include singular references unless the context clearly dictates otherwise. Thus, for example, reference to "an oligomer" includes a plurality of oligomers and the like. The conjunction "or" is to be interpreted in the inclusive sense, i.e., as equivalent to "and/or," unless the inclusive sense would be unreasonable in the context. When "at least one" member of a class (e.g., oligomer) is present, reference to "the" member (e.g., oligomer) refers to the present member (if only one) or at least one of the members (e.g., oligomers) present (if more than one).

It will be appreciated that there is an implied "about" prior to the temperatures, concentrations, quantities, times, etc. discussed in the present disclosure, such that slight and insubstantial deviations are within the scope of the present teachings herein. In general, the term "about" indicates insubstantial variation in a quantity of a component of a composition not having any significant effect on the activity or stability of the composition, e.g., within 10%, 5%, 2%, or 1%. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed considering the number of reported significant digits and by applying ordinary rounding techniques. All ranges are to be interpreted as encompassing the endpoints in the absence of express exclusions such as "not including the endpoints"; thus, for example, "within 10-15" includes the values 10 and 15 and all intervening integer and (where appropriate) non-integer values. Also, the use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings. Section headings are provided solely for the convenience of the reader and do not limit the disclosure. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components. "Consisting essentially of" means that additional component(s), composition(s), or method step(s) that do not materially change the basic and novel characteristics of the compositions and methods described herein can be included in those compositions or methods. Such characteristics include the ability to, e.g., hybridize to a target polynucleotide and undergo further binding and/or extension reactions as described herein, as the case may be.

A "sample" refers to material that may contain a target polynucleotide, including but not limited to biological, clinical, environmental, and food samples. Environmental samples include environmental material such as surface matter, soil, water, air and industrial samples, as well as samples obtained from food and dairy processing instruments, apparatus, equipment, utensils, disposable and non-disposable items. "Biological" or "clinical" samples refer to a tissue or material derived from a living or dead human, animal, or other organism which may contain a target polynucleotide, including, for example, swabs, washes, aspirates, exudates, biopsy tissue, or body fluids such as blood or urine. A sample can be treated to physically or mechanically disrupt tissue or cell structure to release intracellular nucleic acids into a solution which may contain enzymes, buffers, salts, detergents and the like, to prepare the sample for analysis. These examples are not to be construed as limiting the sample types applicable to the present disclosure.

"Nucleic acid" and "polynucleotide" refer to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" can be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid can be ribose, deoxyribose, or similar compounds with substitutions, e.g., 2' methoxy or 2' halide substitutions. Nitrogenous bases can be conventional bases (A, G, C, T, U), analogs thereof (e.g., inosine, or others; see *The Biochemistry of the Nucleic Acids* 5-36, Adams et al., ed., 11$^{th}$ ed., 1992), derivatives of purines or pyrimidines (e.g., N$^4$-methyl deoxyguanosine, deaza- or aza-purines, deaza- or aza-pyrimidines, pyrimidine bases with substituent groups at the 5 or 6 position (e.g., 5-methylcytosine), purine bases with a substituent at the 2, 6, or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines; U.S. Pat. No. 5,378,825 and PCT No. WO 93/13121). Nucleic acids can include one or more "abasic" residues where the backbone includes no nitrogenous base for position(s) of the polymer (U.S. Pat. No. 5,585,481). A nucleic acid can comprise only conventional RNA or DNA sugars, bases and linkages, or can include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences ester and Wengel, 2004, *Biochemistry* 43(42):13233-41). Embodiments of oligomers that can affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates). Methylated cytosines such as 5-methylcytosines can be used in conjunction with any of the foregoing backbones/sugars/linkages including RNA or DNA backbones (or mixtures thereof) unless otherwise indicated. RNA and DNA equivalents have different sugar moieties (i.e., ribose versus deoxyribose) and can differ by the presence of uracil in RNA and thymine in DNA. The differences between RNA and DNA equivalents do not contribute to differences in homology because the equivalents have the same degree of complementarity to a particular sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24, and 25). References to "the sequence of SEQ ID NO: X" refer to the base sequence of the corresponding sequence listing entry and do not require identity of the backbone (e.g., RNA, 2'-O-Me RNA, or DNA) or base modifications (e.g., methylation of cytosine residues) unless otherwise indicated. Furthermore, T residues are understood to be interchangeable with U residues, and vice versa, unless otherwise indicated.

A "target polynucleotide" refers to a polynucleotide sought to be captured, isolated, amplified, detected, and/or sequenced using a composition or method described herein. In some embodiments, the target polynucleotide comprises a sequence of a DNA or RNA from an organism (e.g., any virus, prokaryote, eukaryote, protist, plant, fungus, animal, mammal, or other biological entity, which may be living or formerly living). Exemplary DNAs include genomic DNA, episomal or plasmid DNA, and mitochondrial DNA. Exemplary RNAs include mRNA, transcribed RNA more generally, ribosomal RNA, miRNA, non-coding RNA, etc. (and genomic RNA where applicable, e.g., in the case of certain viruses). Target polynucleotides also include amplicons comprising the nucleic acids discussed above, to which additional sequences (such as any additional sequence described herein) may have been added. In some embodiments, a target polynucleotide comprises a non-naturally occurring sequence, e.g., resulting from in vitro synthesis, ligation, site-directed mutagenesis, recombination, or the like.

An "oligomer" or "oligonucleotide" refers to a nucleic acid of generally less than 1,000 nucleotides (nt), including those in a size range having a lower limit of about 2 to 5 nt and an upper limit of about 500 to 900 nt. Some particular embodiments are oligomers in a size range with a lower limit of about 5 to 15, 16, 17, 18, 19, or 20 nt and an upper limit of about 50 to 600 nt, and other particular embodiments are in a size range with a lower limit of about 10 to 20 nt and an upper limit of about 30 to 100 nt. Oligomers can be purified from naturally occurring sources, but can be synthesized by using any well known enzymatic or chemical method. Oligomers can be referred to by a functional name (e.g., capture probe, primer or promoter primer) but those skilled in the art will understand that such terms refer to oligomers. Oligomers can form secondary and tertiary structures by self-hybridizing or by hybridizing to other polynucleotides. Such structures can include, but are not limited to, duplexes, hairpins, cruciforms, bends, and triplexes. Oligomers may be generated in any manner, including chemical synthesis, DNA replication, reverse transcription, PCR, or a combination thereof. In some embodiments, oligomers that form invasive cleavage structures are generated in a reaction (e.g; by extension of a primer in an enzymatic extension reaction).

"Arbitrary sequence" refers to any sequence that is chosen, selected, determined, designed, etc., by the user, typically to serve a desired function or purpose in a downstream process. In a preferred mode, the arbitrary sequence is designed to be non-complementary to or otherwise non-reactive with a target sequence or sequences under given conditions of a process. In some embodiments, the arbitrary sequence can be a randomly-generated sequence or set of sequences, for example for use as a unique molecular identifier.

"Capture oligomer," "capture oligonucleotide," "capture probe," "target capture oligomer," and "capture probe oligomer" are used interchangeably to refer to a nucleic acid oligomer that comprises (i) a target-hybridizing sequence capable of specifically hybridizing to a target sequence in a target nucleic acid and (ii) a capture sequence capable of hybridizing to a secondary oligomer, e.g., immobilized on a solid support or linked to a binding partner to facilitate isolation of a complex comprising the capture oligomer, the target, and the secondary oligomer from other molecules in a composition.

By "amplicon" or "amplification product" is meant a nucleic acid molecule generated in a nucleic acid amplification reaction and which is derived from a template nucleic acid. An amplicon or amplification product contains an amplified nucleic acid sequence (e.g., target nucleic acid) that can be of the same or opposite sense as the template nucleic acid. In some embodiments, an amplicon has a length of about 100-30,000 nucleotides, about 100-10,000 nucleotides, about 100-5000 nucleotides, 100-2000 nucleotides, about 100-1500 nucleotides, about 100-1000 nucleotides, about 100-800 nucleotides, about 100-700 nucleotides, about 100-600 nucleotides, or about 100-500 nucleotides.

An "amplification oligonucleotide" or "amplification oligomer" refers to an oligonucleotide that hybridizes to a target nucleic acid, or its complement, and participates in a nucleic acid extension or amplification reaction, e.g., serving as a primer and/or promoter-primer. Amplification oligomers also encompass promoter-providers, which contain a promoter from which transcription can be initiated but are not necessarily extendable by a DNA polymerase and may comprise a 3' blocking moiety. Particular amplification oligomers contain a target-hybridizing sequence of at least about 10 contiguous bases, and optionally at least 11, 12, 13, 14, 15, 16, 17, 18, 19, 20, 21, 22, 23, 24 or 25 contiguous bases, that are complementary to a region of the target nucleic acid sequence or its complementary strand. Other exemplary lengths or ranges of lengths for target-hybridizing sequences are described elsewhere herein and can apply to amplification oligomers. The contiguous bases can be at least about 70%, at least about 80%, at least about 90%, or completely complementary to the target sequence to which the amplification oligomer binds. In some embodiments, an amplification oligomer comprises an intervening linker or non-complementary sequence between two segments of complementary sequence, e.g., wherein the two complementary segments of the oligomer collectively comprise at least about 10 complementary bases, and optionally at least 11, 12, 13, 14, 15, 16, 17, 18, 19, or 20 complementary bases. In some embodiments, amplification oligomers are about 10 to about 60 bases long and optionally can include modified nucleotides. An amplification oligomer can be optionally modified, e.g., by including a 5' region that is non-complementary to the target sequence. Such modification can include functional additions, such as tags, promoters, or other sequences used or useful for manipulating or amplifying the primer or target oligonucleotide.

A "primer" refers to an oligomer that hybridizes to a template nucleic acid and has a 3' end that is extended by polymerization. A primer can be optionally modified, e.g., by including a 5' region that is non-complementary to the target sequence. Such modification can include functional additions, such as tags, promoters, or other sequences used or useful for manipulating or amplifying the primer or target oligonucleotide.

A first sequence is a "complement" of a second sequence (or, equivalently, is "complementary" to the second sequence) where the first sequence has a length and content sufficient to anneal to the second sequence under reasonable binding conditions, which may be but are not necessarily stringent hybridization conditions described herein and also encompass, e.g., annealing conditions as used in standard PCR and other techniques involving primer or probe binding and extension.

A "tag" refers to any additional sequence other than a target-hybridizing sequence that may be included in an oligomer. Any arbitrary sequence that is present in addition to a target-hybridizing sequence can serve as a tag. A tag includes but is not limited to an adaptor (see below). Additional examples of tags are promoters, mixed-nucleotide elements described elsewhere herein, and stabilizing sequences including clamps.

An "adaptor" is a sequence that adapts the molecule to which it is added to provide a binding site for another molecule (e.g., a sequencing primer, or a target-hybridizing sequence (THS) of a capture oligomer). The binding site may be a universal binding site (e.g., for multiple capture oligomers, all with the same THS, in a multiplex format, or for a universal primer). Additional examples of binding sites are a binding site for a displacer oligomer, probe, capture oligomer, or nucleic acid modifying enzyme (e.g., RNA polymerase, primase, ligase, RNAse (such as RNAse H) or a restriction enzyme), or for attachment to a solid phase (including via a solid phase primer or capture oligomer) including for use in clonal amplification, or other functional element or elements useful in a downstream application, e.g., enrichment, library preparation, clonal amplification or sequencing. Thus, sample barcodes or index sequences, key or calibrator sequences, molecular barcodes (including unique molecular identifier), sites for downstream cloning and sites for circularization of a target molecule are additional examples of elements that can be included in adaptors.

A "linker" is a sequence or non-sequence element or a combination thereof that connects one portion of an oligomer to another. In some embodiments, a sequence linker comprises sequence that does not hybridize to a target polynucleotide and/or to other oligomers in a combination or composition. In some embodiments, a non-sequence linker comprises alkyl, alkenyl, amido, or polyethylene glycol groups $[(-CH_2CH_2O-)_n]$.

A "stabilizing sequence" is a clamp, mixed-nucleotide region, or other sequence that functions to increase the stability of a duplex region and/or control the register of hybridization (e.g., when located adjacent to a sequence prone to slippage, such as a containing repeating nucleotides, e.g., a poly-dA or poly-dT sequence). An "aligning sequence" is a stabilizing sequence that controls the register of hybridization. In addition to clamps and mixed-nucleotide regions described elsewhere herein, stabilizing sequences include GC-rich sequences and sequences containing affinity-enhancing modifications.

An "internal extension blocker" is an element located within the sequence of a nucleic acid or bound to the nucleic acid that prevents extension of a complementary strand along the nucleic acid. Examples include a non-nucleotide linker or one or more abasic sites, non-natural nucleotides, or chemically modified natural nucleotides, as well as reversible extension blockers discussed below.

A "reversible extension blocker" is an internal extension blocker that can have its blocking function reversed, i.e., be rendered permissive for extension of the complementary strand. An exemplary reversible extension blocker is a non-natural nucleotide that has a complementary nucleotide that is accepted by a polymerase and that exhibits specificity relative to natural nucleotides (i.e., a polymerase will not add a natural base across from the reversible extension blocker). Providing the complementary nucleotide reverses the blocking function. Examples of non-natural base pairs, where either member of the pair can serve as the reversible extension blocker, are Iso-dC or Iso-dG; xanthine or 5-(2,4 diaminopyrimidine); 2-amino-6-(N,N-dimethylamino)purine or pyridine-2-one; 4-Methylbenzimidizole or 2,4 Difluorotoluene; 7-Azaindole or Isocarbostyril; dMMO2 or d5SICS; or dF or dQ. Other examples of a reversible extension blocker are a chemically modified nucleotide or nucleotides wherein the modification is attached via a reversible linkage, wherein the linkage can be reversed by providing any one or more of a chemical, an enzyme, a temperature change, a reagent composition change, etc.; a reversible nucleic acid structural feature; or a molecule reversibly bound to the capture oligomer, optionally wherein the reversibly bound molecule is a protein, an enzyme, a lipid, a carbohydrate, or a chemical moiety.

"Nucleic acid amplification" refers to any in vitro procedure that produces multiple copies of a target nucleic acid sequence, or its complementary sequence, or fragments thereof (i.e., an amplified sequence containing less than the complete target nucleic acid). Examples of nucleic acid amplification procedures include transcription associated methods, such as transcription-mediated amplification (TMA), nucleic acid sequence-based amplification (NASBA) and others (e.g., U.S. Pat. Nos. 5,399,491, 5,554, 516, 5,437,990, 5,130,238, 4,868,105, and 5,124,246), replicase-mediated amplification (e.g., U.S. Pat. No. 4,786, 600), the polymerase chain reaction (PCR) (e.g., U.S. Pat. Nos. 4,683,195, 4,683,202, and 4,800,159), rolling circle amplification (RCA) (e.g., U.S. Pat. Nos. 5,854,033 and 6,143,495), recombinase polymerase amplification (RPA) (e.g., U.S. Pat. No. 7,666,598), ligase chain reaction (LCR) (e.g., EP Pat. App. 0320308) and strand-displacement amplification (SDA) (e.g., U.S. Pat. No. 5,422,252). Replicase-mediated amplification uses self-replicating RNA molecules, and a replicase such as QB-replicase. PCR amplification uses DNA polymerase, primers, and thermal cycling steps to synthesize multiple copies of the two complementary strands of DNA or cDNA. LCR amplification uses at least four separate oligonucleotides to amplify a target and its complementary strand by using multiple cycles of hybridization, ligation, and denaturation. SDA uses a primer that contains a recognition site for a restriction endonuclease that will nick one strand of a hemimodified DNA duplex that includes the target sequence, followed by amplification in a series of primer extension and strand displacement steps. Particular embodiments use PCR, but it will be apparent to persons of ordinary skill in the art that oligomers disclosed herein can be readily used as primers in other amplification methods.

By "hybridization" or "hybridize" is meant the ability of two completely or partially complementary nucleic acid strands to come together under specified hybridization assay conditions in a parallel or antiparallel orientation to form a stable structure having a double-stranded region. "Hybridization" and "hybridize" are synonymous with "annealing" and "anneal," respectively. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., R. L. P. Adams et al., *The Biochemistry of the Nucleic Acids* (11th ed. 1992).)

As used herein, the term "specifically hybridizes" means that under given hybridization conditions a probe, primer, or other oligomer (e.g., capture oligomer) detectably hybridizes substantially only to its target sequence(s) in a sample comprising the target sequence(s) (i.e., there is little or no detectable hybridization to non-targeted sequences). Notably, an oligomer can be configured to specifically hybridize to any one of a set of targets (e.g., sequences from organisms of a particular taxonomic group, e.g., genus). In some embodiments, a probe, primer, or other oligomer (e.g., capture oligomer) can hybridize to its target nucleic acid to form a stable oligomer:target hybrid, but not form a sufficient number of stable oligomer:non-target hybrids for amplification or capture as the case may be. Amplification and capture oligomers that specifically hybridize to a target nucleic acid are useful to amplify and capture target nucleic acids, but not non-targeted nucleic acids, especially non-targeted nucleic acids of phylogenetically closely related organisms. Thus, the oligomer hybridizes to target nucleic acid to a sufficiently greater extent than to non-target nucleic acid to enable one having ordinary skill in the art to accurately capture, amplify, and/or detect the presence (or absence) of nucleic acid derived from the specified target (e.g., a particular pathogen) as appropriate. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-targeted nucleic acid sequences.

By "stringent hybridization conditions," or "stringent conditions" is meant conditions (1) permitting an oligomer to preferentially hybridize to a target nucleic acid as opposed to a different nucleic acid (e.g., a nucleic acid having as little as 1 nucleotide difference in identity to the target nucleic acid) or (2) permitting only an oligomer with a higher affinity target-hybridizing sequence (relative to an oligomer with a lower affinity target-hybridizing sequence) to hybridize to a target, e.g., wherein the higher affinity target-hybridizing sequence is longer than the lower affinity target-hybridizing sequence and/or comprises affinity-enhancing modifications that the lower affinity target-hybridizing sequence does not comprise. While the definition of stringent hybridization conditions does not vary, the actual reaction environment that can be used for stringent hybridization may vary depending upon factors including the GC content and length of the oligomer, the degree of similarity between the oligomer sequence and sequences of targeted and non-targeted nucleic acids that may be present in the test sample. Hybridization conditions include the temperature and the composition of the hybridization reagents or solutions. Exemplary stringent hybridization conditions with the oligomers of the present disclosure correspond to a temperature of about 40° C. to 75° C., e.g., 40° C. to 50° C., 50° C. to 60° C., or 60° C. to 75° C., when the monovalent cation concentration is in the range of about 0.4-1 M and the divalent cation concentration is in the range of about 0-10 mM and the pH is in the range of about 5-9. Additional details of hybridization conditions are set forth in the Examples section. Other acceptable stringent hybridization conditions could be easily ascertained by those having ordinary skill in the art.

"Label" or "detectable label" refers to a moiety or compound joined directly or indirectly to a probe that is detected or leads to a detectable signal. Any detectable moiety can be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent, or chemiluminescent compound), and fluorescent compound (i.e., fluorophore). Embodiments of fluorophores include those that absorb light (e.g., have a peak absorption wavelength) in the range of about 495 to 690 nm and emit light (e.g., have a peak emission wavelength) in the range of about 520 to 710 nm, which include those known as FAM™, TET™, HEX, CAL FLUOR™ (Orange or Red), CY, and QUASAR™ compounds. Fluorophores can be used in combination with a quencher molecule that absorbs light when in close proximity to the fluorophore to diminish background fluorescence. Such quenchers are well known in the art and include, e.g., BLACK HOLE QUENCHER™ (or BHQ™), Blackberry Quencher® (or BBQ-650, Eclipse®, or TAMRA™ compounds.

A "non-extendable" oligomer or an oligomer comprising a "blocking moiety at its 3' end" includes a blocking moiety sufficiently close to its 3'-terminus (also referred to as the 3' end) to prevent extension. Any blocking moiety that is sufficiently close to the 3'-terminus to block extension is considered to be "at" the 3'-terminus for purposes of the present disclosure even if it is not bound to or present in place of a 3' hydroxyl or oxygen. A blocking moiety near the 3' end is in some embodiments within five residues of the 3' end and is sufficiently large to limit binding of a polymerase to the oligomer, and other embodiments contain a blocking moiety covalently attached to the 3' terminus. Many different chemical groups can be used to block the 3' end, e.g., alkyl groups, non-nucleotide linkers, alkane-diol dideoxynucleotide residues (e.g., 3'-hexanediol residues), and cordycepin. Further examples of blocking moieties include a 3'-deoxy nucleotide (e.g., a 2',3'-dideoxy nucleotide); a 3'-phosphorylated nucleotide; a fluorophore, quencher, or other label that interferes with extension; an inverted nucleotide (e.g., linked to the preceding nucleotide through a 3'-to-3' phosphodiester, optionally with an exposed 5'-OH or phosphate); or a protein or peptide joined to the oligonucleotide so as to prevent further extension of a nascent nucleic acid chain by a polymerase. A non-extendable oligonucleotide of the present disclosure can be at least 10 bases in length, and can be up to 15, 20, 25, 30, 35, 40, 50 or more nucleotides in length. Non-extendable oligonucleotides that comprise a detectable label can be used as probes.

A "binding partner" is a member of a pair of moieties that can be used to form a noncovalent association. An exemplary set of binding partners is biotin and a biotin-binding agent. Further examples of binding partners include, but are not limited to digoxygenin/anti-digoxygenin and more generally an antibody and its target.

A "biotin-binding agent" is an agent (e.g., polypeptide) that can specifically bind biotin. Streptavidin, avidin, and NeutrAvidin represent examples of biotin-binding agents. An anti-biotin antibody is also considered a biotin-binding agent.

The term "antibody" encompasses any polypeptide comprising a functional antigen-binding region having complementarity-determining regions and framework regions (e.g., a VH and VL domain), including without limitation scFv, Fab, and full-length antibodies (e.g., IgA, IgG, IgD, IgE, or IgM antibodies).

As used herein, a "kit" is a packaged combination of reagents, including, e.g., one or more oligonucleotides disclosed herein. For example, a kit can include a packaged combination of one or more vials, tubes, or cartridges having a plurality of chambers containing reagents for isolating target polynucleotides. The reagents can include capture, primer and probe oligonucleotides such as those described herein, as well as nucleotide polymerizing enzymes (e.g., a DNA polymerase, a reverse transcriptase, an RNA polymerase, etc.). In certain embodiments, the reagents can be in liquid form, in solid form (e.g., a lyophilisate), or a semi-solid form (e.g., a glass). In some embodiments, oligonucleotide reagents and enzyme reagents are present in the kit as components of a single lyophilized composition (e.g., a pellet). In such an instance, primers, probes, and one or more enzymes (e.g., a DNA polymerase) can be disposed in the same reaction chamber or vessel in a lyophilized form that can be reconstituted with an aqueous reagent, where a separate vial or tube containing the aqueous reagent is included in the same kit. The kits may further include a number of optional components such as, for example, other oligomers. Other reagents that may be present in the kits include reagents suitable for performing in vitro amplification such as buffers, salt solutions, and/or appropriate nucleotide triphosphates (e.g., dATP, dCTP, dGTP, dTTP; and/or ATP, CTP, GTP and UTP). Kits further can include a solid support material (e.g., magnetically attractable particles, e.g., magnetic beads) for immobilizing the oligomers, either directly or indirectly, in a sample-preparation procedure. In certain embodiments, the kit further includes a set of instructions for practicing methods in accordance with the present disclosure, where the instructions may be associated with a package insert and/or the packaging of the kit or the components thereof.

As used herein, a "combination" of oligomers refers to any plurality of oligomers in proximity to each other, e.g., in different containers or the same container in a kit, or in a composition or set of compositions juxtaposed to one another, e.g., in a plate, rack, or other container.

Unless defined otherwise, all scientific and technical terms used herein have the same meaning as commonly understood by those skilled in the relevant art. General definitions can be found in technical books relevant to the art of molecular biology, e.g., DICTIONARY OF MICROBIOLOGY AND MOLECULAR BIOLOGY, 2nd ed. (Singleton et al., 1994, John Wiley & Sons, New York, NY) or THE HARPER COLLINS DICTIONARY OF BIOLOGY (Hale & Marham, 1991, Harper Perennial, New York, NY).

B. Exemplary Compositions, Kits, Methods, and Uses

The present disclosure provides oligomers, compositions, and kits, useful for isolating target polynucleotides and/or attaching tags such as adaptors. Isolation includes isolation in limited amounts (limited capture) and specific amounts (copy control). For example, in certain workflows it is desirable to capture (or amplify and capture) an amount of a target polynucleotide (which for example may be a natural DNA or RNA or an amplicon) no greater than a predetermined amount (e.g., a maximum desirable value for a downstream application, such as sequencing library preparation) but otherwise as high as possible. Similarly, in certain workflows it is desirable to capture (or amplify and capture) a predetermined specific amount (e.g., a specific number of molecules or copies of molecules) of a target polynucleotide (which for example may be a natural DNA or RNA, an amplicon or a sequencing library) for use in a downstream application (e.g., clonal amplification, including in next generation sequencing workflows). Further, in certain workflows it is desirable to incorporate additional sequences into a target polynucleotide, such as incorporation of adaptors into a sequencing library. Oligomers comprising various elements are described herein. Unless otherwise indicated, additional elements may be present before, between, or after the recited elements of the oligomers, to the extent that they do not interfere with the functionality thereof.

In some embodiments, oligomers are provided, e.g., in a kit or composition. Oligomers generally comprise a target-hybridizing region, e.g., configured to hybridize specifically to a target polynucleotide. While oligomers of different lengths and base composition can be used, in some embodiments oligomers in this disclosure have target-hybridizing regions of a length set forth in the section discussing target-hybridizing sequences. In some embodiments, an oligomer comprises additional regions of sequence as set forth in detail elsewhere herein, which can be located 5' of the target-hybridizing region. In some embodiments, an oligomer does not comprise a second region of sequence. In some embodiments, the additional regions of sequence comprise a capture sequence.

Figures 1A, 1B:
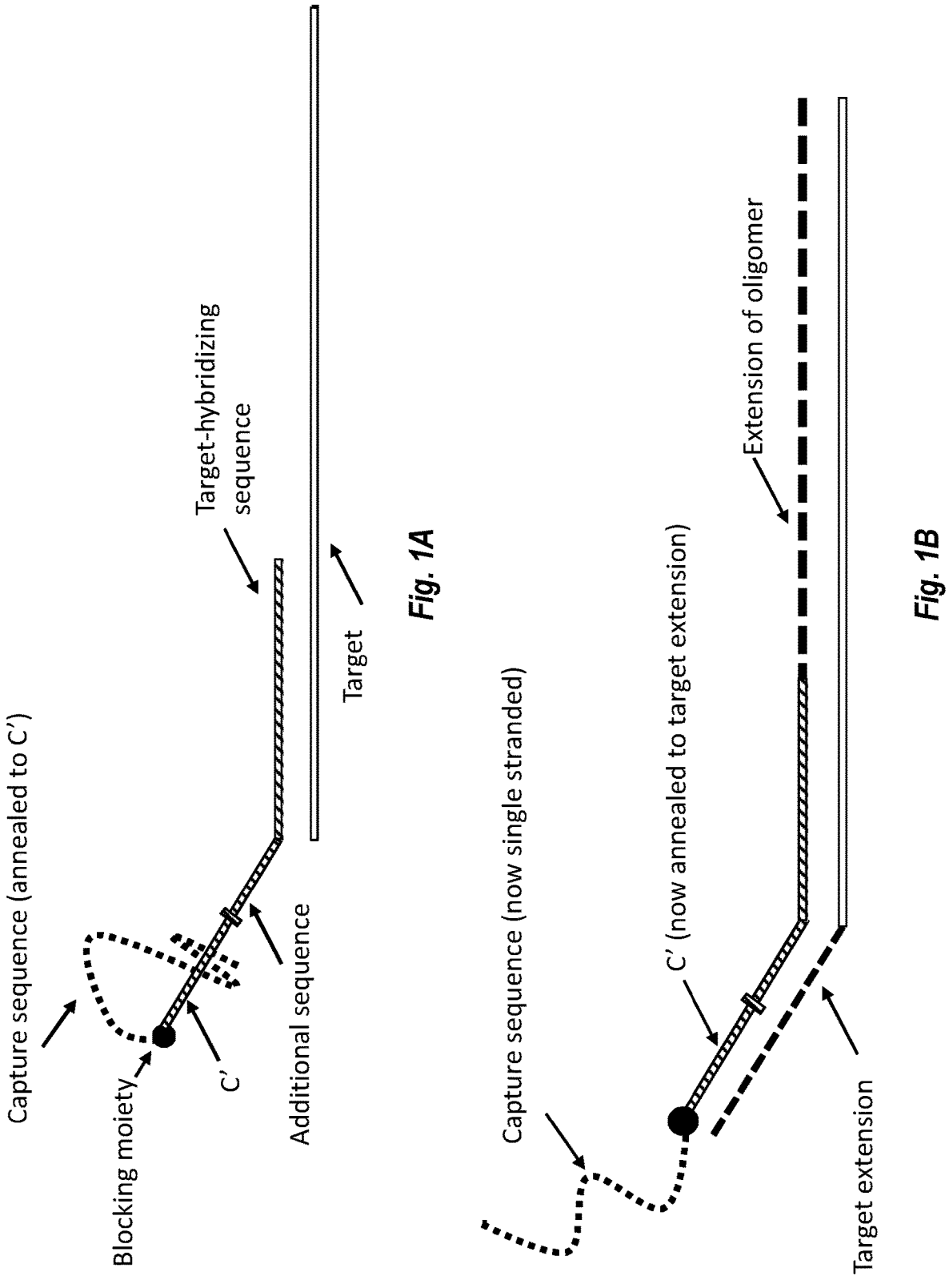
Figure 1C:
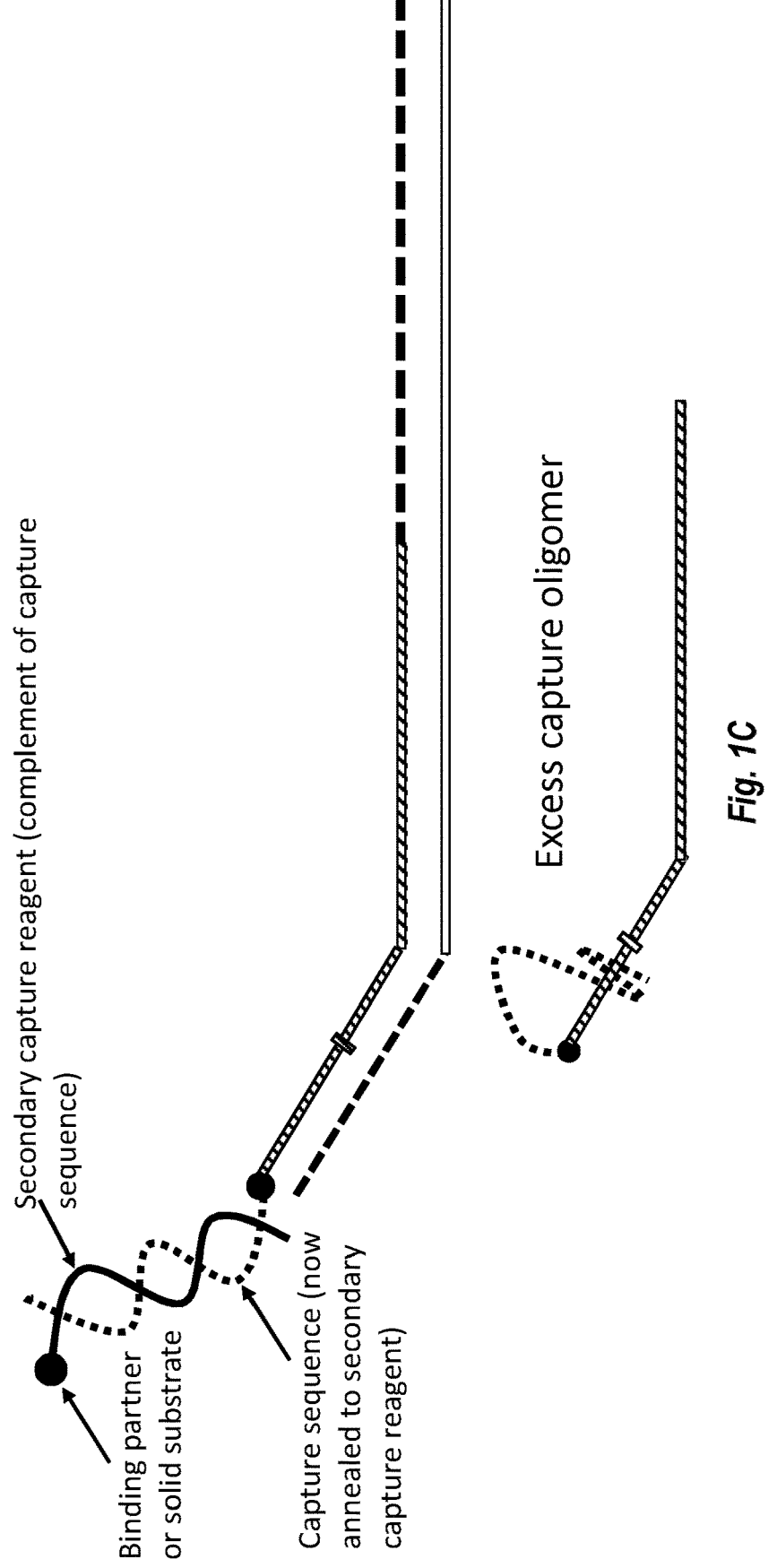
Figure 2A:
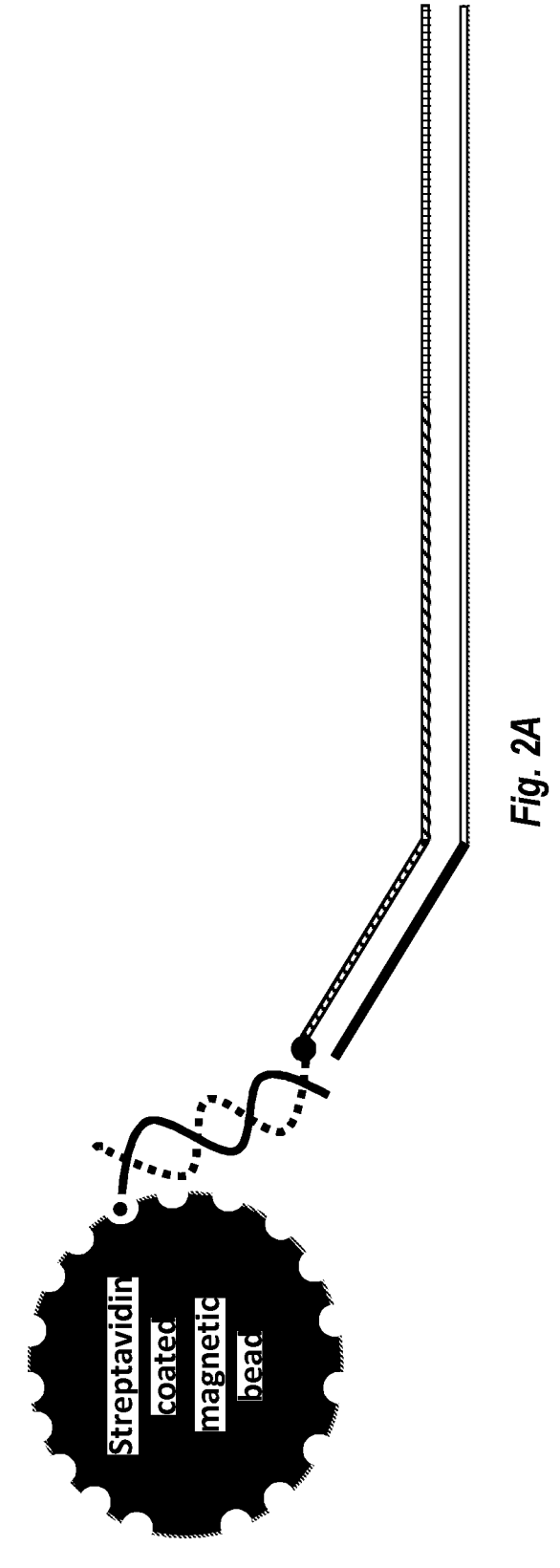
FIG. 2B illustrates an embodiment of the disclosure in which the complex of the extended capture oligomer and target from FIG. 2A has been eluted from the secondary capture reagent.
Figure 2B:
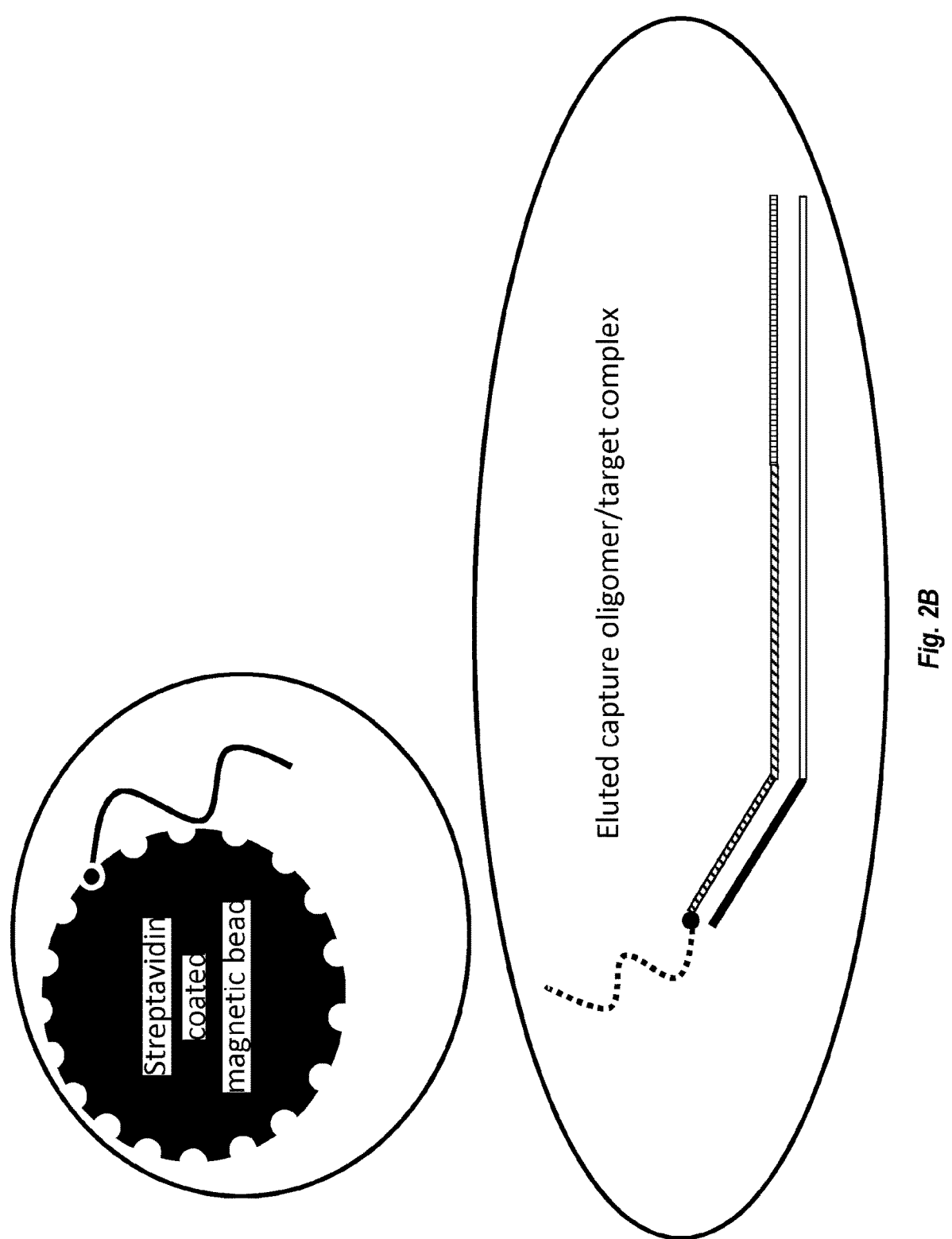

1. Capture Oligomers and Combinations for Copy Control and Other Applications a. Capture Oligomers Comprising a Capture Sequence and a Complement Thereof In some embodiments, a capture oligomer is provided that comprises a capture sequence, an internal extension blocker, a complement of the capture sequence, and a target-hybridizing sequence, wherein the complement of the capture sequence is configured to anneal to the capture sequence in the absence of an extended target sequence annealed to the target-hybridizing sequence and the complement of the capture sequence. As illustrated for an exemplary capture oligomer in FIGS. 1A-1C, such capture oligomers can be captured in a target-dependent manner, in that the capture sequence is initially annealed to the complement of the capture sequence (C') (FIG. 1A) but becomes available for binding upon extension of a target polynucleotide through C' (FIG. 1B). The internal extension blocker prevents extension of the target along the capture sequence itself. The target-capture oligomer extension product is thus susceptible to binding to a secondary capture reagent, which comprises a complement of the capture sequence and a binding partner or solid substrate (FIG. 1C). Meanwhile, any unbound capture oligomer does not serve as an extension template, so that C' remains annealed to the capture sequence, and the unbound capture oligomer does not substantially interact with the secondary capture reagent. Therefore, unbound capture oligomer will substantially remain in the original solution after isolation of complexes of the target-capture oligomer extension product, which can be accomplished using appropriate standard techniques based on the identity of the binding partner (e.g., biotin) or solid substrate (e.g., magnetic beads). A complex of target and capture oligomer associated with a bead is illustrated schematically in FIG. 2A and elution of the target from the bead is illustrated in FIG. 2B.

Such capture oligomers and combinations thereof with appropriate secondary capture reagents are useful in any application where capture, limited capture, or copy control is desirable, and also where incorporation of additional sequence is desirable. The capture oligomers described herein that have extendable 3' ends can be used as an amplification oligomer (e.g., primer), for example, along with an amplification primer, target strand or amplicon strand that have an orientation the reverse of the capture oligomer, to generate a extension products or amplicon which can then be isolated by contacting the complex formed with the secondary capture reagent and performing appropriate isolation steps. In other embodiments, the capture oligomer is not used as an amplification oligomer, or is not used in multiple rounds of extension, and an amplicon or natural DNA or RNA can simply be captured by annealing to the capture oligomer (and optionally or where appropriate, additional oligomers discussed herein such as a complementary oligomer or a displacer oligomer plus a reverse amplification oligomer, which can facilitate target-dependent displacement of the complement of the capture sequence as discussed in detail elsewhere herein), performing an extension step with a polymerase, and then contacting the extended complex with the secondary capture reagent and performing appropriate isolation steps. In either case, the amount of secondary capture reagent can be chosen to set the specific or maximum amount desired for capture. Furthermore, amounts of both the capture oligomer as well as the secondary capture reagent can be chosen to set the specific or maximum amount desired for capture, e.g., the amount of capture oligomer may be less than the amount of the target polynucleotide and the amount of the secondary capture reagent may be less than the amount of the capture oligomer.

An exemplary formula for a capture oligomer according to this disclosure is

5'-A1-C-L-B-A2-C'-A3-RB-A4-THS-X-3' wherein A1 is an optionally present first additional sequence;

C is the capture sequence,
L is an optionally present linker,
B is the internal extension blocker,
A2 is an optionally present second additional sequence,
C' is the complement of the capture sequence,
A3 is an optionally present third additional sequence,
RB is an optionally present reversible extension blocker,
A4 is an optionally present fourth additional sequence,
THS is the target-hybridizing sequence; and
X is an optionally present blocking moiety.

Figure 3:
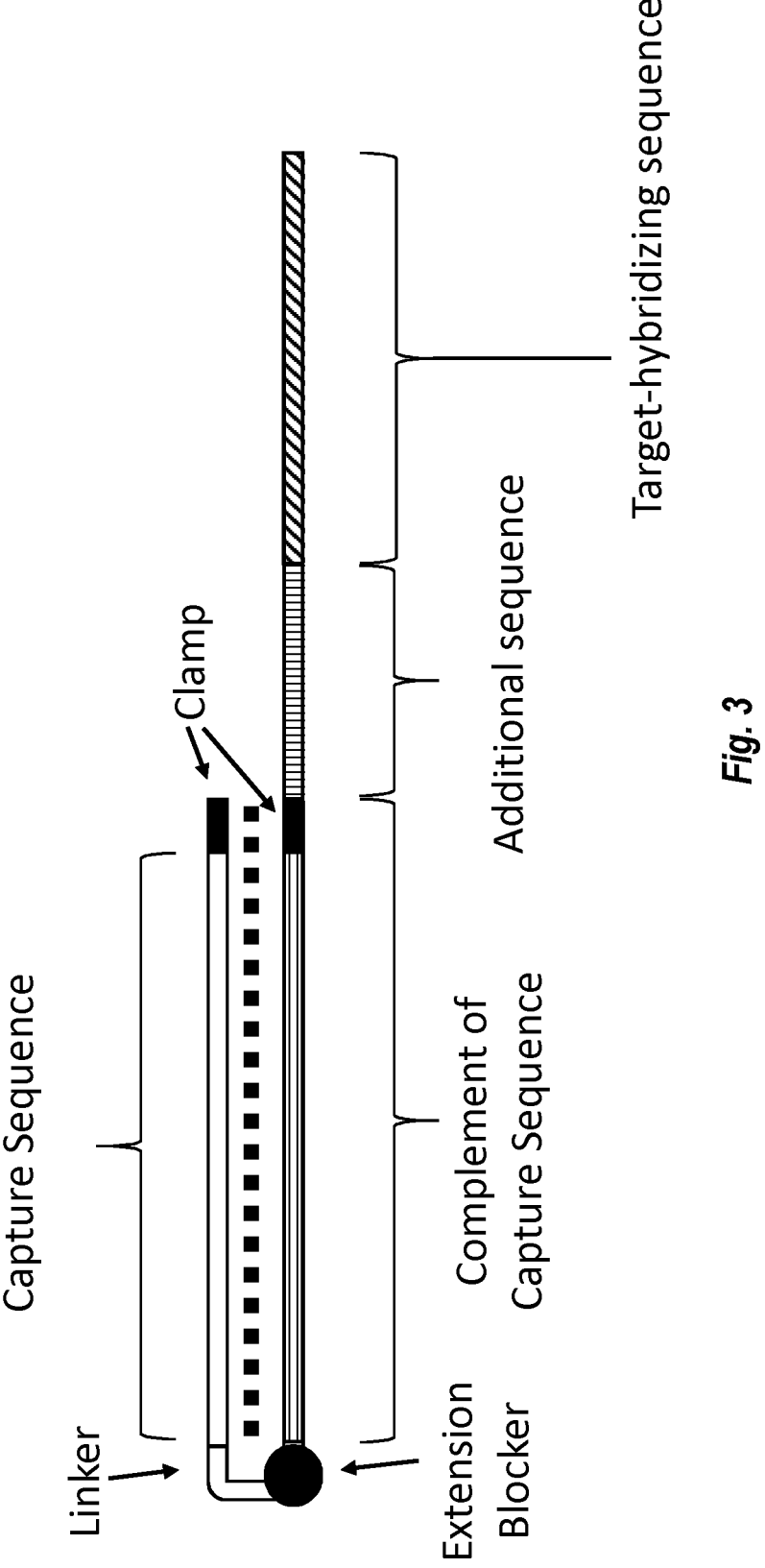
FIG. 3 illustrates an embodiment of a capture oligomer according to the disclosure comprising a stabilizing (clamp) sequence as a first additional sequence, a capture sequence, a linker, an internal extension blocker, a complement of the capture sequence, a stabilizing (clamp) sequence as a third additional sequence, a fourth additional sequence, and a target-hybridizing sequence.

In embodiments described herein including but not limited to those in accordance with the formula above, the ordinal numbers (first, second, third, and fourth) preceding each additional sequence are used simply to permit specific reference to each possible individual additional sequence and do not necessarily imply that any other additional sequences are present. Thus, a capture oligomer may comprise any one or any combination of two or more of the additional sequences, for example, only a fourth additional sequence; a third and a fourth additional sequence; a first, third, and fourth additional sequence; etc. Furthermore, any additional sequence may comprise multiple elements (e.g., a barcode and a primer binding site, or either or both of these plus a further sequence) or consist of a single element.

Where present, the first additional sequence can comprise an arbitrary sequence or one or more bases useful, e.g., to protect the 5' end of the capture sequence or function as a cleavage site, enzyme recognition site (e.g., for a restriction endonuclease) or a stabilizing sequence used for stabilizing a duplex and/or aligning the register of duplex regions (e.g., clamp). A capture oligomer comprising clamp sequences is illustrated in FIG. 3.

The capture sequence may comprise any sequence suitable for use as a capture sequence, such as any of the capture sequence embodiments described herein, including in the embodiments set forth above and the Oligomer elements section below.

Where present, the linker may be a sequence or non-sequence element or a combination thereof. The linker can provide flexibility to facilitate self-hybridization of the complement of the capture sequence to the capture sequence, and may adopt a loop-like conformation (e.g., substantially single-stranded when the linker is a sequence element) when the complement of the capture sequence is hybridized to the capture sequence. Exemplary non-sequence linkers include alkyl, alkenyl, amido and polyethylene glycol groups [(—CH$_2$CH$_2$O—)$_n$] with exemplary lengths of 3, 6, 12 or 18 or more atoms. Additional linker embodiments are provided elsewhere herein.

The internal extension blocker is an element that is not traversed by a DNA polymerase and thus prevents extension of a strand complementary to the strand of which it is a part. In some embodiments, the internal extension blocker is an abasic site, a chemically modified nucleotide, a non-natural nucleotide (e.g., isoC or isoG or other non-natural nucleotides described elsewhere herein; to be an effective blocker, the complementary non-natural nucleotide must not be present in the reaction mixture, e.g., no isoG if isoC is the blocker and vice versa), or a non-sequence element (e.g., any of the non-sequence linkers discussed above). A non-sequence linker may function as the internal extension blocker, or a separate linker and internal extension blocker may be present. Where a non-natural base such as isoC or isoG is used as the internal extension blocker, the complementary base is not provided so that the DNA polymerase will not traverse the position of the modified base.

Where present, the second additional sequence can comprise a tag, e.g., a mixed-nucleotide element as discussed below. In some embodiments, the second additional sequence comprises a cleavage site or a sequence used for stabilization and/or aligning the register of duplex regions (e.g., clamp sequence), for example when used in combination with a corresponding complementary sequence in another additional sequence.

The complement of the capture sequence may comprise a complement of any sequence suitable for use as a capture sequence, such as a complement of any of the capture sequence embodiments described herein, including in the embodiments set forth above and the Oligomer elements section below. In some embodiments, the complement of the capture sequence has a level of complementarity to the capture sequence of at least 80%, 85%, 90%, 95%, 97%, 98%, 99%, or 100%. Further, the complement of the capture sequence can complementary to only a portion of the capture sequence, for example to 50%, 60%, 70%, 80% or 90% of the capture sequence.

Where present, the third additional sequence may comprise a tag or a cleavage site or a sequence used for stabilization and/or aligning the register of duplex regions (e.g., clamp sequence), for example when used in combination with the corresponding complementary sequence in the first additional sequence. Complementary clamp sequences can render self-hybridization more energetically favorable and/or help keep the complementary regions C and C' in the desired register (alignment) and can improve capture oligomer performance as demonstrated in the examples. A capture oligomer comprising clamp sequences is illustrated in FIG. 3. In some embodiments, the third additional sequence comprises an adaptor or tag such as a sequence that can be used as a binding site for a primer (including a sequencing primer), anchor oligomer or probe binding site in subsequent reactions or steps, or a cleavage or enzyme binding site (e.g., for a restriction endonuclease), or as a barcode or other tag, e.g., to identify the source of a sample or molecule and facilitate approaches involving pooling, such as highly parallel sequencing. Such a sequence may be part of the third additional sequence along with a stabilizing (e.g., clamp) sequence.

Where present, a reversible extension blocker can be used to limit extension of a complementary strand along the capture oligomer during a first period, e.g., to maintain specificity of binding of the target-hybridizing sequence (THS) for the target polynucleotide where the capture oligomer is serving as an amplification oligomer. Exemplary reversible extension blockers include IsoG and IsoC and others described elsewhere herein, which can be unblocked by adding the complementary nucleotide (e.g., IsoC for IsoG and vice versa). Where a reversible extension blocker is used, an element different from the reversible extension blocker should be used as the internal extension blocker 5' of the complement of the capture sequence. A reversible extension blocker can also be used in an amplification oligomer (e.g., a reverse amplification primer in addition to the capture oligomer in an extension/amplification reaction), placed 5' of the THS and 3' of any additional sequence that is present. As described above, this can, among other advantages, maintain specificity of binding of the THS of the amplification oligomer for the target polynucleotide during an amplification process. The reversible extension blocker can be reversed after amplication and the complement to the additional sequence can be produced with a single extension step, thus incorporating the additional sequence into the amplicon. If the capture oligomer also comprises a reversible extension blocker, it can also be optionally reversed and the complement of the capture oligomer produced up to the internal extension blocker (as described above) concurrently with the like process in the amplification oligomer. This single extension step can optionally be performed in the same reaction mixture as the amplification reaction. This represents a rapid and simple method to maintain specificity while still incorporating additional sequence into a product (e.g., can be used for addition of adaptors in a sequencing library).

Where present, the fourth additional sequence may comprise an adaptor or tag, e.g., that functions as a binding-site sequence for a primer, probe, anchor oligo or the like, or as a barcode or other tag, e.g., to identify the source of a sample or molecule and facilitate approaches involving pooling, such as highly parallel sequencing. Such a sequence may be part of the fourth additional sequence along with a stabilizing sequence, aligning sequence, cleavage site, or enzyme binding site. In some embodiments, the fourth additional sequence comprises a stabilizing or aligning sequence.

In any of the foregoing embodiments where any of the described additional sequences (or a complement thereof formed by extension along the additional sequence) comprises a tag that is useful for downstream processes (e.g., addition of an adaptor useful for library preparation, clonal amplification, sequencing or data analysis), combining tag addition with target capture can streamline the overall workflow.

The target-hybridizing sequence may be any sequence of sufficient length and complementarity to hybridize to a given target, such as any of the target-hybridizing sequence embodiments described herein, including in the embodiments set forth above and the Oligomer elements section below.

Where present, the blocking moiety may be any moiety that prevents extension of the 3' end by a polymerase. Exemplary blocking moieties are described in detail elsewhere herein. The blocking moiety can prevent extension and subsequent capture of dimers of capture oligomers that may otherwise occur, e.g., where the concentration of a capture oligomer is high and/or the target-hybridizing sequence has some potential to dimerize. See FIG. 6.

i. Combinations

In some embodiments, a combination comprising a capture oligomer according to the disclosure and one or more additional oligomers is provided. The additional oligomers can comprise any of the following, or any combination of two or more of the following: a complementary oligomer for use with capturing a target molecule (which may be circular) without having the capture oligomer bind to a site comprising the 3' end of the target (see FIGS. 11A-B for an illustration of this combination and use thereof to capture a circular target molecule); an amplification oligomer, e.g., that binds the target polynucleotide in a reverse orientation relative to the capture oligomer; a pair of amplification oligomers, e.g., configured to amplify the target; a secondary capture reagent, e.g., comprising a complement of the capture sequence and a binding partner or a solid support; a splint oligomer; a blocker oligomer; or a displacer oligomer. Such additional oligomers are described in detail elsewhere herein. A combination may also comprise one or more additional capture oligomers, e.g., for performing multiplexed capture of multiple target polynucleotides. The additional capture oligomers may be accompanied by further additional oligomers such as appropriate reverse amplification oligomers, displacer oligomers, blocker oligomers, etc. Where a plurality of capture oligomers are used, they may have identical or sufficiently similar capture sequences so that a single secondary capture reagent can be used. Alternatively, they may have different capture sequences, e.g., so that if one target is present in high abundance, its resulting complex with an extended capture oligomer will not saturate a secondary capture reagent to the exclusion of a lower-abundance target complex.

In some embodiments, a combination comprises a capture oligomer described herein including a complement of the capture sequence, at least a second, third, or fourth additional sequence, and other elements, and a complementary oligomer comprising in the 5' to 3' direction, a target-hybridizing sequence and a complement of at least a portion of the second, third, or fourth additional sequence. See FIG. 11A. The target-hybridizing sequence of the complementary oligomer should bind to a portion of the target near (to the 3' side, according to the orientation of the target) to the target of the target-hybridizing sequence of the capture oligomer. The complement of at least a portion of the second or third additional sequence should be configured so that it anneals to the capture oligomer in a target-dependent manner, i.e., it should not anneal in the absence of the target. The ternary complex of target, capture oligomer, and complementary oligomer is a substrate for extension of the 3' end of the complementary oligomer by a polymerase, and displacement of the capture sequence from the complement of the capture sequence through such extension renders it available for capture using a secondary capture reagent.

b. Combinations Comprising a Capture Oligomer and a Complementary Oligomer

In some embodiments, a combination comprising a capture oligomer and a complementary oligomer is provided, wherein: (a) the capture oligomer comprises, in the 5' to 3' direction: a capture sequence comprising first and second portions, an internal extension blocker, a spacer sequence comprising first and second portions, and a target-hybridizing sequence; and (b) the complementary oligomer comprises, in the 3' to 5' direction: a complement of the second portion of the capture sequence, and a complement of at least the first portion of the spacer sequence, wherein the complement of the second portion of the capture sequence and the complement of the first portion of the spacer sequence are configured to anneal simultaneously to the capture oligomer in the absence of a complement of the spacer sequence. See FIG. 10A for an illustration of such a combination and use thereof.

Such a capture oligomer may have the formula:

$$5'\text{-}A1\text{-}C1\text{-}C2\text{-}B\text{-}A2\text{-}S1\text{-}S2\text{-}A3\text{-}RB\text{-}A4\text{-}THS\text{-}X\text{-}3'$$

wherein A1 is an optionally present first additional sequence,

C1 is the first portion of the capture sequence,

C2 is the second portion of the capture sequence,

B is the internal extension blocker,

A2 is an optionally present second additional sequence,

S1 is the first portion of the spacer sequence,

S2 is the second portion of the spacer sequence,

A3 is an optionally present third additional sequence,

RB is an optionally present reversible extension blocker,

A4 is an optionally present fourth additional sequence,

THS is the target-hybridizing sequence, and

X is an optionally present blocking moiety.

The complementary oligomer may have the formula:

$$5'\text{-}S1'\text{-}A2'\text{-}L\text{-}C2'\text{-}X\text{-}3'$$

wherein S1' is the complement of the first portion of the spacer sequence,

A2' is an optionally present complement of a second additional sequence which is optionally present in the capture oligomer;

L is an optionally present linker,

C2' is the complement of the second portion of the capture sequence, and

X is an optionally present blocking moiety.

FIG. 10A illustrates an exemplary combination of capture oligomers in accordance with the description above. In the absence of target, the complementary oligomer is annealed to the capture oligomer. Upon hybridization to a target followed by extension of the 3' end, the complementary oligomer is displaced. The capture sequence remains substantially single stranded due to the extension, displacement of the complementary oligomer and creation of a duplex in the "S" region (which blocks reannealing of the complementary oligomer), and can be contacted by a secondary capture reagent comprising a complement of the capture sequence and a binding partner or bead, facilitating subsequent isolation steps.

FIG. 13 illustrates a different exemplary workflow for using a combination of capture oligomers in accordance with the description above, in which the complementary oligomer is provided after extension of the target along the capture oligomer rather than before annealing the capture oligomer to the target. Further, in the exemplary workflow depicted by FIG. 13, a reverse amplification oligomer is provided which is utilized in conjunction with the capture oligomer in an amplification reaction (e.g., PCR) to yield product in which the spacer region is incorporated into the amplicon. This spacer region is an arbitrary sequence. In some embodiments of this workflow the complementary oligomer is provided during the amplification reaction. In this mode it improves the specificity of the amplification reaction by blocking at least a portion of the spacer and capture sequences during the annealing phase of the reaction and still annealing to the capture oligomer in the absence of a complement of the spacer sequence after the amplification reaction has been completed.

Where present, the first additional sequence can comprise a tag. In some embodiments, the first additional sequence comprises one or more bases useful, e.g., to protect the 5' end of the capture sequence or function as a cleavage site or enzyme recognition site (e.g., restriction endonuclease).

The first and second portions of the capture sequence form a capture sequence, e.g., any sequence suitable for use as a capture sequence, such as any of the capture sequence embodiments described herein, including in the embodiments set forth above and the Oligomer elements section below.

The internal extension blocker is an element that is not traversed by a DNA polymerase. In some embodiments, the internal extension blocker is an abasic site, a chemically modified nucleotide, a non-natural nucleotide (e.g., isoC or isoG or any other non-natural nucleotide described herein that does not template addition of a natural nucleotide), or a non-sequence element (e.g., any of the non-sequence linkers discussed above). A non-sequence linker may function as the internal extension blocker. Where a modified base such as isoC or isoG is used as the internal extension blocker, the complementary base is not provided so that the DNA polymerase will not traverse the position of the modified base.

Where present, the second additional sequence comprise an adaptor or tag, e.g., that functions as a binding-site sequence for a primer, probe, anchor oligo or the like, or as a barcode or other tag, e.g., to identify the source of a sample or molecule and facilitate approaches involving pooling, such as highly parallel sequencing. Such a sequence may be part of the second additional sequence along with a stabilizing sequence, aligning sequence, cleavage site, or enzyme binding site. In some embodiments, the second additional sequence comprises a stabilizing or aligning sequence.

The first and second portions of the spacer sequence form a spacer sequence. At least the first portion of the spacer sequence is responsible for binding the complementary oligomer. The spacer sequence is configured to serve as a template for extension when the target polynucleotide including its 3' end is annealed to the capture oligomer, wherein such extension results in displacement of the complementary oligomer, thereby rendering the capture sequence accessible to a secondary capture reagent. The spacer sequence is distinct from the target-hybridizing sequence, the capture sequence, and complements thereof—i.e., it should not substantially hybridize to any of these. The spacer sequence or its first or second portions may also comprise any elements set forth above with respect to second additional sequences.

Where present, the third additional sequence may comprise an adaptor or tag, e.g., that an arbitrary sequence or functions as a target binding-site sequence for that can be used as a primer, or probe, anchor oligo or the like binding site in subsequent reactions or steps (e.g., an adaptor), or as a barcode or other tag, e.g., to identify the source of a sample or molecule and facilitate approaches involving pooling, such as highly parallel sequencing. Such a target sequence may be part of the third additional sequence along with a clamp stabilizing sequence, aligning sequence, cleavage site, or enzyme binding site sequences. In some embodiments, the third additional sequence comprises a stabilizing or aligning clamp sequence.

Where present, a reversible extension blocker can be used to limit extension of a complementary strand along the capture oligomer during a first period, e.g., to maintain specificity of binding of the target-hybridizing sequence for the target polynucleotide where the capture oligomer is serving as an amplification oligomer. Exemplary reversible extension blockers include IsoG and IsoC and other members of pairs of non-natural nucleotides described elsewhere herein, which can be unblocked by adding the complementary nucleotide (e.g., IsoC for IsoG and vice versa). Where a reversible extension blocker is used, an element different from the reversible extension blocker should be used as the internal extension blocker 5' of the complement of the capture sequence.

Where present, the fourth additional sequence may comprise an adaptor or tag, e.g., that functions as a binding-site sequence for a primer, probe, anchor oligo or the like, or as a barcode or other tag, e.g., to identify the source of a sample or molecule and facilitate approaches involving pooling, such as highly parallel sequencing. Such a sequence may be part of the fourth additional sequence along with a stabilizing sequence, aligning sequence, cleavage site, or enzyme binding site. In some embodiments, the fourth additional sequence comprises a stabilizing or aligning sequence.

In any of the foregoing embodiments where any of the described additional sequences (or a complement thereof formed by extension along the additional sequence) comprises a tag that is useful for downstream processes (e.g., addition of an adaptor useful for library preparation, clonal amplification, sequencing or data analysis), combining tag addition with target capture can streamline the overall workflow.

The target-hybridizing sequence may be any sequence of sufficient length and complementarity to hybridize to a given target, such as any of the target-hybridizing sequence embodiments described herein, including in the embodiments set forth above and the Oligomer elements section below.

Where present, the blocking moiety may be any moiety that prevents extension of the 3' end by a polymerase. Exemplary blocking moieties are described in detail elsewhere herein. The blocking moiety can prevent extension and subsequent capture of dimers of capture oligomers that may otherwise occur, e.g., where the concentration of a capture oligomer is high and/or the target-hybridizing sequence has some potential to dimerize. See FIG. 6.

Turning to the complementary oligomer, the complement of the first portion of the spacer sequence serves to stabilize a complex of the complementary oligomer with a capture oligomer that has not served as a template for extension of a target polynucleotide. Although not necessary, the complementary oligomer may comprise a complement of the entire spacer sequence.

Where the complementary oligomer is used with a capture oligomer that comprises a second additional sequence, it can be useful to include a complement of the second additional sequence in the complementary oligomer to facilitate its binding to the capture oligomer.

Where present, the linker, which may be a sequence or non-sequence element as discussed above for linkers, can provide appropriate spacing, depending on the size and nature of the internal extension blocker in the capture oligomer, to facilitate simultaneous annealing of both the complement of the first portion of the spacer and the complement of the second portion of the capture sequence to the corresponding parts of the capture oligomer.

The complement of the second portion of the capture oligomer should have a length and content sufficient to anneal to the capture oligomer together with the complement of the first portion of the spacer sequence (and, if applicable, other parts of the complementary oligomer that complement sequences in the capture oligomer) but insufficient to anneal independently of the complement of at least the first portion of the spacer sequence. In other words, upon displacement of the complement of at least the first portion of the spacer sequence such as through extension of the target polynucleotide along the spacer sequence, the complement of the second portion of the capture sequence should dissociate because it lacks sufficient affinity to bind to the second portion of the capture sequence without the energetic contribution of additional hybridization by other parts of the oligomer.

Where present, the blocking moiety may be any moiety that prevents extension of the 3' end by a polymerase. Exemplary blocking moieties are described in detail elsewhere herein. The blocking moiety can prevent extension of the complementary oligomer along any sequence to which it binds, which may produce undesirable side products, primer dimers, etc.

i. Further Combinations; Kits and Reaction Mixtures

In some embodiments, a further combination is provided comprising one or more additional oligomers. The additional oligomers can comprise any of the following, or any combination of two or more of the following: a complementary oligomer for use with capturing a target molecule (which may be circular) without having the capture oligomer bind to a site comprising the 3' end of the target; an amplification oligomer, e.g., that binds the target polynucleotide in a reverse orientation relative to the capture oligomer; a pair of amplification oligomers, e.g., configured to amplify the target; a secondary capture reagent, e.g., comprising a complement of the capture sequence and a binding partner or a solid support; a splint oligomer; a blocker oligomer; or a displacer oligomer. Such additional oligomers are described in detail elsewhere herein. A combination may also comprise one or more additional capture oligomers, e.g., for performing multiplexed capture of multiple target polynucleotides, which may be accompanied by one or more additional appropriate complementary oligomers (and/or a complementary oligomer may be provided that binds two or more, or all of the capture oligomers). The additional capture oligomers may be accompanied by further additional oligomers such as appropriate reverse amplification oligomers, displacer oligomers, blocker oligomers, etc. Where a plurality of capture oligomers are used, they may have identical or sufficiently similar capture sequences so that a single secondary capture reagent can be used. Alternatively, they may have different capture sequences, e.g., so that if one target is present in high abundance, its resulting complex with an extended capture oligomer will not saturate a secondary capture reagent to the exclusion of a lower-abundance target complex.

2. Detailed Description of Oligomer Elements and Other Reagents and Components a. Oligomer Elements i. Capture Sequence Any capture sequence that can be bound by an appropriate complement may be used. In some embodiments, a capture sequence comprises a poly-A or poly-T sequence (e.g., at least 10, 12, 15, 20, 25, or 30 consecutive A residues, or at least 10, 12, 15, 20, 25, or 30 consecutive T residues). In some embodiments, a poly-A sequence comprises 25 or 30 consecutive A residues. In some embodiments, a poly-T sequence comprises 25 or 30 consecutive T residues. T residues include U residues for purposes of qualifying as a poly-T sequence unless otherwise indicated. In some embodiments, a capture sequence is an arbitrary sequence that does not occur in the target polynucleotide. The arbitrary sequence can be chosen or designed to yield the desired properties for a given process, e.g., chosen to yield the desired thermal stability, affinity and kinetic properties. In some embodiments, where the target polynucleotide is or comprises sequence from a gene, the capture sequence is an arbitrary sequence that does not occur in the genome of the gene. In some embodiments, where the target polynucleotide is or comprises sequence from an organism, the capture sequence is an arbitrary sequence that does not occur in the genome of the organism. In some embodiments, the capture sequence comprises 12, 13, 14, 15, 16, 17, 18, 19, 20, 21, 22, 23, 24, 25, 26, 27, 28, 29, 30, 31, 32, 33, 34, or 35 nucleotides. In some embodiments the capture sequence consists of 12, 13, 14, 15, 16, 17, 18, 19, 20, 21, 22, 23, 24, 25, 26, 27, 28, 29, 30, 31, 32, 33, 34, or 35 nucleotides.

ii. Complement of a Capture Sequence

Any sequence sufficiently complementary to a capture sequence to bind it with an appropriate level of specificity and stability may be used as a complement of a capture sequence. In some embodiments, the complement of a capture sequence comprises residues complementary to at least 70%, 75%, 80%, 85%, 90%, 95%, 97%, 98%, 99%, or 100% of the capture sequence. In some embodiments, the complement of the capture sequence is configured to form a complex with the capture sequence having a melting temperature in the range of 40° C. to 75° C., e.g., 40° C. to 50° C., 50° C. to 60° C., or 60° C. to 75° C., under hybridization conditions such as 0.4-1 M monovalent cation, 0-10 mM divalent cation (e.g., magnesium), 10-100 mM buffer (e.g., citrate, phosphate, Tris, borate) pH 5-9 and 0-1 mg/mL BSA.

iii. Additional Sequences

As set forth herein, a capture oligomer can comprise one or more additional sequences, e.g., that provide additional functionality to the capture oligomer and/or related extension products.

A capture oligomer can comprise stabilizing (e.g., clamp) sequences, e.g., 5' of a capture sequence and 3' of a complement of the capture sequence, that may render self-hybridization more energetically favorable and/or help to align sequences of the capture oligomer and complement to the capture oligomer as desired. In some embodiments, clamp sequences comprise G and/or C residues, e.g., alternating G and C residues. Exemplary clamp sequences are 3, 4, 5, 6, 7, 8, 9, or 10 nucleotides in length. In some embodiments, clamp sequences comprise one or more affinity-enhancing modifications as described elsewhere herein.

In some embodiments, an additional sequence is a tag. A tag may be provided to spatially separate other elements or to confer another property.

In some embodiments, an additional sequence provides an adaptor, e.g., a binding site for a probe or primer. For example, an additional sequence (or its complement formed by extension along the additional sequence) can serve as a binding site for a universal primer or a sequencing primer. As such, including an additional sequence can streamline processes such as sequencing library preparation where adaptor sequences need to be added by combining adaptor addition with target capture.

In some embodiments, an additional sequence provides a tag sequence, e.g., a barcode sequence that facilitates identification of a molecule as coming from a particular source or as having been processed in a particular way.

In some embodiments, an additional sequence provides one or more enzyme recognition sites, e.g., restriction sites. As such, the additional sequence can facilitate cleavage and subsequent ligation or molecular cloning procedures. Another example of an enzyme recognition site is a site recognized by a site-specific recombinase.

In some embodiments, an additional sequence comprises an aligning sequence, such as a mixed-nucleotide segment. A mixed-nucleotide segment is not a consecutive series of the same nucleotide. In some embodiments, the aligning sequence or mixed nucleotide segment is immediately 3' of the internal extension blocker, such that an extension product formed using an amplification oligomer that binds in a reverse orientation to a capture oligomer comprising the aligning sequence will have the complement of the mixed nucleotide segment at its 3' end. In some embodiments, an aligning sequence or mixed nucleotide segment comprises 4, 5, 6, 7, or 8 nucleotides. In some embodiments, each nucleotide in a mixed-nucleotide segment is different (e.g., has a different base-pairing specificity) from each of its immediate neighbors. An aligning sequence or mixed-nucleotide segment can useful for preparing a substrate for a circularization reaction as described elsewhere herein.

iv. Linker

In some embodiments, a linker comprises a sequence. A linker sequence may be arbitrary or have any of the features discussed with respect to additional sequences. In some embodiments, a linker comprises non-sequence elements. Exemplary non-sequence linker elements include alkyl, alkenyl, amido and polyethylene glycol groups with chain lengths of 3-20 atoms or more or 3, 4, 5, 6, 7, 8, 9, 10, 11, 12, 13, 14, 15, 16, 17, 18, 19, 20 or more atoms) or 2, 3, 4, 5, 6, 7, 8, 9, 10, 11, 12, 13, 14, or 15 repeating units, e.g., —$CH_2CH_2O$— units.

v. Internal Extension Blocker

Various capture oligomers described herein comprise an internal extension blocker. Any moiety that when present in a template prevents a polymerase from continuing an extension reaction along the template may be used as an internal extension blocker. Depending on the polymerase, exemplary internal extension blockers may comprise abasic sites, chemically modified nucleotides, non-natural nucleotides such as IsoG or IsoC (to be an effective blocker, the complementary non-natural nucleotide must not be present in the reaction mixture, e.g., no isoG if isoC is the blocker and vice versa), a non-sequence linker element as discussed above, or combinations thereof.

In some embodiments, the internal extension blocker comprises an abasic site. An abasic site is a position in a nucleic acid where a nucleobase is missing from the position where it would usually be.

In some embodiments, the internal extension blocker comprises a chemically modified nucleotide. Various chemically modified nucleotides are known that block extension by a DNA polymerase, such as alkylated nucleotides and modified nucleotides formed by reaction of a nucleotide with certain DNA-damaging agents, e.g., chemotherapy drugs. Other modified nucleotides useful as internal extension blockers comprise those with backbone modifications, sugar modifications, base modifications and combinations thereof.

In some embodiments, the internal extension blocker comprises a non-natural nucleotide, such as IsoG (6-amino-2-ketopurine) or IsoC (2-amino-4-ketopyrimidine). IsoG and IsoC are nucleotides that do not form Watson-Crick base pairs with any of the four natural DNA nucleotides but do pair with each other. See, e.g., Hirao et al., *Proc Jpn Acad Ser B Phys Biol Sci.* 2012; 88(7): 345-367. Thus, if (i) a template contains IsoG and (ii) an IsoC nucleotide is not available, or vice versa, extension will be blocked because the polymerase will not have anything to incorporate opposite the IsoG or IsoC.

In some embodiments, the internal extension blocker comprises a non-sequence linker element, e.g., alkyl, alkenyl, amido and polyethylene glycol groups with chain lengths of 3-20 atoms or more or 3, 4, 5, 6, 7, 8, 9, 10, 11, 12, 13, 14, 15, 16, 17, 18, 19, 20 or more atoms) or 2, 3, 4, 5, 6, 7, 8, 9, 10, 11, 12, 13, 14, or 15 repeating units, e.g., —$CH_2CH_2O$— units.

vi. Reversible Extension Blocker

In some embodiments, a capture oligomer comprises a reversible extension blocker. A reversible extension blocker is an element that when present in a template prevents a polymerase from continuing an extension reaction along the template until the block is reversed. Examples of reversible extension blockers include members of non-natural base pairs, such as IsoG and IsoC, which are discussed above. See, e.g., Hirao et al., supra. A block based on IsoG may be reversed by providing an IsoC nucleotide triphosphate so that extension can continue, and vice versa. A general illustration of using a reversible extension blocker is provided in FIG. 7A. In some embodiments an amplification oligomer comprises a reversible extension blocker. Such an amplification oligomer can be used separately in an extension or amplification reaction or concurrently with a capture oligomer without a reversible extension blocker or concurrently with a capture oligomer with a reversible extension blocker. If an amplification oligomer and a capture oligomer both comprising a reversible extension blocker are used in the same process, the reversing step of each can be performed concurrently or separately.

vii. Target-Hybridizing Sequence

Various capture oligomers according to this disclosure comprise a target-hybridizing sequence. A target-hybridizing sequence may hybridize to a naturally occurring sequence, e.g., in a nucleic acid (such as a DNA or RNA) of an organism, or it may hybridize to a binding site or adaptor sequence, e.g., added to an amplicon using an amplification oligomer comprising the adaptor sequence or using ligation. In some embodiments, a target-hybridizing sequence has a length in the range of about 10-60 bases, about 12-50 nucleotides, about 12-40 nucleotides, about 12-35 nucleotides, about 12-30 nucleotides, about 15-30 nucleotides, or about 17-25 nucleotides. Various algorithms for selecting appropriate sequences to use as target-hybridizing sequences are available to one of ordinary skill in the art.

In some embodiments, a target-hybridizing sequence is configured to bind to a site comprising the 3' end of the target. Such binding creates a substrate for extension of the 3' end, which for various oligomers and combinations described herein will result in strand displacement that renders a capture sequence available for binding to a secondary capture reagent, as discussed in more detail elsewhere herein.

In some embodiments, a target-hybridizing sequence is configured to bind to an internal site within a target. Such binding can be used in combination with a displacer or other additional oligomer or more generally in capture methods described elsewhere herein that do not involve extending the 3' end of a target.

viii. Blocking Moiety

In some embodiments, a capture oligomer or other oligomer described herein comprises a blocking moiety at its 3' end. A blocking moiety prevents extension of the oligomer of which it is a part along a template. Exemplary blocking moieties include alkyl groups, non-nucleotide linkers, alkane-diols (e.g., 3'-hexanediol residues), and cordycepin. Further examples of blocking moieties include a 3'-deoxy nucleotide (e.g., a 2',3'-dideoxy nucleotide); a 3'-phosphorylated nucleotide; a fluorophore, quencher, or other label that interferes with extension; an inverted nucleotide (e.g., linked to the preceding nucleotide through a 3'-to-3' phosphodiester, optionally with an exposed 5'-OH or phosphate); or a protein or peptide joined to the oligonucleotide so as to prevent extension. Use of an exemplary capture oligomer with a blocking moiety at its 3' end is illustrated schematically in FIG. 5. Such a capture oligomer can be useful, e.g., in combination with an appropriate reverse amplification oligomer (which may also provide an additional sequence to be incorporated into the target), to isolate a single-stranded target. A capture oligomer with a blocking moiety at its 3' end can also provide the benefit of preventing extension and subsequent capture of dimerized capture oligomers. See FIG. 6 for an exemplary illustration.

ix. Affinity-Enhancing Modifications

In some embodiments, a capture oligomer or other oligomer described herein comprises one or more affinity-enhancing modifications, e.g., in a portion of sequence responsible for binding another molecule, such as a target polynucleotide or a secondary capture reagent. Affinity-enhancing modifications are useful to ensure that the oligomer competes effectively for its target even when a competing oligomer that contains a sequence that would bind the same target are present, e.g., unincorporated primers from an amplification reaction. The competing oligomer may be present in excess relative to the capture oligomer and/or the target, meaning that competing effectively by virtue of relatively higher affinity for the target would have a significant effect on how much of the capture oligomer binds its target instead of being outcompeted.

Exemplary affinity-enhancing modifications include 5-methylation of cytosine; use of 2-aminopurine; 2'-fluoro modifications; 2'-methoxy modifications; C-5-propyne; and constrained ethyl (cEt) substitutions. Embodiments of oligomers that can affect stability of a hybridization complex include PNA oligomers, LNA (Locked Nucleic Acids, which stabilize nucleotides in certain conformations and reduce the extent to which entropy detracts from the free energy of hybridization), or oligomers that affect the overall charge, charge density, or steric associations of a hybridization complex, including ZNA (Zip Nucleic Acids), oligomers that contain charged linkages (e.g., phosphorothioates) or neutral groups (e.g., methylphosphonates).

b. Secondary Capture Reagents

In some embodiments, a secondary capture reagent is present in a combination or is used with a capture oligomer described herein. A secondary capture reagent may comprise a complement of the capture sequence in the capture oligomer and (i) a binding partner or (ii) a solid support, e.g., a bead (such as a magnetic bead), well, planar surface, packed column, fiber, resin or gel, to facilitate isolation of a complex comprising the secondary capture reagent and a capture oligomer, which may be hybridized to a target polynucleotide and/or have undergone extension to include a copy of the target polynucleotide sequence.

Any suitable binding partner, including any binding partner described herein, e.g., in the definition section, may be used. In some embodiments, the binding partner is biotin.

c. Blocker Oligomer

In some embodiments, a blocker oligomer is present in a combination or is used with a capture oligomer described herein. A blocker oligomer generally comprises a complement of an additional sequence or at least a portion thereof, and can be used to facilitate specific hybridization of a target-hybridizing sequence of the capture oligomer (or an amplification oligomer used to prepare an amplicon for capture by a capture oligomer) to its target by competing for hybridization to the complement of the additional sequence (i.e., blocking the additional sequence in the capture oligomer from hybridizing to its complement, or at least reducing its ability to do so). See FIG. 9 for an illustration of the general principles regarding use of a blocker oligomer in an amplification reaction. A blocker oligomer may comprise a blocking moiety at its 3' end, e.g., where extension of the blocker oligomer would be undesirable. Using a blocker oligomer can reduce the extent to which any products of mispriming undergo further amplification during an amplification reaction in that substantially only targets comprising a complement of the target hybridizing sequence are good substrates for hybridization to the capture oligomer or the amplification oligomer regardless of the presence of the complement of additional sequence.

d. Splint Oligomer

In some embodiments, a splint oligomer is present in a combination or is used with a capture oligomer described herein. A splint oligomer can be used to facilitate ligation of an extension product to circularize it. See FIG. 12. A splint oligomer may comprise a complement of a sequence not present in the capture oligomer; a second additional sequence present in the capture oligomer; and a complement of the capture sequence of the capture oligomer. Optionally, the splint oligomer may further comprise a fourth additional sequence present in the capture oligomer.

The splint oligomer is configured to anneal to a target polynucleotide that has been extended from its 3' end along a capture oligomer comprising an optional fourth additional sequence, a complement of a capture sequence, and a second additional sequence in the 3' to 5' direction, followed by an internal extension blocker. As such, the complement of the second additional sequence is at the 3' end of the target polynucleotide.

The splint oligomer's complement of the sequence not present in the capture oligomer is complementary to a sequence at the 5' end of the target polynucleotide (i.e., distal to the site bound by the capture oligomer), which may be an adaptor sequence added during amplification or may correspond to some or all of the amplification oligomer used to amplify the target polynucleotide.

The second additional sequence is configured to anneal to a complement thereof located at the 3' end of the target polynucleotide. The complement of the capture sequence and, where present, the fourth additional sequence also anneal to corresponding sequences near the 3' end of the target polynucleotide. The target polynucleotide when annealed to the splint oligomer becomes a substrate for circularization by ligation. See FIG. 12 for an illustration of an exemplary splint oligonucleotide in accordance with this description and use thereof for circularization. Circularizing a target molecule can be useful, e.g., for preparing the target for use in a rolling circle amplification procedure.

e. Displacer Oligomer

In some embodiments, a displacer oligomer (e.g., displacer primer) is present in a combination or is used with a capture oligomer described herein. A displacer oligomer can be used to displace an extended capture oligomer from a template strand of a target polynucleotide. For example, see FIGS. 8A and 8B. In some embodiments, a displacer oligomer is provided in combination with a capture oligomer having a target-hybridizing sequence that binds to an internal site within a target (e.g., a site within a target polynucleotide, an amplicon or an additional sequence incorporated during a previous extension or amplification step), which is positioned relative to the binding site of the displacer oligomer so as to facilitate displacement by extension of the displacer oligomer.

In some embodiments, a combination comprising a displacer oligomer (e.g., displacer primer) and a capture oligomer further comprises an amplification oligomer (e.g., primer) that is configured to bind to an extended capture oligomer (thus having a reverse binding orientation relative to the capture and displacer oligomers). Extension of the amplification oligomer may result in displacement of a complementary oligomer or a capture sequence, depending on the configuration of the capture oligomer and/or combination, thus rendering the capture sequence of the extended capture oligomer available to interact with a secondary capture reagent. As described elsewhere, the amplification oligomer may also be used to incorporate an additional sequence (e.g., tag, such as an adaptor sequence) on the end of the extended capture oligomer distal to the original capture oligomer sequence (see FIG. 8A, for example, wherein the complement to the additional sequence of the amplification oligomer is created via further extension of the extended and displaced capture oligomer). Thus, in a single step one-pot process that can be performed simply and quickly, a product can be made that comprises additional sequence at both ends as well as an accessible capture sequence.

f. Amplification Oligomer

In some embodiments, an amplification oligomer (e.g., primer) is present in a combination or is used with a capture oligomer described herein. For example, the amplification oligomer may be configured to anneal in an opposite orientation to the target-hybridizing sequence of a capture oligomer. For an example, see FIG. 4A. The amplification oligomer may comprise a target-hybridizing sequence, and optionally, an additional sequence 5' of the target-hybridizing sequence. The additional sequence would become incorporated upon further extension of the strand comprising the extended capture oligomer, using the additional sequence of the amplification oligomer as a template, and may provide one or more tags, which may comprise one or more adaptor sequences. In some embodiments, an amplification oligomer comprises a reversible internal extension blocker, e.g., 3' of one or more elements other than the THS, such as between the target-hybridizing sequence and an additional sequence 5' of the target-hybridizing sequence. The combination comprising an amplification oligomer may further comprise one or more further oligomers, such as a displacer oligomer, splint oligomer, etc., e.g., as described elsewhere herein.

g. Kits

In some embodiments, a kit is provided comprising a capture oligomer or combination thereof, such as any of the capture oligomers or combinations described herein and further comprising one or more additional elements, such as a reagent, buffer, or other substance for use with the capture oligomer or combination thereof, and/or instructions for using the capture oligomer or combination thereof. Exemplary reagents include dNTPs, a DNA polymerase, a sodium salt, a magnesium salt, and beads, e.g., comprising a complement of the capture sequence or second binding partner that binds to a first binding partner present along with a complement of the capture sequence in a secondary capture reagent.

In some embodiments, a capture oligomer is present in a kit in an amount in the range of $10^7$ to $10^{13}$ molecules/reaction, $10^9$ to $10^{12}$ molecules/reaction, or $10^{10}$ to $10^{12}$ molecules/reaction.

In some embodiments, the secondary capture reagent comprising the complement of the capture oligomer is present in a kit in the range of $10^3$ to $10^{14}$ molecules/reaction, or $10^3$ to $10^9$ molecules/reaction, or $10^5$ to $10^{13}$ molecules/reaction, or $10^5$ to $10^8$ molecules/reaction, or $10^6$ to $10^{13}$ molecules/reaction, or $10^6$ to $10^8$ molecules/reaction.

In some embodiments, a kit comprises a capture oligomer which is in a liquid, frozen, or lyophilized state.

In some embodiments, a kit comprises at least first and second containers comprising, respectively, a capture oligomer and one or more additional oligomers as described herein (e.g., a complementary oligomer, secondary capture reagent, or amplification, splint, blocker, second or displacer oligomer). Alternatively, such a combination of oligomers can be provided in a single container.

In some embodiments, a kit comprises a solid support/beads comprising a second binding partner (e.g., streptavidin) configured to bind the binding partner of the secondary capture reagent.

h. Compositions

Also provided are compositions comprising a capture oligomer or combination described herein. Any of the oligomers or combinations described herein may be present in a composition. In some embodiments, the composition is in the form of a lyophilizate or a solution.

In some embodiments, a reaction mixture is provided comprising a capture oligomer or combination thereof, such as any of the capture oligomers or combinations described herein. The reaction mixture may further comprise one or more target polynucleotides and/or one or more reagents (e.g., any reagent discussed herein in connection with a kit or method).

The reaction mixture may further comprise one or more target polynucleotides (e.g., any target discussed herein in connection with a method). In some embodiments, the target polynucleotide comprises a sequence from a DNA or RNA (e.g., genomic DNA or mRNA) of a target organism and an additional sequence, and the target hybridizing sequence of the capture oligomer is configured to anneal to the additional sequence of the target polynucleotide. The additional sequence may have been added in a previous reaction, such as an extension, ligation, or amplification reaction. For example, the additional sequence can be a sequence not present in the DNA or RNA of the target organism. Such an additional sequence may have been added in an earlier extension reaction using a primer comprising the additional sequence. This approach facilitates multiplex capture or reuse of a capture oligomer design with different targets to which the same additional sequence has been attached. In some embodiments, the composition comprises a plurality of target polynucleotides comprising (i) the additional sequence and (ii) different sequences from the DNA or RNA of the target organism, and the method comprises capturing the plurality of target polynucleotides.

3. Detailed Description of Methods of Capturing Polynucleotides

A method is provided of capturing a target polynucleotide from a composition, the method comprising:
contacting the target polynucleotide with a capture oligomer described herein that comprises a capture sequence and a complement of the capture sequence, wherein the target-hybridizing sequence of the capture oligomer anneals to the target polynucleotide at a site comprising the 3' end of the target polynucleotide. The method further comprises extending the 3' end of the target polynucleotide with a DNA polymerase with strand-displacement activity, thereby forming a complement of the complement of the capture sequence, which is annealed to the capture oligomer, such that the capture sequence of the capture oligomer is available for binding;
contacting the capture sequence of the capture oligomer with a secondary capture reagent comprising a complement of the capture sequence and (i) a binding partner or (ii) a solid support, thereby forming a complex comprising the target polynucleotide, the capture oligomer, and the secondary capture reagent; and isolating the complex from the composition, thereby capturing the target polynucleotide. Exemplary schemes illustrating the contacting and extending steps are shown in FIGS. 4A-B. In FIG. 4A, the THS of the capture oligomer binds a sequence at the 3' end of the target. In FIG. 4B, the THS of the capture oligomer binds an additional sequence at the 3' end of the target, e.g., that can be added in an earlier reaction.

Also provided herein is a method of capturing a target polynucleotide from a composition, the method comprising:
contacting the composition with a combination described herein comprising a capture oligomer and a complementary oligomer, wherein the target-hybridizing sequence of the capture oligomer anneals to the target polynucleotide or an additional sequence at a site comprising the 3' end of the target polynucleotide;
extending the 3' end of the target polynucleotide with a DNA polymerase with strand-displacement activity, thereby forming a complement of the spacer sequence, which is annealed to the capture oligomer, such that the complementary oligomer is displaced to an extent sufficient for the capture sequence of the capture oligomer to be available for binding; contacting the capture sequence of the capture oligomer with a secondary capture reagent comprising a complement of the capture sequence and (i) a binding partner or (ii) a solid support, thereby forming a complex comprising the target polynucleotide, the capture oligomer, and the secondary capture reagent; and
isolating the complex from the composition, thereby capturing the target polynucleotide. The complementary oligomer of the combination may be provided to the composition at any point before contacting the capture sequence of the capture oligomer with the secondary capture reagent, e.g., together with the capture oligomer or after extension of the target along the capture oligomer. See FIGS. 10 and 13 for illustrations of exemplary methods in accordance with this description.

Also provided herein is a method of capturing a target polynucleotide from a composition, the method comprising:
contacting the target polynucleotide with a capture oligomer or combination described herein, wherein the capture oligomer comprises a third or fourth additional sequence 5' of the target hybridizing sequence and 3' of the complement of the capture sequence or the second portion of the spacer sequence;
contacting the target polynucleotide with a second oligomer comprising a second target-hybridizing sequence 5' of a complement of at least a portion of the third or fourth additional sequence, wherein the capture oligomer and the second oligomer form a three-strand junction with the target polynucleotide;
extending the 3' end of the second oligomer with a DNA polymerase with strand-displacement activity, thereby forming a complement of the complement of the capture sequence or a complement of the spacer sequence, which is annealed to the capture oligomer, such that the capture sequence of the capture oligomer is available for binding;
contacting the capture sequence of the capture oligomer with a secondary capture reagent comprising a complement of the capture sequence and (i) a binding partner or (ii) a solid support, thereby forming a complex comprising the target polynucleotide, the capture oligomer, and the secondary capture reagent; and
isolating the complex from the composition, thereby capturing the target polynucleotide. In some embodiments of this method, the target polynucleotide is circular. See FIGS. 11A-B for an illustration of an exemplary method in accordance with this description. In some embodiments, the target polynucleotide is not circular. For example, the target polynucleotide may comprise a translocation junction (e.g., BCR-ABL, or any other translocation) that brings the binding sites for the capture oligomer and the second oligomer into proximity. In some embodiments, the second oligomer is provided to the reaction mixture at a concentration higher than the capture oligomer. In some embodiments, the second oligomer is provided to the reaction mixture at a concentration lower than the capture oligomer.

The following further embodiments apply to any of the foregoing methods. In some embodiments, the secondary capture reagent comprises a binding partner (e.g., biotin) and isolating comprises contacting the complex with a solid support (e.g., beads) comprising a second binding partner (e.g., streptavidin) configured to bind the binding partner of the secondary capture reagent. The capture oligomer may be provided in excess relative to the secondary capture reagent.

Exemplary concentration and quantity ranges for the capture oligomer and, where applicable, the complementary and/or second oligomers, include $10^7$ to $10^{13}$ molecules/reaction, $10^9$ to $10^{12}$ molecules/reaction, or $10^{10}$ to $10^{12}$ molecules/reaction for the capture oligomer; about $1.5 \times 10^7$ to $10^{14}$ molecules/reaction or about $1.5 \times 10^9$ to $10^{13}$ molecules/reaction for the complementary oligos; and $10^6$ to $10^{14}$ molecules/reaction or $10^8$ to $10^{13}$ molecules/reaction for the second oligomers. Exemplary ranges for the secondary capture reagent are provided above.

The methods are useful for capturing target polynucleotides from any source. In some embodiments, the source of the target polynucleotide is a clinical specimen, a pathogen, or an environmental sample. In some embodiments, the clinical sample is a sample (e.g., blood, serum, or plasma sample) from a subject having or suspected of having sepsis and in some embodiments it is a sample from a patient having or suspected of having cancer. In some embodiments, the target polynucleotide is an extension or amplification product.

In some embodiments, the target polynucleotide is a member of a sequencing library.

In some embodiments, an extension product (extended capture oligomer) is formed by extending the capture oligomer along the target polynucleotide and the capture oligomer comprises a third or fourth additional sequence. In some embodiments, the method further comprises contacting the extension product with a blocker oligomer comprising the third or fourth additional sequence, which is non-extendable, optionally wherein the blocker oligomer is configured to bind the complement of the third or fourth additional sequence with a greater affinity than the third or fourth additional sequence of the capture oligomer or to form a complex with the complement of the third or fourth additional sequence having a higher melting temperature than a complex of the third or fourth additional sequence of the capture oligomer and the complement of the third or fourth additional sequence. This approach is useful to reduce or avoid nonspecific extension, e.g., where the product of a mispriming event by the capture oligomer can give rise to additional rounds of amplification through hybridization of the third or fourth additional sequence to a reverse extension product that would otherwise occur in the absence of the blocker oligomer.

In some embodiments, the method further comprises:
contacting the target polynucleotide with an amplification oligomer, the amplification oligomer comprising (i) a reverse target hybridizing sequence that binds the target polynucleotide in a reverse orientation relative to the capture oligomer and (ii) an additional sequence located 5' of the second target hybridizing sequence. The method further comprises extending the amplification oligomer along the target polynucleotide to form a reverse extension product, wherein a portion of the capture oligomer anneals to the reverse extension product. Such embodiments are useful for incorporating an additional sequence (e.g., tag, such as an adaptor) to the end of the target distal from the end bound to or incorporating the capture oligomer. As discussed elsewhere, extension along the capture oligomer (e.g., an extended capture oligomer) can displace a complement of a capture sequence from a capture sequence. The amplification oligomer can also be used to prime such extension.

In some embodiments, e.g., wherein the capture oligomer comprises a blocking moiety at its 3' end, the method further comprises isolating a complex comprising the reverse extension product (e.g., produced as described above, or using an amplification oligomer that does not necessarily comprise an additional sequence) annealed to the capture oligomer in which the extension product is substantially single-stranded 5' of the target-hybridizing sequence of the capture oligomer and the capture element of the capture oligomer has been displaced by extension of the reverse extension product, e.g., as illustrated in FIG. 5. An extension product is considered substantially single stranded if at least half of the molecule is not hybridized to another strand. Thus, for example, short stretches of self-hybridized nucleic acid do not prevent a molecule or portion thereof from being substantially single stranded.

In some embodiments in which a reverse extension product is produced, the capture oligomer is extendable and the method further comprises extending the capture oligomer along the reverse extension product, thereby forming a second extension product which comprises a complement of the amplification oligomer. The second extension product will comprise any additional sequence present in the capture oligomer and a complement of any additional sequence present in the reverse amplification oligomer. In this way, a product can be generated that comprises additional sequences (e.g., tags, such as one or more adaptors) near or at one or both ends (e.g., both ends).

In some embodiments, the target polynucleotide comprises a sequence from a DNA or RNA of a target organism and an additional sequence, and the target hybridizing sequence of the capture oligomer is configured to anneal to the additional sequence of the target polynucleotide. The additional sequence may have been added in a previous reaction, such as an extension, ligation, or amplification reaction. For example, the additional sequence can be a sequence not present in the DNA or RNA of the target organism. Such an additional sequence may have been added in an earlier extension reaction using a primer comprising the additional sequence. This approach facilitates multiplex capture or reuse of a capture oligomer design with different targets to which the same additional sequence has been attached. In some embodiments, the composition comprises a plurality of target polynucleotides comprising (i) the additional sequence and (ii) different sequences from the DNA or RNA of the target organism, and the method comprises capturing the plurality of target polynucleotides.

In some embodiments, the capture oligomer comprises a reversible extension blocker located 5' of the target-hybridizing sequence and the method comprises: copying or amplifying the target polynucleotide before unblocking the reversible extension blocker; unblocking the reversible extension blocker; and performing a further round or rounds of copying or amplifying the target polynucleotide. In some embodiments, only a single cycle of amplification/extension is performed after unblocking the reversible extension blocker before capturing the target polynucleotide. In some embodiments an amplification oligomer comprises a reversible extension blocker and functions similarly as described above. In some embodiments, an amplification oligomer and a capture oligomer both with reversible extension blockers are used together in the same process. In such cases, the reversible extension blockers of the amplification capture oligomers can be reversed concurrent or in separate steps. In some embodiments, the reversible extension blocker is a member of a non-natural nucleotide pair (e.g., IsoC or IsoG) and unblocking the reversible extension blocker comprises providing the complementary member of the non-natural nucleotide pair.

In some embodiments, the method comprises circularizing an extension product of the target polynucleotide. For example, where the capture oligomer comprises a mixed-nucleotide segment between the extension blocker and the first portion of the spacer sequence or the complement of the capture sequence (e.g., immediately 3' of the internal extension blocker). The method comprises extending the 3' end of the target polynucleotide along the capture oligomer up to the internal extension blocker, thereby forming an extension product comprising a complement of the mixed-nucleotide segment at its 3' end. The method further comprises contacting the extension product with a splint oligonucleotide comprising, in the 5' to 3' direction: a complement of a 5' terminal segment of the extension product; the mixed-nucleotide segment; a complement of the capture sequence; and optionally, a segment complementary to a segment in the extension product immediately 5' of the capture sequence. The method further comprises ligating the 5' end of the extension product to the 3' end of the extension product. In some embodiments, the 5' terminal segment of the extension product comprises at least part of the sequence of an amplification oligomer used to generate the target polynucleotide, e.g., at least part of the target-hybridizing sequence of the amplification oligomer, or (where applicable) at least part of an additional sequence of the amplification oligomer wherein the additional sequence is 5' of the target-hybridizing sequence of the amplification oligomer. See FIG. 12 for an illustration of an exemplary method in accordance with this description.

In some embodiments, any of the foregoing methods comprises adding additional sequences on one or both ends of a target polynucleotide. For example, such a method may comprise contacting the target polynucleotide with a capture oligomer described herein, wherein the target-hybridizing sequence of the capture oligomer anneals at a site upstream of the 3' end of the target polynucleotide;

extending the 3' end of the capture oligomer along the target polynucleotide, thereby forming a first extended strand;

contacting the target polynucleotide with a displacer oligomer comprising a displacer target-hybridizing sequence that anneals to the target polynucleotide downstream of the target-hybridizing sequence of the capture oligomer;

extending the displacer oligomer along the target polynucleotide, thereby displacing the first extended strand, optionally wherein the capture oligomer and the displacer are added to the composition simultaneously or sequentially (e.g., such that extension of the capture oligomer commences before displacement due to extension of the displacer oligomer). The capture oligomer may further comprise an additional sequence (e.g., third or fourth additional sequence) located 5' of the target-hybridizing sequence. In some embodiments, the THS of the capture oligomer has a higher Tm, or greater affinity, for binding to its complement than the displacer oligomer THS does for its complement, or the capture oligomer is provided in a greater concentration than the displacer oligomer. This can facilitate binding by, and extension (or at least commencement of extension) of, the capture oligomer before extension of the displacer oligomer. Where the Tm and/or affinity of the capture oligomer is higher, this can be further facilitated by incubating the reaction mixture first at a higher temperature that allows binding and extension of the capture oligomer preferentially relative to binding and extension of the displacer oligomer, then at a lower temperature that allows binding and extension of the displacer oligomer.

In some embodiments, such a method further comprises contacting the first extended strand of the target polynucleotide with a reverse amplification oligomer comprising a reverse target-hybridizing sequence configured to bind the first extended strand and extending the reverse amplification oligomer, thereby forming a second extended strand. The reverse amplification oligomer may comprise an additional sequence 5' of its target-hybridizing sequence.

In some embodiments, such a method further comprises contacting the first extended strand with a reverse amplification oligomer comprising a reverse target-hybridizing sequence configured to bind to the 3'-end of the first extended strand and extending the reverse amplification oligomer, thereby forming a second extended strand. The reverse amplification oligomer may comprise an additional sequence 5' of its target-hybridizing sequence, in which case the first extended strand is further extended using the additional sequence as a template, creating a complement of the additional sequence. See FIG. 8A.

In some embodiments, the target polynucleotide comprises a sequence from a DNA or RNA of a target organism and an additional sequence not present in the DNA or RNA of the target organism, and the target hybridizing sequence of the capture oligomer is configured to anneal to the additional sequence of the precursor of the target polynucleotide. The displacer oligomer is also configured to anneal to the additional sequence of the precursor of the target polynucleotide, wherein the binding site for the displacer oligomer in the additional sequence is downstream from the binding site of the target-hybridizing sequence of the capture oligomer (e.g., see FIG. 8B).

In some embodiments, the first strand of the target polynucleotide comprises a second adaptor sequence located proximal to a sequence from a DNA or RNA of a target organism and distal to the target-hybridizing sequence of the capture oligomer, and the method further comprises contacting the first strand of the target polynucleotide with a reverse amplification oligomer comprising a reverse target-hybridizing sequence configured to bind the second adaptor sequence and extending the reverse amplification oligomer, thereby forming a second strand of the target polynucleotide.

In some embodiments, any of the foregoing methods further comprise performing clonal amplification of the captured target polynucleotide. In some embodiments, such a method further comprises sequencing the clonally amplified target polynucleotide. In some embodiments, any of the foregoing methods further comprise performing sequencing of the captured target polynucleotide. In some embodiments, the sequencing is Sanger sequencing or next-generation sequencing, optionally wherein the next-generation sequencing comprises sequencing by synthesis, sequencing by ligation, sequencing by hybridization or single-molecule sequencing. Next-generation sequencing includes any form of sequencing that generates reads in a significantly parallel manner compared to Sanger sequencing.

4. Capture Oligomers and Combinations for Limited Capture and Other Applications a. Capture Oligomers Comprising Self-Complementary Sequences In some embodiments, a capture oligomer is provided that comprises a first self-complementary sequence, a target-hybridizing sequence, and a second self-complementary sequence, wherein the first and second self-complementary sequences are configured to anneal to each other when the target-hybridizing sequence is single stranded and not when the target-hybridizing sequence is annealed to its target. Such a capture oligomer may be combined with a secondary capture reagent that comprises a complement of the first or second self-complementary sequence and a binding partner. The capture oligomer may be present in the combination in a greater amount than the secondary capture reagent. Such oligomers and combinations are useful for capturing a certain amount (e.g., a limited amount or an amount less than or equal to a predetermined amount) of a target polynucleotide from a composition.

In some embodiments, such a capture oligomer has the formula:

5'-SC1-THS2-THS1-L-THS2'-SC2-3'.

In some embodiments, such a capture oligomer has the formula:

5'-SC2-THS2'-L-THS1-THS2-SC1-3'.

In each of the foregoing formulae, SC1 is the first self-complementary sequence; THS2 and THS1 are second and first portions of the target-hybridizing sequence, respectively; L is an optionally present linker; THS2' is an optionally present complement of the second portion of the target-hybridizing sequence; and SC2 is the second self-complementary sequence.

Either of the first and second self-complementary sequences may function as a capture sequence. Where the first self-complementary sequence is a capture sequence, the second self-complementary sequence is a complement of the capture sequence. Where the second self-complementary sequence is a capture sequence, the first self-complementary sequence is a complement of the capture sequence. Capture sequences and complements of capture sequences are discussed in detail elsewhere herein. Any suitable capture sequence and complement thereof may be used.

Where present, the linker may be any suitable linker, e.g., any linker described elsewhere herein including sequence and non-sequence linkers. The linker can serve as a flexible element that facilitates intramolecular hybridization of the first and second self-complementary sequences. Where the linker comprises a sequence, the sequence in some embodiments is a sequence not present in a source (e.g., organism, genome, gene, or other nucleic acid or combination thereof) from which the target-hybridizing sequence originated or to which the target-hybridizing sequence is complementary. The linker should generally be not so long that it permits intramolecular hybridization of the first and second self-complementary sequences even when the target-hybridizing sequence is annealed to its target, however (see discussion below).

Target-hybridizing sequences are discussed in detail elsewhere herein. Any suitable target-hybridizing sequence (and, where present, complement of a portion thereof) may be used.

Secondary capture reagents are discussed in detail elsewhere herein and comprise a complement of the capture sequence. Any suitable secondary capture reagent may be used.

Where the capture oligomer is present in the combination in a greater amount than the secondary capture reagent, the ratio may be about 10,000 to 1, 5000 to 1, 2000 to 1, 1000 to 1, 500 to 1, 200 to 1, 100 to 1, 50 to 1, 20 to 1, 10 to 1, 5 to 1 or 2 to 1.

Such capture oligomers are useful in methods to capture a target polynucleotide. The capture oligomer can adopt a self-hybridized conformation in the absence of a target polynucleotide. The self-hybridized conformation involves annealing of the first and second self-complementary sequences to each other and thus renders the capture oligomer substantially unable to interact with the complement of the capture sequence of the secondary capture reagent. The target-hybridizing sequence is at least partially single-stranded, however. When a target polynucleotide is present, the target-hybridizing sequence can hybridize to it. When the target-hybridizing sequence is thus substantially double stranded, intramolecular hybridization of the first and second self-complementary sequences should not occur because, among other potential factors, they are too far apart. Thus, the capture sequence (i.e., one of the first and second self-complementary sequences) is substantially single-stranded and can hybridize to the secondary capture reagent. It can be beneficial for the hybridization of the target-hybridizing sequence to be more energetically favorable than the intramolecular hybridization of the first and second self-complementary sequences, so that the capture oligomer will preferentially hybridize to available target polynucleotide. An excess of capture oligomer can also be used to drive formation of the complex with the target polynucleotide.

A complex of the secondary capture reagent, the capture oligomer, and the target can then be isolated, e.g., using standard techniques appropriate for the binding partner or solid support of the secondary capture reagent. The amount of polynucleotide captured can be limited or determined by the amount of secondary capture reagent or by the amount of capture oligomer in combination with the amount of secondary capture reagent.

b. Combinations Comprising a Capture Oligomer and a Complementary Oligomer Having a Complement of a Portion of the Capture Sequence In some embodiments, a combination is provided, comprising a capture oligomer and a complementary oligomer, wherein:

(a) the capture oligomer comprises, in the 5' to 3' direction:

a capture sequence comprising first and second portions, and a target-hybridizing sequence comprising second and first portions; and (b) the complementary oligomer comprises, in the 3' to 5' direction:

a complement of the second portion of the capture sequence, and a complement of the second portion of the target-hybridizing sequence, wherein the complement of the second portion of the capture sequence and the complement of the second portion of the target-hybridizing sequence are configured to anneal simultaneously to the capture oligomer in the absence of a complement of the target-hybridizing sequence. FIG. 10B provides an illustration of exemplary oligomers in accordance with these embodiments. Optional additional elements may be present as described in the further embodiments listed above and/or as illustrated in FIG. 10B (e.g., any individual element in FIG. 10B or any combination thereof).

The combination can be used to perform limited capture in that the complementary oligomer can be configured to bind free capture oligomer but not capture oligomer bound to a target polynucleotide. For example, binding of the target-hybridizing sequence of the capture oligomer to the target polynucleotide can be more energetically favorable than binding of the complement of the second portion of the capture sequence to the second portion of the target-hybridizing sequence. In the absence of target polynucleotide, the complementary oligomer binds to the capture oligomer and blocks accessibility to the capture sequence (C1+C2 in FIG. 10B) to a sufficient extent to block binding of the capture sequence by a complement of the capture sequence in a secondary capture reagent, which can be any of the secondary capture reagents described elsewhere herein.

Accordingly, also provided is a method of capturing a target polynucleotide from a composition, the method comprising:

contacting the composition with the combination described above or any further embodiment thereof described herein, wherein the target-hybridizing sequence of the capture oligomer anneals to the target polynucleotide;

contacting the capture oligomer with the complementary oligomer before or after the capture oligomer anneals to the target polynucleotide, wherein the complementary oligomer anneals to free capture oligomer and partially occupies its capture sequence, wherein the complementary oligomer does not anneal to a complex comprising the capture oligomer annealed to the target polynucleotide and wherein if contacting the capture oligomer with the complementary oligomer occurs before the capture oligomer anneals to the target polynucleotide, then the annealing of the target-hybridizing sequence to the target polynucleotide results in dissociation of the complementary oligomer from the capture oligomer;

contacting the capture sequence of capture oligomer complexed with the target polynucleotide with a secondary capture reagent comprising a complement of the capture sequence and (i) a binding partner or (ii) a solid support, thereby forming a complex comprising the target polynucleotide, the capture oligomer, and the secondary capture reagent; and isolating the complex from the composition, thereby capturing the target polynucleotide. Optional additional elements may be present as described in the further embodiments listed above and/or as illustrated in FIG. 10B (e.g., any individual element in FIG. 10B or any combination thereof).

5. Differential Capture Methods and Oligomer Combinations

Also provided herein are methods and oligomer combinations for capturing capture oligomers differentially (e.g., with different affinities) based on whether or not they are in a complex with a target polynucleotide. Such methods permit elution of the target polynucleotide without substantially eluting capture oligomer not associated with the target polynucleotide. Capture sequences, target-hybridizing sequences, and other elements of oligomers in such combinations and methods may be, e.g., any of the capture sequences, target-hybridizing sequences, etc. described herein that are consistent with the features of the oligomers, combinations, and methods set forth below.

In some embodiments, such a method comprises contacting the target polynucleotide with a capture oligomer comprising, in the 5' to 3' direction: a capture sequence; an optional internal extension blocker; an optional spacer sequence; and a target hybridizing sequence that is configured to anneal to the target polynucleotide. Such contacting may thereby anneal at least some of the capture oligomer (i.e., a fraction of the population of capture oligomer) to the target polynucleotide. The method further comprises contacting the capture oligomer with a first capture reagent comprising a complement of the capture sequence (before, while, or after contacting the target polynucleotide with the capture oligomer); and providing a second capture reagent comprising a complement of a sequence in the capture oligomer other than the capture sequence, wherein if some or all of the capture oligomer is not annealed to the target polynucleotide, the second capture reagent contacts the capture oligomer that is not annealed to the target polynucleotide. The sequence in the capture oligomer other than the capture sequence may be some or all of the target-hybridizing sequence or a sequence that overlaps with the target-hybridizing sequence, or a sequence that otherwise is rendered inaccessible to the second capture reagent when the capture oligomer is annealed to the target polynucleotide. The method further comprises isolating first and second complexes from the composition, wherein the first complex comprises the target polynucleotide and the second complex comprises capture oligomer not annealed to the target polynucleotide; and selectively eluting the target polynucleotide or a subcomplex comprising the target polynucleotide from the first complex.

In some embodiments, the target polynucleotide is contacted with an excess amount of the capture oligomer. In some embodiments, the first capture reagent is provided in a limiting amount relative to the capture oligomer. In some embodiments, the capture oligomer is provided in a limiting amount relative to the target polynucleotide. In some embodiments, the fraction of the capture oligomer contacted with the second capture reagent comprises unbound capture oligomer.

In some embodiments, the first capture reagent comprises a first solid support that comprises a complement of the capture sequence. Additional aspects of such embodiments are set forth elsewhere herein, including in the summary above.

In some embodiments, the first capture reagent further comprises a second capture sequence which is not complementary to the capture oligomer or the target polynucleotide, and the method comprises, after contacting the annealed capture oligomer with the first capture reagent, annealing the second capture sequence to a solid support comprising a complement of the second capture sequence. Additional aspects of such embodiments are set forth elsewhere herein, including in the summary above.

Also provided herein is a combination comprising a capture oligomer, a first solid support, and a second solid support. The capture oligomer comprises, in the 5' to 3' direction:

a first capture sequence, an internal extension blocker, a second capture sequence, and a target hybridizing sequence.

The first solid support comprises a complement of the first capture sequence. The second solid support comprises a complement of the second capture sequence. A first complex formed by annealing of the first capture sequence and the complement of the first capture sequence has a lower melting temperature than a second complex formed by annealing of the second capture sequence and the complement of the second capture sequence, and/or the complement of the second capture sequence has an affinity for the second capture sequence which is greater than the affinity of the complement of the first capture sequence for the first capture sequence.

Also provided herein is a combination comprising a capture oligomer, a first capture reagent, a second capture reagent, a first solid support, and a second solid support.

The capture oligomer comprises, in the 5' to 3' direction:

a first capture sequence, an internal extension blocker, and a target hybridizing sequence.

The first capture reagent comprises a second capture sequence and a complement of the first capture sequence, wherein the second capture sequence is not complementary to the capture oligomer. The second capture reagent comprises a third capture sequence and a complement of a sequence of the capture oligomer other than the first capture sequence, wherein the third capture sequence is not complementary to the capture oligomer. The first solid support comprises a complement of the second capture sequence. The second solid support comprises a complement of the third capture sequence. A first complex formed by annealing of the second capture sequence and the complement of the second capture sequence has a lower melting temperature than a second complex formed by annealing of the third capture sequence and the complement of the third capture sequence, and/or the complement of the third capture sequence has an affinity for the third capture sequence which is greater than the affinity of the complement of the second capture sequence for the second capture sequence.

Also provided herein is a combination comprising a capture oligomer and a secondary capture reagent. The capture oligomer comprises a target-hybridizing sequence comprising one or more affinity-enhancing nucleotides and a capture sequence. The secondary capture reagent comprises a complement of the capture sequence and a binding partner. In some embodiments, the capture sequence is located 5' to the target-hybridizing sequence. In some embodiments, the target-hybridizing sequence is configured to anneal to an adaptor sequence. In some embodiments, the secondary capture reagent is present in the combination in a lower amount than the capture oligomer.

Also provided herein is a method of capturing a target polynucleotide from a composition, the method comprising contacting the target polynucleotide with such a combination as described above. The capture oligomer and the secondary capture reagent are added simultaneously or sequentially. The target-hybridizing sequence of the capture oligomer anneals to the target polynucleotide and the secondary capture reagent anneals to the capture sequence of the capture oligomer, thereby forming a complex.

The method further comprises contacting the complex with a second binding partner configured to bind the binding partner of the secondary capture reagent, wherein the second binding partner is associated with a solid support, and the second binding partner binds the binding partner of the secondary capture reagent; and isolating the complex from the composition, thereby capturing the target polynucleotide.

In some embodiments, the secondary capture reagent is present in the combination in a lower amount than the capture oligomer and/or the target polynucleotide. In some embodiments, the capture oligomer is present in the combination in a lower amount than the target polynucleotide and the secondary capture reagent is present in the combination in a lower amount than the capture oligomer. In some embodiments, the target polynucleotide comprises an adaptor sequence and the target-hybridizing sequence anneals to the adaptor sequence. In some embodiments, the target polynucleotide comprises a sequence from a DNA or RNA of a target organism, and the adaptor sequence is not present in the DNA or RNA of the target organism.

IV. EXAMPLES

The following examples are provided to illustrate certain disclosed embodiments and are not to be construed as limiting the scope of this disclosure in any way.

A. Capture of Predetermined Amount of Amplicon with a Capture Oligomer Comprising a Capture Sequence and a Complement Thereof Oligomers.

PCR to amplify a segment from the *E. coli* uidA gene was carried out using the primers:

```
Ec_uidA_F:
                                  (SEQ ID NO: 1)
GTATCAGCGCGAAGTCTTTATACC Ec_uidA_R:
                                  (SEQ ID NO: 2)
GGCAATAACATACGGAGTGACATC
```

The primers were designed to generate an amplicon with the following sequence:

```
                                  (SEQ ID NO: 3)
GTATCAGCGCGAAGTCTTTATACCGAAAGGTTGGGCGGGCCAG

CGTATTGTACTGCGTTTCGATGCGGTCACTCATTACGGCAAAG

TGTGGGTAAATAATCAGGAAGTGATGGAGCATCAGGGCGGCTA

TACGCCATTTGAAGCCGATGTCACTCCGTATGTTATTGCC
```

A capture oligomer designated uidA_PA_1.2 was provided having the following sequence:

```
                                  (SEQ ID NO: 4)
AAAAAAAAAAAAAAAAAAAAAAAAAAAAAAAAAAAAACCTCTA/ iSp18/TTTTTTTTTTTTTTTTTTTTTTTTTTTTTTTTTTT

AGACGCAAGCTACTGGTGATTTGGCAATAACATACGGAGTG

ACATCGGCTTC
(iSp18 = Hexaethylene Glycol (HEG)
internal spacer (IDT))
```

In this oligomer, the 5' poly-A sequence is the capture sequence. CCTCTA is a linker sequence. iSp18 is the internal extension blocker. The poly-T sequence following iSp18 is the complement of the capture sequence. AGACGCAAGCTACTGGTGATTT (SEQ ID NO: 5) is a fourth additional sequence. The target-hybridizing sequence (THS) is GGCAATAACATACGGAGTGACATCGGCTTC (SEQ ID NO: 6), which hybridizes specifically to a segment of the uidA gene sequence in the target amplicon. In this example the THS is longer than the reverse PCR primer (see sequence above), with which it overlaps, to raise the Tm of the THS and give it a competitive advantage over the reverse primer in hybridizing to the target.

A secondary capture reagent with the following sequence was used:

```
dT30-biotin:
                                  (SEQ ID NO: 7)
TTTTTTTTTTTTTTTTTTTTTTTT/3'Biotin
```

The following primers and probe were used for quantitative PCR (qPCR) analysis of copy control products:

```
Ec_uidA_F
                                  (SEQ ID NO: 1)
GTATCAGCGCGAAGTCTTTATACC uidA_Probe
                                  (SEQ ID NO: 8)
5'FAM/TAGCCGCCCTGATGCTCCATCACTTCCTG/3'IowaBlack

TQ_R
                                  (SEQ ID NO: 9)
AGACGCAAGCTACTGGTGAT
```

Protocol/Reaction Conditions.

(1) PCR amplicon was generated for the target uidA utilising the primers shown above; amplicon was purified using AMPure XP (Beckman Coulter) using the manufacturer's recommended protocols and quantitated via qPCR using the uidA forward and reverse primers along with the uidA_Probe.

(2) Capture oligomer annealing and extension of the amplicon strand—The purified uidA amplicon was diluted 2-, 10- or 100-fold. A 20 µL aliquot of each dilution of the amplicon was added to capture oligomer annealing/extension reactions consisting of 0.07 U/µl SDPol (Bioron), 1×SDPol reaction buffer, 0.17 mM dNTP's, 3 mM $MgCl_2$, 1 mg/ml BSA and $5 \times 10^{10}$ copies of the capture oligomer for a final volume of 30 µL. The capture oligomer was annealed to the 3'-end of the complementary strand of the uidA amplicon and the amplicon strand was extended using a thermal cycler according to the following thermal profile: 92° C. for 2 minutes, 54° C. for 2 minutes, 68° C. for 10 minutes, 54° C. for 2 minutes followed by a controlled ramp down (0.3° C./second) to 20° C. In this example the 3'-end of the capture oligomer was also extended.

(3) Hybridization of the complement of the capture sequence of the capture oligomer—The entire capture oligomer/amplicon extension reaction mixture was added to 10 µL of a secondary capture reagent at 4× concentration, resulting in a final concentration of 125 mM NaCl, 0.25 mg/ml BSA and $10^7$, $10^8$ or $10^9$ copies of the complement of the capture sequence (i.e., 3 different amounts were tested). Hybridization was carried out by incubating the reaction mix at room temperature (20-24° C.) for 15 minutes.

(4) Capture of the amplicon and capture oligomer extension product/capture oligomer complex—A 5 µL aliquot (50 µg) of MyOneC1 streptavidin beads (ThermoFisher Scientific) in 250 mM NaCl and 1 mg/ml BSA was added to the hybridisation mixture (step 3 above), the capture oligomer/amplicon extension product/complement of the capture sequence complex was captured onto the beads and the beads were washed as per manufacturer's recommendations.

(5) Elution—After the final wash was completed and the wash buffer removed, 10 µL of water was added to the bead pellet, the beads were resuspended and incubated at 70° C. for 2 minutes. The beads were pelleted with a magnet and the eluate was removed.

(6) Quantitation—The amount of eluted product as well as capture oligomer extension products (see step 2 above) were quantified by qPCR using primers targeting the uidA_F primer site and the TQ primer-adaptor site along with the uidA_Probe.

Results and Conclusions:

A 2-fold, 10-fold and 100-fold dilution of the amplicon produced in the targeted enrichment step (see step 1 above) were subjected to the copy control process (see steps 2-5 above) using $10^7$, $10^8$ or $10^9$ copies of capture oligomer. As shown in Table 1, the amount of recovered amplicon was proportional (in approximately the expected ratios; see "Ratio" column in the table) to the amount of capture oligomer added for each PCR dilution. Variation between replicates at each data point was low (see "Std Dev" column).

TABLE 1

| PCR dilution | 2nd CO (# copies) | Output (# copies*) | Std Dev | Ratio** |
|---|---|---|---|---|
| 2-fold | $1 \times 10^7$ | $9.8 \times 10^8$ | $6.1 \times 10^7$ | 1 |
| | $1 \times 10^8$ | $4.4 \times 10^9$ | $2.5 \times 10^9$ | 4.5 |
| | $1 \times 10^9$ | $8.0 \times 10^{10}$ | $4.5 \times 10^9$ | 82 |
| 10-fold | $1 \times 10^7$ | $7.7 \times 10^8$ | $8.7 \times 10^7$ | 1 |
| | $1 \times 10^8$ | $5.7 \times 10^9$ | $1.2 \times 10^8$ | 7.4 |
| | $1 \times 10^9$ | $6.5 \times 10^{10}$ | $2.0 \times 10^9$ | 84 |
| 100-fold | $1 \times 10^7$ | $4.4 \times 10^8$ | $8.3 \times 10^7$ | 1 |
| | $1 \times 10^8$ | $2.6 \times 10^9$ | $2.0 \times 10^8$ | 5.9 |
| | $1 \times 10^9$ | $2.8 \times 10^{10}$ | $2.7 \times 10^9$ | 64 |

*Average of 3 replicates
**Set the value at 2-fold dilution equal to 1

Furthermore, despite a 50-fold difference in the amplicon input amount, variation in output was 2.36-fold, 3.11-fold and 3.44-fold for $10^7$, $10^8$ and $10^9$ copies of capture oligomer, respectively (Table 1). As above, variations between replicates were low.

These data demonstrate that a capture oligomer described herein can be used to yield a pre-determined amount of target output from a range of different input target amounts.

An additional experiment was performed essentially as described above but in a multiplex format using capture oligomers in which the THS regions were designed to target the uidA gene of *E. coli*, the nuc gene of *Staphylococcus aureus*, the vanA gene of *Enterococcus faecalis* or the rpb7 gene of *Candida albicans*. (i.e., 4 capture oligomers were used per reaction). The uidA, nuc and vanA genes were each amplified separately using PCR as described above using and the primers shown above for uidA and additional primers designed for the nuc and vanA genes. Resulting amplicons were diluted 10- or 100-fold and a 20 µL aliquot of each dilution of each individual target was added to a separate capture oligomer annealing and extension of amplicon strand reaction containing $5 \times 10^{10}$ copies each of the 4 capture oligomers described above (i.e., 4-plex capture oligos but only 1 target present). The reaction conditions were the same as those described about except with the following thermal profile: 92° C. for 2 minutes, 64° C. for 2 minutes, 68° C. for 10 minutes, 98° C. for 2 minutes, 57° C. for 2 minutes followed by a controlled ramp down (0.3° C./second) to 20° C. After this reaction was completed, $5 \times 10^8$ copies of the complement of the capture sequence of the capture oligomers was added to each reaction. This was followed by capture, wash, elution and quantitation steps as described above.

Output amounts following capture of amplicon with input amounts differing by a factor of 10 are shown in Table 2. The results show that a 10-fold difference in input amplicon level was reduced to no more than a 1.4-fold difference in average output level after copy control for each of the 3 individual target amplicons tested in a multiplex format. Furthermore, the range of average output level after copy control spanned approximately 1.6-fold across all 3 target amplicons whereas their input level spanned more than 270-fold.

TABLE 2

| Target | Input | Output* | Std Dev |
|---|---|---|---|
| nuc | $1.6 \times 10^8$ | $1.5 \times 10^7$ | $9.0 \times 10^5$ |
| | $1.6 \times 10^9$ | $1.7 \times 10^7$ | $2.0 \times 10^6$ |
| uidA | $3.3 \times 10^9$ | $1.9 \times 10^7$ | $2.3 \times 10^5$ |
| | $3.3 \times 10^{10}$ | $1.9 \times 10^7$ | $3.4 \times 10^6$ |
| vanA | $1.2 \times 10^8$ | $1.2 \times 10^7$ | $1.3 \times 10^6$ |
| | $1.2 \times 10^9$ | $1.6 \times 10^7$ | $1.3 \times 10^6$ |

*Average of 3 replicates

An additional experiment was performed essentially as described above in a singleplex format but using a capture oligomer in which the THS anneals to a universal binding site in a tag sequence incorporated into the target of interest during the PCR amplification step. Primers were designed to target the bacterial 23S rRNA gene and PCR amplicon was generated from bacterial genomic DNA. The reverse primer comprised a universal sequence tag that was incorporated into the amplicon during PCR. Capture oligomer annealing and extension of an amplicon strand was performed as described above except that a 40 μL aliquot of neat (i.e., no dilution; approximately $9×10^{12}$ copies) or a 50-fold dilution (approximately $2×10^{11}$ copies) were added to the reaction mixture comprised 0.02 U/μL SD Polymerase (Bioron), 0.4×SD Polymerase reaction buffer (Bioron), 0.012 mM of the 4 dNTP's, 1.8 mM $MgCl_2$, 0.6 mg/mL BSA and $5×10^{10}$ copies of capture oligomer in a final reaction volume of 100 μL. The thermal profile used was 92° C. for 2 minutes, 54° C. for 2 minutes, 68° C. for 10 minutes, 54° C. for 2 minutes followed by a controlled ramp down (0.3° C./second) to 20° C. The entire volume of the above reaction was added to 50 μL of a 3× annealing mix containing 1 mg/ml BSA, 125 mM NaCl, and $5×10^8$ copies of the secondary capture reagent. Annealing is carried out by incubating the reaction mix on a thermal block at 25° C. for 10 minutes. A 50 μL volume (200 μg in this experiment) of MyOneC1 streptavidin beads (ThermoFisher Scientific) in a 4× Wash Buffer consisting of 4M NaCl, 20 mM Tris-HCl pH 7.5, 2 mM EDTA, 0.20% Tween20, 2 mg/mL BSA was added to the 150 μL reaction from above. The resulting complex including the capture oligomer, amplicon extension product, and complement of the capture sequence was captured onto the beads and the beads were washed as per manufacturer's recommendations (using in this case a 1× Wash Buffer; see 4× formulation immediately above). A volume of 20 μL of water was used for elution (protocol otherwise the same as above). qPCR was performed using a specific forward primer and a reverse primer targeted to the universal tag.

Despite a 50-fold difference in amplicon input level, variation in output was only 2.5-fold after the capture oligomer annealing and extension of the amplicon strand step and 1 (i.e., completely normalized) after contacting with the secondary capture reagent and isolation of the resulting complex (see Table 3). Further, these results demonstrate an embodiment of the disclosure in which the THS binds to a universal tag sequence.

TABLE 3

| Step in process | PCR dilution | Output (# copies*) | # of reps | Std Dev | Ratio** |
|---|---|---|---|---|---|
| After first capture oligomer | 0-fold (neat) | $2.1 × 10^{10}$ | 4 | $4.5 × 10^8$ | 2.5 |
| | 50-fold | $8.3 × 10^9$ | 4 | $1.8 × 10^8$ | |
| After second capture oligomer | 0-fold (neat) | $1.7 × 10^7$ | 6 | $3.6 × 10^5$ | 1 |
| | 50-fold | $1.6 × 10^7$ | 9 | $3.5 × 10^5$ | |

*Average of replicates (reps)
**Neat/50-fold dilution output

An additional experiment was performed essentially as described immediately above (singleplex, universal THS) but in a multiplex format using a capture oligomer in which the THS anneals to a universal tag sequence incorporated into each of the targets of interest during the PCR amplification step. Eight different amplicons targeting regions in the bacterial 16S rRNA gene, 23S rRNA gene and the antibiotic resistance marker KPC were generated from *K.*

*pneumonia* genomic DNA in eight separate singleplex reactions. One amplicon targeting a synthetic Internal Control (IC) DNA was also generated for a total of nine individual amplicons. Equal amounts of all 9 amplicons were pooled and a 54 μL aliquot of neat (i.e., no dilution; approximately $1×10^{13}$ copies) or a 10-fold dilution (approximately $1×10^{12}$ copies) were added to separate capture oligomer annealing and extension of an amplicon strand reaction mixtures (100 μL final volume for each). The remainder of the workflow was performed essentially the same as described above, except that $5×10^{11}$ copies of capture oligomer and $5×10^9$ of the secondary capture reagent were used. qPCR was performed to quantitate each target using a specific forward primer and a reverse primer targeted to the universal tag (9 separate PCRs). The quantities recovered for each individual target were summed to determine the overall recovery of the capture process.

Despite a 10-fold difference in amplicon input level, variation in overall output was only 2.5 after the capture oligomer annealing and extension of the amplicon strand step and 1.6 after contacting with the secondary capture reagent and isolation of the resulting complex (see Table). Further, these results demonstrate the embodiment of the invention in which the THS binds to a universal tag sequence in a multiplex format, thus capturing all target amplicons present in the mixture.

TABLE 4

| Step in process | PCR dilution | Output (# copies*) | # of reps | Std Dev | Ratio** |
|---|---|---|---|---|---|
| After first capture oligomer | 0-fold (neat) | $2.6 × 10^{11}$ | 32 | $1.9 × 10^{10}$ | 2.5 |
| | 10-fold | $1.1 × 10^{11}$ | 31 | $7.7 × 10^9$ | |
| After second capture oligomer | 0-fold (neat) | $1.5 × 10^9$ | 89 | $1.1 × 10^8$ | 1.6 |
| | 10-fold | $9.5 × 10^8$ | 88 | $6.9 × 10^7$ | |

*Average of replicates (reps)
**Neat/50-fold dilution output

B. Capture of Predetermined Amount of Amplicon with a Capture Oligomer Comprising a Capture Sequence, a Complement Thereof, and Clamp Sequences A target amplicon was prepared essentially as described above with respect to uidA and used in experiments with a capture oligomer with or without clamp sequences (GCGCGC) inserted as the first and third additional sequences (see FIG. 3). Capture was performed essentially as described above using undiluted, 10× diluted, and 100× diluted amplicon. The amount of product captured was quantified essentially as described above. Results are shown in FIG. 14. Using a capture oligomer containing clamp sequences improved its ability to normalize output amounts across the different dilutions of amplicon.

C. Capture of Predetermined Amount of Amplicon with a Capture Oligomer and a Complementary Oligomer Oligomers.

PCR to amplify a segment from the *E. faecium* vanA gene was carried out using the primers:

```
Efm_vanA_F:
                          (SEQ ID NO: 10)
GGCTGCGATATTCAAAGCTCAG Efm_vanA_R:
                          (SEQ ID NO: 11)
CTGAACGCGCCGGCTTAAC
```

The primers were designed to generate an amplicon with the following sequence:

```
                                        (SEQ ID NO: 12)
GGCTGCGATATTCAAAGCTCAGCAATTTGTATGGACAAATCG

TTGACATACATCGTTGCGAAAAATGCTGGGATAGCTACTCCC

GCCTTTTGGGTTATTAATAAAGATGATAGGCCGGTGGCAGCT

ACGTTTACCTATCCTGTTTTTGTTAAGCCGGCGCGTTCAG
```

A capture oligomer designated CC_Blo_vanA_001 was provided having the following sequence:

```
                                        (SEQ ID NO: 13)
AAAAAAAAAAAAAAAAAAAA/iSp18/CTC

CTCTGGCACCGTGCTGCCTTGGCTTCAT

TGTGGTCCTGAACGCGCCGGCTTAAC
(iSp18 = Hexaethylene Glycol
(HEG) internal spacer (IDT))
```

This oligomer comprises the elements shown for the exemplary capture oligomer of FIG. 10A. In this oligomer, the 5' poly-A sequence is the capture sequence having first and second portions. iSp18 is the internal extension blocker. CTCCTCTGGCACCGTGCTGCCIIGGCTTCAT-TGTGGTC (SEQ ID NO: 14) is a spacer sequence having first and second portions. The target-hybridizing sequence (THS) is CTGAACGCGCCGGCTTAAC (SEQ ID NO: 15), which hybridizes specifically to a segment of the vanA gene sequence in the target amplicon.

A complementary oligo designated Blocker_vanA_001, comprising the elements shown for the exemplary complementary oligomer of FIG. 10A, was provided having the following sequence: CGGTGCCAGAG-GAGTTTTTTTTTT/invdt/(SEQ ID NO: 16) wherein invdt is an inverted T nucleotide which serves as a blocking moiety. In this oligomer, CGGTGCCAGAGGAG (SEQ ID NO: 17) is the complement of the first portion of the spacer sequence of the capture oligomer, and TTTTTTTTTT (SEQ ID NO: 18) is the complement of the second portion of the capture sequence.

A secondary capture reagent with the following sequence was used:

```
dT20-biotin:
                                        (SEQ ID NO: 19)
TTTTTTTTTTTTTTTTTTTT/3'Biotin
```

The following primers and probe were used for quantitative PCR (qPCR) analysis of copy control products:

```
vanA_PCR2_Fwd
                                        (SEQ ID NO: 20)
TTGTATGGACAAATCGTTGACATACA Efm_Probe_FAM
                                        (SEQ ID NO: 21)
5'FAM/TGCTGGGATAGCTACTCCCG CCTTTTGG/3'IowaBlack CC_Univ_Inner_Rev
                                        (SEQ ID NO: 22)
ACCGTGCTGCCTTGGCTTC
```

Protocol/Reaction Conditions.

(1) PCR amplicon was generated for the target vanA utilising the Efm_vanA_F and Efm_vanA_R primers shown above; amplicon was quantitated via chip-based capillary electrophoresis using the Agilent BioAnalyzer.

(2) Capture oligomer annealing and extension of the amplicon strand—The vanA amplicon was used undiluted (neat) or 10-fold diluted (approximately $2 \times 10^{13}$ and $2 \times 10^{12}$ copies, respectively). An 80 μL aliquot of each amplicon amount (neat and 10-fold diluted) was combined with 20 μL of capture oligomer annealing/extension reaction mixture yielding a final mixture consisting of 0.02 U/μl Deep Vent (exo-) Pol (NEB), 0.4× Deep Vent Pol reaction buffer, 0.012 mM dNTP's, 1.8 mM $MgCl_2$, 0.6 mg/ml BSA, $1 \times 10^{11}$ copies of the capture oligomer (CC_Blo_vanA_001) and $1 \times 10^{12}$ copies of the complementary oligomer (Blocker_vanA_001) for a final volume of 100 μL. The capture oligomer was annealed to the 3'-end of the complementary strand of the vanA amplicon and the amplicon strand was extended using a thermal cycler according to the following thermal profile: 92° C. for 2 minutes, 64° C. for 2 minutes and 68° C. for 10 minutes. In this example the 3'-end of the capture oligomer was also extended.

(3) Hybridization of the complement of the capture sequence of the capture oligomer—To the entire capture oligomer/amplicon extension reaction mixture was added 50 μL of a secondary capture reagent at 3× concentration, resulting in a final concentration of 42 mM NaCl, 0.33 mg/ml BSA and $10^9$ copies of the complement of the capture sequence ($dT_{20}$-biotin). Hybridization was carried out by incubating the reaction mix at 30° C. for 10 minutes.

(4) Capture of the amplicon and capture oligomer extension product/capture oligomer complex—A 50 μL aliquot (200 μg) of streptavidin-coated magnetic beads was added to the entire hybridization mixture (150 μL), resulting in a final concentration of 1 M NaCl, 5 mM TrisHCl (pH 7.5), 0.5 mM EDTA, 0.05% Tween 20 and 0.5 mg/ml BSA. The complex was captured onto the beads at 25° C. and the beads were washed using a wash reagent with the same composition as detailed immediately above.

(5) Elution—After the final wash was completed and the wash buffer removed, 30 μL of water was added to the bead pellet, the beads were resuspended and incubated at 70° C. for 2 minutes. The beads were pelleted with a magnet and the eluate was removed.

(6) Quantitation—The amount of eluted product as well as capture oligomer extension products (see step 2 above) were quantified by qPCR using primers targeting the vanA_PCR2_Fwd primer site and the universal primer-adaptor site (CC_Univ_Inner_Rev) along with the Efm_Probe_FAM.

Results and Conclusions:

A 0-fold (neat) and 10-fold dilution of the amplicon produced in step 1 above (PCR) were subjected to the copy control process (see steps 2-5 above) using $10^9$ copies of the secondary capture oligomer. As shown in Table 5, despite a 10-fold difference in the input target amount the output levels were essentially identical.

TABLE 5

| PCR Dilution | Output (# copies) | Fold Difference |
|---|---|---|
| Neat | 3.24E+08 | — |
| 10-fold | 3.14E+08 | 1.03 |

These data demonstrate that a capture oligomer and a complementary oligomer as described herein can be used to yield a pre-determined, normalized amount of target output across a 10-fold difference in input target amounts.

An additional experiment was performed essentially as described above with the following differences:

(1) PCR amplicon was purified using the QIAGEN QIAquick PCR Purification kit according to the manufacturer's instructions prior to quantitation via chip-based capillary electrophoresis using the Agilent BioAnalyzer.

(2) Capture oligomer annealing and extension of the amplicon strand—The vanA amplicon was used undiluted (neat), 10-fold diluted and 100-fold diluted (approximately $8 \times 10^{11}$, $8 \times 10^{10}$ and $6 \times 10^9$ copies, respectively). Capture oligomer (CC_Blo_vanA_001) was used at $1 \times 10^{12}$ copies/reaction of the capture oligomer and the complementary oligo (Blocker_vanA_001) was used at zero or $1 \times 10^{13}$ copies/reaction. The capture oligomer was annealed to the 3'-end of the complementary strand of the vanA amplicon and the amplicon strand was extended using a thermal cycler according to the following thermal profile: 95° C. for 2 minutes and 64° C. for 15 minutes. All other conditions in this step were the same as step 2 above.

(3-6) Steps 3-6 were conducted as described in steps 3-6 above except that in step 4 the complex was captured onto the beads at 30° C. instead of 25° C.

Results and Conclusions:

A 0-fold (neat), 10-fold and 100-fold dilution of the amplicon produced in step 1 above (PCR) were subjected to the copy control process (see steps 2-5 above). In this experiment, the amounts of various nucleic acid components used were approximately $8 \times 10^{11}$, $8 \times 10^{10}$ and $6 \times 10^9$ copies of target, $1 \times 10^{12}$ copies of capture oligomer, zero or $1 \times 10^{13}$ copies of complementary oligomer and $1 \times 10^9$ copies of the secondary capture oligomer. The results with or without complementary oligomer are shown in Table 6.

TABLE 6

| Input* (# copies) | Without complementary oligo | | With complementary oligo | |
|---|---|---|---|---|
| | Output (# copies) | Fold difference | Output (# copies) | Fold difference |
| Neat | $9.3 \times 10^7$ | — | $3.6 \times 10^8$ | — |
| 10-fold | $2.6 \times 10^7$ | 3.6 | $1.6 \times 10^8$ | 2.3 |
| 100-fold | $5.0 \times 10^5$ | 184 | $2.5 \times 10^7$ | 14.4 |

*Target amplicon produced in Step 1

In the absence of complementary oligomer, the secondary capture oligomer ($dT_{20}$-biotin) can bind to any of the capture oligomer molecules whether or not they are bound to target. In this experiment, $1 \times 10^{12}$ copies of capture oligomer and $1 \times 10^9$ copies of the secondary capture oligomer were used, i.e., there is a 1000-fold difference in these amounts. At the highest target level (neat), the majority of the capture oligomer will be bound to target and therefore the majority of secondary capture oligomer will bind to capture oligomer associated with target and the output copies after capture and elution will be relatively high. This is borne out in the data for the neat target input (without complementary oligo) where a relatively high output ($9.3 \times 10^7$ copies) is observed. However, at the 10-fold dilution of target there will be excess capture oligomer and therefore not all of it will bind to target. Some of the secondary capture oligomer will bind to capture oligomer associated with target but some will be to capture oligomer which is not bound to target. Therefore the output will go down, as is indeed observed (output=$2.6 \times 10^7$ copies). At the 100-fold dilution of target the majority of the capture oligomer will not be bound to target and likewise the majority of the secondary oligomer will bind to capture oligomer with is not associated with target. Therefore, the expectation under these conditions is a significantly decreased output, which is in fact observed (output=$5.0 \times 10^5$ copies).

In the presence of complementary oligomer, capture oligomer that has not bound to target will have the complementary oligomer bound which in turn will block the secondary capture reagent from binding. Conversely, capture oligomer that has bound to target will not have complementary oligomer bound (which has been displaced) which in turn will allow the secondary capture reagent to bind. Therefore, at all levels of target input tested in this experiment the output is expected to be higher in the presence of complementary oligomer than in the absence of complementary oligomer (results of which are discussed above). This is exactly what is observed (see Table 6). Furthermore, the data demonstrate that normalization is occurring, with only about a 2-fold difference between the output of the neat and 10-fold dilution target levels and only a little over a 14-fold difference between the output of neat and 100-fold target levels. The output at 100-fold target dilution is slightly lower than theoretically because the binding kinetics are slower due to this low level of target. Given longer incubation times the output would increase and the normalization factor would improve.

These data demonstrate that a capture oligomer and a complementary oligomer as described herein can be used to yield a pre-determined, normalized amount of target output across a 100-fold difference in input target amounts.

D. Generation of a Capturable Product that Contains Additional Sequence (e.g., Adaptors) at Both Ends of the Target Sequence Using a Capture Oligomer, a Complementary Oligomer, a Displacer Oligomer and a Forward Primer Oligomers.

PCR to amplify a segment from the E. faecium vanA gene was carried out using the primers:

```
Efm_vanA_F:
                              (SEQ ID NO: 23)
GGCTGCGATATTCAAAGCTCAG Efm_vanA_F:
                              (SEQ ID NO: 24)
CTGAACGCGCCGGCTTAAC
```

The primers were designed to generate an amplicon with the following sequence:

```
                              (SEQ ID NO: 25)
GGCTGCGATATTCAAAGCTCAGCAATTTGTATGGACAA

ATCGTTGACATACATCGTTGCGAAAAATGCTGGGATAG

CTACTCCCGCCTTTTGGGTTATTAATAAAGATGATAGG

CCGGTGGCAGCTACGTTTACCTATCCTGTTTTTGTTAA

GCCGGCGCGTTCAG
```

A capture oligomer designated PCR2R_adapter_CC was provided having the following sequence:

```
                                  (SEQ ID NO: 26)
AAAAAAAAAAAAAAAAAAAA/iSp18/CTCCTCTGGCA

CCGTGCTGCCTTGGCTTCATTGTGGTCGTAGCTGCCA

CCGGCCTAT
(iSp18 = Hexaethylene Glycol (HEG)
internal spacer (IDT))
```

This oligomer comprises the elements shown for the exemplary capture oligomer of FIG. 10A. In this oligomer, the 5' poly-A sequence is the capture sequence having first and second portions. iSp18 is the internal extension blocker. CTCCTCTGGCACCGTGCTGCCTTGGCTTCAT-TGTGGTC (SEQ ID NO: 27) is a spacer sequence having first and second portions. The target-hybridizing sequence (THS) is GTAGCTGCCACCGGCCTAT (SEQ ID NO: 28), which hybridizes specifically to a segment of the vanA gene sequence in the target amplicon.

A complementary oligo designated Blocker_vanA_001, comprising the elements shown for the exemplary complementary oligomer of FIG. 10A, was provided having the following sequence: CGGTGCCAGAG-GAGTTTTTTTTTT/invdt/(SEQ ID NO: 29) wherein invdt is an inverted T nucleotide which serves as a blocking moiety. In this oligomer, CGGTGCCAGAGGAG (SEQ ID NO: 30) is the complement of the first portion of the spacer sequence of the capture oligomer, and TTTTTTTTTT (SEQ ID NO: 31) is the complement of the second portion of the capture sequence.

Efm_vanA_R (sequence above), comprising the elements shown for the exemplary displacer oligomer of FIG. 8A, was provided. An oligomer designated PCR1F_adapter, comprising the elements shown for the exemplary forward primer with adapter of FIG. 8A, was also provided having the following sequence:

```
                                  (SEQ ID NO: 32)
AAAACGAGACATGCCGAGCATCCGCGGCTGCGATAT

TCAAAGCTCAG.
```

A secondary capture reagent with the following sequence was used:

```
dT20-biotin:
                                  (SEQ ID NO: 33)
TTTTTTTTTTTTTTTTTTTT/3'Biotin
```

The following primers and probe were used for quantitative PCR (qPCR) analysis of copy control products:

```
CCRPA_uni_F
                                  (SEQ ID NO: 34)
AAAACGAGACATGCCGAGCATC Efm_Probe_FAM
                                  (SEQ ID NO: 35)
5'FAM/TGCTGGGATAGCTACTCCCGCCTT TTGG/3'IowaBlack CC_Univ_Inner_Rev
                                  (SEQ ID NO: 36)
ACCGTGCTGCCTTGGCTTC
```

Protocol/Reaction Conditions (1).

(1) PCR amplicon was generated for the target vanA utilising the Efm_vanA_F and Efm_vanA_R primers shown above; amplicon was purified using the QIA-GEN QIAquick PCR Purification kit according to the manufacturer's instructions prior to quantitation via chip-based capillary electrophoresis using the Agilent BioAnalyzer.

(2) Capture oligomer, displacer oligomer and forward primer with adapter annealing and extension—An aliquot of the vanA amplicon containing approximately $1 \times 10^{12}$ copies was combined with annealing/extension reaction mixture yielding a final mixture consisting of 0.02 U/μl Deep Vent (exo-) Pol (NEB), 0.4× Deep Vent Pol reaction buffer, 0.012 mM dNTP's, 1.8 mM MgCl$_2$, 0.6 mg/ml BSA, $5 \times 10^{13}$ copies of the capture oligomer (PCR2R_adapter_CC), $\pm 1 \times 10^{13}$ copies of the displacer oligomer (Efm_vanA_R), and $5 \times 10^{13}$ copies of the forward primer with adapter (PCR1F adapter) for a final volume of 100 μL. Annealing and extension of the capture and displacer oligomers with the input amplicon and annealing and extension of the forward primer with adapter with the extension product of the capture oligomer all occurred in the same annealing/extension reaction using a thermal cycler according to the following thermal profile: 95° C. for 5 minutes then 64° C. for 20 minutes.

(3) Quantitation—Aliquots of each of the annealing extension reactions were diluted 100-fold and the amount of product contained in each was quantified by qPCR using primers CCRPA_uni_F and CC_Univ_Inner_Rev (targeting the universal adapter regions in the forward and reverse directions, respectively) along with the Efm_Probe_FAM.

Results and Conclusions:

A single-cycle annealing and extension reaction (single-cycle is defined as only 1 denaturation step, e.g., incubation at 95° C.; another cycle would begin with another heat denaturation step) was conducted using the input target and oligomers described above. As shown in Table 7, product was formed that contained universal adapters at both ends of the molecule, as evidenced by amplification using universal primers.

TABLE 7

| [LP-324] | |
| --- | --- |
| Displacer Oligo | Output (# copies) |
| + | 1.3E+11 |
| − | 2.8E+11 |

These data demonstrate that the embodiment of the present invention depicted in FIG. 8A can be used to generate product with an adapter (or other desired sequences) at both ends of the molecule using a single annealing/extension cycle. Further, these data demonstrate that at least one of the primer-adapter oligomers (PCR2R_adapter_CC in this case) can bind to an internal site in the target and not only the terminus. These data also demonstrate that the desired product can be generated in the absence of the displacer oligomer. Without wishing to be bound by any particular theory, it is possible that different mechanisms can function within the disclosed embodiment to yield the desired product. It is possible that multiple mechanisms are functioning in the presence of displacer oligomer to generate the observed results.

An additional experiment was performed essentially as described above with the following differences:

(2) Capture oligomer, displacer oligomer and forward primer with adapter annealing and extension—An aliquot of the vanA amplicon containing approximately $1 \times 10^{13}$ copies was combined with annealing/extension reaction mixture yielding a final mixture consisting of 0.02 U/µl Deep Vent (exo-) Pol (NEB), 0.4× Deep Vent Pol reaction buffer, 0.012 mM dNTP's, 1.8 mM MgCl$_2$, 0.6 mg/ml BSA, $5 \times 10^{14}$ copies of the capture oligomer (PCR2R_adapter_CC) and $5 \times 10^{14}$ copies of the forward primer with adapter (PCR1F adapter) for a final volume of 100 µL. Annealing and extension of this mixture was conducted using a thermal cycler according to the following thermal profile: 95° C. for 5 minutes then 64° C. for 15 minutes. At this point $5 \times 10^{14}$ copies of the displacer oligomer (Efm_vanA_R) was added to some replicates of the reaction mixture and to some only buffer was added, and annealing and extension were continued using the thermal profile 64° C. for 5 minutes, 75° C. for 5 minutes and 72° C. for 15 minutes.

Results and Conclusions:

A single-cycle annealing and extension reaction (single-cycle is defined as only 1 denaturation step, e.g., incubation at 95° C.; another cycle would begin with another heat denaturation step) was conducted using the input target and oligomers described above. The displacer oligomer was added to the annealing and extension reaction partway through the process to further optimize performance. As shown in Table 8, product was formed that contained universal adapters at both ends of the molecule, as evidenced by amplification using universal primers.

TABLE 7

| [LP-332] | |
| --- | --- |
| Displacer Oligo | Output (# copies) |
| + | 3.2E+12 |
| − | 1.9E+12 |

As above, these data demonstrate that the embodiment of the present invention depicted in FIG. 8A can be used to generate product with an adapter (or other desired sequences) at both ends of the molecule using a single annealing/extension cycle. Also as above, these data demonstrate that at least one of the primer-adapter oligomers (PCR2R_adapter_CC in this case) can bind to an internal site in the target and not only the terminus. Further, these data demonstrate that by adjusting the annealing and extension temperature profile—and in this case by adding the displacer oligomer partway through the process—that the overall performance can be improved. Of particular note is that under these conditions the amount of the desired product generated was greater when displacer oligomer was present than when it was absent, demonstrating that the displacement scheme is operating as shown if FIG. 8A. Again without wishing to be bound by any particular theory, it is possible that different mechanisms are also functioning within the disclosed embodiment to yield the desired product.

Protocol/Reaction Conditions (2).

(1) PCR amplicon was generated for the target vanA utilising the Efm_vanA_F and Efm_vanA_R primers shown above; amplicon was purified using the QIAGEN QIAquick PCR Purification kit according to the manufacturer's instructions prior to quantitation via chip-based capillary electrophoresis using the Agilent BioAnalyzer.

(2) Capture oligomer, displacer oligomer and forward primer with adapter annealing and extension—An aliquot of the vanA amplicon containing approximately $1 \times 10^{12}$ copies was combined with annealing/extension reaction mixture yielding a final mixture consisting of 0.02 U/µl Deep Vent (exo-) Pol (NEB), 0.4× Deep Vent Pol reaction buffer, 0.012 mM dNTP's, 1.8 mM MgCl$_2$, 0.6 mg/ml BSA, $5 \times 10^{13}$ copies of the capture oligomer (PCR2R_adapter_CC), $\pm 5 \times 10^{12}$ copies of the displacer oligomer (Efm_vanA_R), and $5 \times 10^{13}$ copies of the forward primer with adapter (PCR1F_adapter) for a final volume of 100 µL. Annealing and extension of the capture and displacer oligomers with the input amplicon and annealing and extension of the forward primer with adapter with the extension product of the capture oligomer all occurred in the same annealing/extension reaction using a thermal cycler according to the following thermal profile: 95° C. for 5 minutes then 64° C. for 20 minutes.

(3) Hybridization of the complement of the capture sequence of the capture oligomer—To the entire extension reaction mixture was added 50 µL of a secondary capture reagent at 3× concentration, resulting in a final concentration of 42 mM NaCl, 0.33 mg/ml BSA and $5 \times 10^{14}$ copies of the complement of the capture sequence (dT$_{20}$-biotin). Hybridization was carried out by incubating the reaction mix at 30° C. for 10 minutes.

(4) Capture of the amplicon and capture oligomer extension product/capture oligomer complex—A 50 µL aliquot (200 µg) of streptavidin-coated magnetic beads was added to the entire hybridization mixture (150 µL), resulting in a final concentration of 1 M NaCl, 5 mM TrisHCl (pH 7.5), 0.5 mM EDTA, 0.05% Tween 20 and 0.5 mg/ml BSA. The complex was captured onto the beads at 30° C. and the beads were washed using a wash reagent with the same composition as detailed immediately above.

(5) Elution—After the final wash was completed and the wash buffer removed, 30 µL of water was added to the bead pellet, the beads were resuspended and incubated at 70° C. for 2 minutes. The beads were pelleted with a magnet and the eluate was removed.

(6) Quantitation—Eluted product was quantified by qPCR using primers CCRPA_uni_F and CC_Univ_Inner_Rev (targeting the universal adapter regions in the forward and reverse directions, respectively) along with the Efm_Probe_FAM.

Results and Conclusions:

A single-cycle annealing and extension reaction was conducted using the input target and oligomers described above, the product was captured, washed, eluted and then quantitated using qPCR. As shown in Table 8, product was formed that contained universal adapters at both ends of the molecule which was captured and eluted, as evidenced by amplification using universal primers.

TABLE 8

| [LP-325] | |
| --- | --- |
| Displacer Oligo | Output (# copies) |
| + | 1.4E+09 |
| − | 1.5E+10 |

These data demonstrate that the embodiment of the present invention depicted in FIG. 8A can be used to generate product with an adapter (or other desired sequences) at both ends of the molecule using a single annealing/extension cycle and that this product can be isolated via capture onto beads, washing and elution. Further, these data demonstrate that at least one of the primer-adapter oligomers (PCR2R_adapter_CC in this case) can bind to an internal site in the target and not only the terminus. These data also demonstrate that the desired product can be generated in the absence of the displacer oligomer. Without wishing to be bound by any particular theory, it is possible that different mechanisms can function within the disclosed embodiment to yield the desired product. It is possible that multiple mechanisms are functioning in the presence of displacer oligomer to generate the observed results.

An additional experiment was performed essentially as described above with the following differences:

(2) Capture oligomer, displacer oligomer and forward primer with adapter annealing and extension—The annealing/extension reaction mixture was the same as that above except new samples were added that also contained $5\times10^{14}$ copies of the complementary oligomer (Blocker_vanA_001). Annealing and extension of the capture and displacer oligomers with the input amplicon, annealing of the complementary oligomer with the capture oligomer and annealing and extension of the forward primer with adapter with the extension product of the capture oligomer all occurred in the same annealing/extension reaction using a thermal cycler according to the following thermal profile shown in Table 9.

TABLE 9

[LP-329]
Thermal Profile

| Temp. | Time |
|---|---|
| 95° C. | 5 min |
| 75° C. | 30 sec |
| 74° C. | 30 sec |
| 73° C. | 30 sec |
| 72° C. | 30 sec |
| 71° C. | 30 sec |
| 70° C. | 30 sec |
| 69° C. | 2 min |
| 68° C. | 2 min |
| 67° C. | 2 min |
| 66° C. | 2 min |
| 65° C. | 2 min |
| 65° C. | 10 min |

(3) Hybridization of the complement of the capture sequence of the capture oligomer—To conditions were the same as above except $1\times10^9$ copies of the complement of the capture sequence ($dT_{20}$-biotin) were used.

Results and Conclusions:

A single-cycle annealing and extension reaction was conducted using the input target and oligomers described above, the product was captured using a pre-defined amount of the complement of the capture sequence ($dT_{20}$-biotin), washed, eluted and then quantitated using qPCR. The results are shown in Table 10.

TABLE 10

[LP-329]

| PCR Dilution | Output (# copies) | Fold Difference |
|---|---|---|
| Neat | 2.0E+06 | — |
| 10-fold | 4.3E+05 | 4.7 |

These data demonstrate that the embodiment of the present invention depicted in FIG. 8A can be used to generate product with an adapter (or other desired sequences) at both ends of the molecule using a single annealing/extension cycle and that this product can be isolated via capture onto beads, washing and elution. Further, the 10-fold difference in input target level was normalized to a 4.7-fold difference, which is over a 2-fold normalization factor. Further, these data demonstrate that at least one of the primer-adapter oligomers (PCR2R_adapter_CC in this case) can bind to an internal site in the target and not only the terminus.

An additional experiment was performed essentially as described above with the following differences:

(2) Capture oligomer, displacer oligomer and forward primer with adapter annealing and extension—The annealing/extension reaction mixture was the same as that above except 1E+13 and 1E+12 (10-fold dilution) copies/reaction of input target was used; new samples were added that also contained $5\times10^{14}$ copies of the complementary oligomer (Blocker_vanA_001). Annealing and extension of the capture oligomer with the input amplicon, annealing of the complementary oligomer with the capture oligomer and annealing and extension of the forward primer with adapter with the extension product of the capture oligomer all occurred in the same annealing/extension reaction using a thermal cycler according to the following thermal profile: 95° C. for 5 minutes, then 64° C. for 15 minutes.

(3) Hybridization of the complement of the capture sequence of the capture oligomer—To conditions were the same as above except $1\times10^9$ copies of the complement of the capture sequence ($dT_{20}$-biotin) were used. Hybridization was conducted at 30° C. for 30 minutes.

Results and Conclusions:

A single-cycle annealing and extension reaction was conducted using the input target and oligomers described above, the product was captured using a pre-defined amount of the complement of the capture sequence ($dT_{20}$-biotin), washed, eluted and then quantitated using qPCR. The results are shown in Table 10

TABLE 11

[LP-333]

| PCR Dilution | With Complementary Oligo | | Without Complementary Oligo | |
|---|---|---|---|---|
| | Output (# copies) | Fold Difference | Output (# copies) | Fold Difference |
| Neat | 1.8E+07 | — | 1.3E+06 | — |
| 10-fold | 2.7E+07 | 0.67 | 2.0E+06 | 0.65 |

These data demonstrate that the embodiment of the present invention depicted in FIG. 8A can be used to generate product with an adapter (or other desired sequences) at both ends of the molecule using a single annealing/extension cycle and that this product can be isolated via capture onto beads, washing and elution. Further, the 10-fold difference in input target level was normalized to a 0.67-fold difference (~1) when complementary oligo was present. Without complementary oligo the recovery of product was reduced over 10-fold, as would be expected while normalization was similar. Further, these data demonstrate that at least one of the primer-adapter oligomers (PCR2R_adapter_CC in this case) can bind to an internal site in the target and not only the terminus.

What is claimed is:

1. A capture oligomer comprising, in the 5' to 3' direction: a capture sequence,
an internal extension blocker,
a complement of the capture sequence,
a fourth additional sequence comprising an adaptor sequence; and
a target-hybridizing sequence,
wherein the complement of the capture sequence is configured to anneal to the capture sequence in the absence of an extended target sequence annealed to the target-hybridizing sequence and the complement of the capture sequence.

2. The capture oligomer of claim 1, wherein the capture oligomer has the formula

5'-A1-C-L-B-A2-C'-A3-RB-A4-THS-X-3' wherein A1 is an optionally present first additional sequence;
C is the capture sequence,
L is an optionally present linker,
B is the internal extension blocker,
A2 is an optionally present second additional sequence,
C' is the complement of the capture sequence,
A3 is an optionally present third additional sequence,
RB is an optionally present reversible extension blocker,
A4 is the fourth additional sequence,
THS is the target-hybridizing sequence; and
X is an optionally present blocking moiety.

3. The capture oligomer of claim 1, comprising a linker, which is optionally a nucleotide sequence or a non-nucleotide linker or a combination thereof, between the capture sequence and the internal extension blocker.

4. The capture oligomer of claim 1, wherein the internal extension blocker comprises any one or more of a non-nucleotide linker, or one or more abasic sites, non-natural nucleotides, or chemically modified natural nucleotides.

5. The capture oligomer of claim 1, wherein the capture oligomer comprises a reversible extension blocker located 5' of the target-hybridizing sequence.

6. The capture oligomer of claim 5, wherein the capture oligomer comprises a third additional sequence located 3' of the complement of the capture sequence and 5' of the target-hybridizing sequence, and the reversible extension blocker is located 3' of the adaptor sequence, optionally wherein the third additional sequence comprises an adaptor sequence.

7. The capture oligomer of claim 5, wherein the capture oligomer comprises a fourth additional sequence located 3' of the reversible extension blocker and 5' of the target-hybridizing sequence, optionally wherein the fourth additional sequence comprises an adaptor sequence.

8. The capture oligomer of claim 1, comprising a second additional sequence between the internal extension blocker and the complement of the capture sequence, optionally wherein the second additional sequence comprises a mixed-nucleotide segment.

9. The capture oligomer of claim 8, wherein the reversible extension blocker comprises Iso-dC or Iso-dG, xanthine or 5-(2,4 diaminopyritnidine), 2-amino-6-(N,Nditnethylamino) purine or pyridine-2-one, 4-Methylbenzitnidizole or 2,4 Difluorotoluene, 7-Azaindole or Isocarbostyril, dMM02 or d5SICS, dF or dQ; a chemically modified nucleotide or nucleotides wherein the modification is attached via a reversible linkage and the linkage can be reversed by providing any one or more of a chemical, an enzyme, a temperature change, a reagent composition change; a reversible nucleic acid structural feature; or a molecule reversibly bound to the capture oligomer, optionally wherein the reversibly bound molecule is a protein, an enzyme, a lipid, a carbohydrate, or a chemical moiety.

* * * * *